US010821446B1

(12) United States Patent
Handique et al.

(10) Patent No.: US 10,821,446 B1
(45) Date of Patent: Nov. 3, 2020

(54) FLUORESCENCE DETECTOR FOR MICROFLUIDIC DIAGNOSTIC SYSTEM

(71) Applicant: HANDYLAB, INC., Franklin Lakes, NJ (US)

(72) Inventors: Kalyan Handique, Ypsilanti, MI (US); Sundaresh N. Brahmasandra, Ann Arbor, MI (US)

(73) Assignee: HANDYLAB, INC., Franklin Lakes, NJ (US)

( * ) Notice: Subject to any disclaimer, the term of this patent is extended or adjusted under 35 U.S.C. 154(b) by 0 days.

(21) Appl. No.: 16/910,850

(22) Filed: Jun. 24, 2020

Related U.S. Application Data

(63) Continuation of application No. 15/795,842, filed on Oct. 27, 2017, now Pat. No. 10,695,764, which is a
(Continued)

(51) Int. Cl.
*B01L 3/00* (2006.01)
*B01L 1/00* (2006.01)
(Continued)

(52) U.S. Cl.
CPC ............ *B01L 7/52* (2013.01); *B01L 3/502715* (2013.01); *B01L 3/502723* (2013.01); *B01L 9/527* (2013.01); *C12Q 1/686* (2013.01); *G01N 21/6428* (2013.01); *B01L 3/502738* (2013.01); *B01L 2200/025* (2013.01); *B01L 2200/027* (2013.01); *B01L 2200/0684* (2013.01); *B01L 2300/021* (2013.01); *B01L 2300/022* (2013.01); *B01L 2300/045* (2013.01);
(Continued)

(58) Field of Classification Search
CPC .................. B01L 2300/046; B01L 2300/0627
See application file for complete search history.

(56) References Cited

U.S. PATENT DOCUMENTS

D189,404 S 12/1960 Nicolle
3,050,239 A 8/1962 Williams
(Continued)

FOREIGN PATENT DOCUMENTS

AU 1357102 3/2002
AU 3557502 7/2002
(Continued)

OTHER PUBLICATIONS

Allemand et al., "pH-Dependent Specific Binding and Combing of DNA", Biophys J. (1997) 73(4): 2064-2070.
(Continued)

*Primary Examiner* — Nathan A Bowers
(74) *Attorney, Agent, or Firm* — Knobbe, Martens, Olson & Bear, LLP

(57) ABSTRACT

The present technology provides for a fluorescent detector that is configured to detect light emitted for a probe characteristic of a polynucleotide. The polynucleotide is undergoing amplification in a microfluidic channel with which the detector is in optical communication. The detector is configured to detect minute quantities of polynucleotide, such as would be contained in a microfluidic volume. The detector can also be multiplexed to permit multiple concurrent measurements on multiple polynucleotides concurrently.

20 Claims, 37 Drawing Sheets

Related U.S. Application Data continuation of application No. 14/537,517, filed on Nov. 10, 2014, now Pat. No. 9,802,199, which is a continuation of application No. 11/940,321, filed on Nov. 14, 2007, now Pat. No. 8,883,490, which is a continuation-in-part of application No. 11/728,964, filed on Mar. 26, 2007, now Pat. No. 9,040,288.

(60) Provisional application No. 60/859,284, filed on Nov. 14, 2006, provisional application No. 60/959,437, filed on Jul. 13, 2007, provisional application No. 60/786,007, filed on Mar. 24, 2006, provisional application No. 60/859,284, filed on Nov. 14, 2006.

(51) Int. Cl.
*B01L 7/00* (2006.01)
*B01L 9/00* (2006.01)
*C12Q 1/686* (2018.01)
*G01N 21/64* (2006.01)

(52) U.S. Cl.
CPC . *B01L 2300/046* (2013.01); *B01L 2300/0861* (2013.01); *B01L 2300/1805* (2013.01); *B01L 2300/1822* (2013.01); *B01L 2300/1827* (2013.01); *B01L 2300/1838* (2013.01); *B01L 2300/1861* (2013.01); *G01N 2021/6419* (2013.01); *Y10S 435/808* (2013.01)

(56) References Cited

U.S. PATENT DOCUMENTS

| | | |
|---|---|---|
| 3,905,772 A | 9/1975 | Hartnett et al. |
| 3,985,649 A | 10/1976 | Eddelman |
| 4,018,089 A | 4/1977 | Dzula et al. |
| 4,018,652 A | 4/1977 | Lanham et al. |
| 4,038,192 A | 7/1977 | Serur |
| 4,055,395 A | 10/1977 | Honkawa et al. |
| D249,706 S | 9/1978 | Adamski |
| 4,139,005 A | 2/1979 | Dickey |
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,472,357 A | 9/1984 | Levy et al. |
| 4,504,582 A | 3/1985 | Swann |
| 4,522,786 A | 6/1985 | Ebersole |
| D279,817 S | 7/1985 | Chen et al. |
| D282,208 S | 1/1986 | Lowry |
| 4,599,315 A | 7/1986 | Terasaki et al. |
| 4,612,873 A | 9/1986 | Eberle |
| 4,612,959 A | 9/1986 | Costello |
| D288,478 S | 2/1987 | Carlson et al. |
| 4,647,432 A | 3/1987 | Wakatake |
| 4,654,127 A | 3/1987 | Baker et al. |
| 4,673,657 A | 6/1987 | Christian |
| 4,678,752 A | 7/1987 | Thorne et al. |
| 4,683,195 A | 7/1987 | Mullis et al. |
| 4,683,202 A | 7/1987 | Mullis |
| 4,698,302 A | 10/1987 | Whitehead et al. |
| D292,735 S | 11/1987 | Lovborg |
| 4,720,374 A | 1/1988 | Ramachandran |
| 4,724,207 A | 2/1988 | Hou et al. |
| 4,798,693 A | 1/1989 | Mase et al. |
| 4,800,022 A | 1/1989 | Leonard |
| 4,827,944 A | 5/1989 | Nugent |
| 4,841,786 A | 6/1989 | Schulz |
| D302,294 S | 7/1989 | Hillman |
| 4,855,110 A | 8/1989 | Marker et al. |
| 4,871,779 A | 10/1989 | Killat et al. |
| 4,895,650 A | 1/1990 | Wang |
| 4,919,829 A | 4/1990 | Gates et al. |
| 4,921,809 A | 5/1990 | Schiff et al. |
| 4,935,342 A | 6/1990 | Seligson et al. |
| 4,946,562 A | 8/1990 | Guruswamy |
| 4,949,742 A | 8/1990 | Rando et al. |
| D310,413 S | 9/1990 | Bigler et al. |
| 4,963,498 A | 10/1990 | Hillman |
| 4,967,950 A | 11/1990 | Legg et al. |
| D312,692 S | 12/1990 | Bradley |
| 4,978,502 A | 12/1990 | Dole et al. |
| 4,978,622 A | 12/1990 | Mishell et al. |
| 4,989,626 A | 2/1991 | Takagi et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,064,618 A | 11/1991 | Baker et al. |
| 5,071,531 A | 12/1991 | Soane |
| 5,091,328 A | 2/1992 | Miller |
| D324,426 S | 3/1992 | Fan et al. |
| 5,096,669 A | 3/1992 | Lauks et al. |
| D325,638 S | 4/1992 | Sloat et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,169,512 A | 12/1992 | Wiedenmann et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |
| 5,217,694 A | 6/1993 | Gibler et al. |
| 5,223,226 A | 6/1993 | Wittmer et al. |
| 5,229,297 A | 7/1993 | Schnipelsky et al. |
| D338,275 S | 8/1993 | Fischer et al. |
| 5,250,263 A | 10/1993 | Manz |
| 5,252,743 A | 10/1993 | Barrett et al. |
| 5,256,376 A | 10/1993 | Callan et al. |
| 5,273,716 A | 12/1993 | Northrup et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen et al. |
| 5,311,996 A | 5/1994 | Duffy et al. |
| 5,316,727 A | 5/1994 | Suzuki et al. |
| 5,327,038 A | 7/1994 | Culp |
| 5,339,486 A | 8/1994 | Persic, Jr. |
| D351,475 S | 10/1994 | Gerber |
| D351,913 S | 10/1994 | Hieb et al. |
| 5,364,591 A | 11/1994 | Green et al. |
| 5,372,946 A | 12/1994 | Cusak et al. |
| 5,374,395 A | 12/1994 | Robinson |
| 5,389,339 A | 2/1995 | Petschek et al. |
| D356,232 S | 3/1995 | Armstrong et al. |
| 5,397,709 A | 3/1995 | Berndt |
| 5,401,465 A | 3/1995 | Smethers et al. |
| 5,411,708 A | 5/1995 | Moscetta et al. |
| 5,414,245 A | 5/1995 | Hackleman |
| 5,415,839 A | 5/1995 | Zaun et al. |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |
| 5,443,791 A | 8/1995 | Cathcart et al. |
| 5,474,796 A | 12/1995 | Brennan |
| 5,475,487 A | 12/1995 | Mariella, Jr. et al. |
| D366,116 S | 1/1996 | Biskupski |
| 5,486,335 A | 1/1996 | Wilding et al. |

(56) References Cited

U.S. PATENT DOCUMENTS

| | | |
|---|---|---|
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |
| 5,578,270 A | 11/1996 | Reichler et al. |
| 5,578,818 A | 11/1996 | Kain et al. |
| 5,579,928 A | 12/1996 | Anukwuem |
| 5,580,523 A | 12/1996 | Bard |
| 5,582,884 A | 12/1996 | Ball et al. |
| 5,582,988 A | 12/1996 | Backus et al. |
| 5,585,069 A | 12/1996 | Zanucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| 5,609,910 A | 3/1997 | Hackleman |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,639,428 A | 6/1997 | Cottingham |
| 5,643,738 A | 7/1997 | Zanzucchi et al. |
| 5,645,801 A | 7/1997 | Bouma et al. |
| 5,646,039 A | 7/1997 | Northrup et al. |
| 5,646,049 A | 7/1997 | Tayi |
| 5,647,994 A | 7/1997 | Tuunanen et al. |
| 5,651,839 A | 7/1997 | Rauf |
| 5,652,141 A | 7/1997 | Henco et al. |
| 5,652,149 A | 7/1997 | Mileaf et al. |
| D382,346 S | 8/1997 | Buhler et al. |
| D382,647 S | 8/1997 | Staples et al. |
| 5,654,141 A | 8/1997 | Mariani et al. |
| 5,658,515 A | 8/1997 | Lee et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,683,659 A | 11/1997 | Hovatter |
| 5,699,157 A | 12/1997 | Parce et al. |
| 5,700,637 A | 12/1997 | Southern |
| 5,705,813 A | 1/1998 | Apffel et al. |
| 5,721,136 A | 2/1998 | Finney et al. |
| 5,725,831 A | 3/1998 | Reichler et al. |
| 5,726,026 A | 3/1998 | Wilding et al. |
| 5,726,404 A | 3/1998 | Brody |
| 5,726,944 A | 3/1998 | Pelley et al. |
| 5,731,212 A | 3/1998 | Gavin et al. |
| 5,744,366 A | 4/1998 | Kricka et al. |
| 5,746,978 A | 5/1998 | Bienhaus et al. |
| 5,747,666 A | 5/1998 | Willis |
| 5,750,015 A | 5/1998 | Soane et al. |
| 5,755,942 A | 5/1998 | Zanzucchi et al. |
| 5,762,874 A | 6/1998 | Seaton et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,783,148 A | 7/1998 | Cottingham et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,819,749 A | 10/1998 | Lee et al. |
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,846,493 A | 12/1998 | Bankier et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,187 A | 1/1999 | Ramsey et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,869,244 A | 2/1999 | Martin et al. |
| 5,872,010 A | 2/1999 | Karger et al. |
| 5,872,623 A | 2/1999 | Stabile et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benvegnu et al. |
| 5,911,737 A | 6/1999 | Lee et al. |
| 5,912,124 A | 6/1999 | Kumar |
| 5,912,134 A | 6/1999 | Shartle |
| 5,914,229 A | 6/1999 | Loewy |
| 5,916,522 A | 6/1999 | Boyd et al. |
| 5,916,776 A | 6/1999 | Kumar |
| 5,919,646 A | 7/1999 | Okun et al. |
| 5,919,711 A | 7/1999 | Boyd et al. |
| 5,922,591 A | 7/1999 | Anderson et al. |
| 5,927,547 A | 7/1999 | Papen et al. |
| 5,928,161 A | 7/1999 | Krulevitch et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |
| 5,935,401 A | 8/1999 | Amigo |
| 5,939,291 A | 8/1999 | Loewy et al. |
| 5,939,312 A | 8/1999 | Baier et al. |
| 5,942,443 A | 8/1999 | Parce et al. |
| 5,944,717 A | 8/1999 | Lee et al. |
| D413,677 S | 9/1999 | Dumitrescu et al. |
| D414,271 S | 9/1999 | Mendoza |
| 5,948,227 A | 9/1999 | Dubrow |
| 5,948,363 A | 9/1999 | Gaillard |
| 5,948,673 A | 9/1999 | Cottingham |
| 5,955,028 A | 9/1999 | Chow |
| 5,955,029 A | 9/1999 | Wilding et al. |
| 5,957,579 A | 9/1999 | Kopf-Sill et al. |
| 5,958,203 A | 9/1999 | Parce et al. |
| 5,958,349 A | 9/1999 | Petersen et al. |
| 5,958,694 A | 9/1999 | Nikiforov |
| 5,959,221 A | 9/1999 | Boyd et al. |
| 5,959,291 A | 9/1999 | Jensen |
| 5,935,522 A | 10/1999 | Swerdlow et al. |
| 5,964,995 A | 10/1999 | Nikiforov et al. |
| 5,964,997 A | 10/1999 | McBride |
| 5,965,001 A | 10/1999 | Chow et al. |

(56) References Cited

U.S. PATENT DOCUMENTS

| | | |
|---|---|---|
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| 5,973,138 A | 10/1999 | Collis |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,985,651 A | 11/1999 | Hunicke-Smith |
| 5,989,402 A | 11/1999 | Chow et al. |
| 5,992,820 A | 11/1999 | Fare et al. |
| 5,993,611 A | 11/1999 | Moroney, III et al. |
| 5,993,750 A | 11/1999 | Ghosh et al. |
| 5,997,708 A | 12/1999 | Craig |
| 6,001,229 A | 12/1999 | Ramsey |
| 6,001,231 A | 12/1999 | Kopf-Sill |
| 6,001,307 A | 12/1999 | Naka et al. |
| 6,004,450 A | 12/1999 | Northrup et al. |
| 6,004,515 A | 12/1999 | Parce et al. |
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood, III |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,033,880 A | 3/2000 | Haff et al. |
| 6,043,080 A | 3/2000 | Lipshutz et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,063,589 A | 5/2000 | Kellogg et al. |
| 6,068,751 A | 5/2000 | Neukermans |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,117,398 A | 9/2000 | Bienhaus et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,143,547 A | 11/2000 | Hsu |
| 6,149,787 A | 11/2000 | Chow et al. |
| 6,149,872 A | 11/2000 | Mack et al. |
| 6,156,199 A | 12/2000 | Zuk, Jr. |
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow et al. |
| 6,180,950 B1 | 1/2001 | Olsen |
| D438,311 S | 2/2001 | Yamanishi et al. |
| 6,190,619 B1 | 2/2001 | Kilcoin et al. |
| 6,194,563 B1 | 2/2001 | Cruickshank |
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,211,989 B1 * | 4/2001 | Wulf ............... G01N 21/6452 356/317 |
| 6,213,151 B1 | 4/2001 | Jacobson et al. |
| 6,221,600 B1 | 4/2001 | MacLeod et al. |
| 6,228,635 B1 | 5/2001 | Armstrong et al. |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Foss et al. |
| 6,238,626 B1 | 5/2001 | Higuchi et al. |
| 6,251,343 B1 | 6/2001 | Dubrow et al. |
| 6,254,826 B1 | 7/2001 | Acosta et al. |
| 6,259,635 B1 | 7/2001 | Khouri et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,284,470 B1 | 9/2001 | Bitner et al. |
| 6,287,254 B1 | 9/2001 | Dodds |
| 6,287,774 B1 | 9/2001 | Nikiforov |
| 6,291,248 B1 | 9/2001 | Haj-Ahmad |
| 6,294,063 B1 | 9/2001 | Becker et al. |
| 6,300,124 B1 | 10/2001 | Blumenfeld et al. |
| 6,302,134 B1 | 10/2001 | Kellogg et al. |
| 6,302,304 B1 | 10/2001 | Spencer |
| 6,303,343 B1 | 10/2001 | Kopf-sill |
| 6,306,273 B1 | 10/2001 | Wainright et al. |
| 6,306,590 B1 | 10/2001 | Mehta et al. |
| 6,310,199 B1 | 10/2001 | Smith et al. |
| 6,316,774 B1 | 11/2001 | Giebeler et al. |
| 6,319,469 B1 | 11/2001 | Mian et al. |
| 6,319,474 B1 | 11/2001 | Krulevitch et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,561 B1 | 4/2002 | Rutishauser et al. |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Maher et al. |
| 6,401,552 B1 | 6/2002 | Elkins |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | McReynolds |
| D461,906 S | 8/2002 | Pham |
| 6,428,987 B2 | 8/2002 | Franzen |
| 6,430,512 B1 | 8/2002 | Gallagher |

(56) References Cited

U.S. PATENT DOCUMENTS

| | | |
|---|---|---|
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,458,259 B1 | 10/2002 | Parce et al. |
| 6,461,570 B2 | 10/2002 | Ishihara et al. |
| 6,465,257 B1 | 10/2002 | Parce et al. |
| 6,468,761 B2 | 10/2002 | Yang et al. |
| 6,472,141 B2 | 10/2002 | Nikiforov |
| D466,219 S | 11/2002 | Wynschenk et al. |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,186 B1 | 1/2003 | Zou et al. |
| 6,509,193 B1 | 1/2003 | Tajima |
| 6,511,853 B1 | 1/2003 | Kopf-sill et al. |
| D470,595 S | 2/2003 | Crisanti et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,181 B1 | 2/2003 | Northrup et al. |
| 6,521,188 B1 | 2/2003 | Webster |
| 6,524,456 B1 | 2/2003 | Ramsey et al. |
| 6,524,532 B1 | 2/2003 | Northrup |
| 6,524,790 B1 | 2/2003 | Kopf-sill et al. |
| D472,324 S | 3/2003 | Rumore et al. |
| 6,534,295 B2 | 3/2003 | Tai et al. |
| 6,537,432 B1 | 3/2003 | Schneider et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,565,815 B1 | 5/2003 | Chang et al. |
| 6,569,607 B2 | 5/2003 | McReynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,613,211 B1 | 9/2003 | Mccormick et al. |
| 6,613,512 B1 | 9/2003 | Kopf-sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| 6,633,785 B1 | 10/2003 | Kasahara et al. |
| D482,796 S | 11/2003 | Oyama et al. |
| 6,640,981 B2 | 11/2003 | Lafond et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,153 B2 | 12/2003 | Stern |
| D484,989 S | 1/2004 | Gebrian |
| 6,672,458 B2 | 1/2004 | Hansen et al. |
| 6,681,616 B2 | 1/2004 | Spaid et al. |
| 6,681,788 B2 | 1/2004 | Parce et al. |
| 6,685,813 B2 | 2/2004 | Williams et al. |
| 6,692,700 B2 | 2/2004 | Handique |
| 6,695,009 B2 | 2/2004 | Chien et al. |
| 6,699,713 B2 | 3/2004 | Benett et al. |
| 6,706,519 B1 | 3/2004 | Kellogg et al. |
| 6,720,148 B1 | 4/2004 | Nikiforov |
| 6,730,206 B2 | 5/2004 | Ricco et al. |
| 6,733,645 B1 | 5/2004 | Chow |
| 6,734,401 B2 | 5/2004 | Bedingham et al. |
| 6,737,026 B1 | 5/2004 | Bergh et al. |
| 6,740,518 B1 | 5/2004 | Duong et al. |
| D491,272 S | 6/2004 | Alden et al. |
| D491,273 S | 6/2004 | Biegler et al. |
| D491,276 S | 6/2004 | Langille |
| 6,750,661 B2 | 6/2004 | Brooks et al. |
| 6,752,966 B1 | 6/2004 | Chazan |
| 6,756,019 B1 | 6/2004 | Dubrow et al. |
| 6,762,049 B2 | 7/2004 | Zou et al. |
| 6,764,859 B1 | 7/2004 | Kreuwel et al. |
| 6,766,817 B2 | 7/2004 | Dias da Silva |
| 6,773,567 B1 | 8/2004 | Wolk |
| 6,777,184 B2 | 8/2004 | Nikiforov et al. |
| 6,783,962 B1 | 8/2004 | Olander et al. |
| D495,805 S | 9/2004 | Lea et al. |
| 6,787,015 B2 | 9/2004 | Lackritz et al. |
| 6,787,016 B2 | 9/2004 | Tan et al. |
| 6,787,111 B2 | 9/2004 | Roach et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D499,813 S | 12/2004 | Wu |
| D500,142 S | 12/2004 | Crisanti et al. |
| D500,363 S | 12/2004 | Fanning et al. |
| 6,827,831 B1 | 12/2004 | Chow et al. |
| 6,827,906 B1 | 12/2004 | Bjornson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,858,185 B1 | 2/2005 | Kopf-sill et al. |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,900,889 B2 | 5/2005 | Bjornson et al. |
| 6,905,583 B2 | 6/2005 | Wainright et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | Dias da Silva |
| D508,999 S | 8/2005 | Fanning et al. |
| 6,939,451 B2 | 9/2005 | Zhao et al. |
| 6,940,598 B2 | 9/2005 | Christel et al. |
| 6,942,771 B1 | 9/2005 | Kayyem |
| 6,951,632 B2 | 10/2005 | Unger et al. |
| 6,958,392 B2 | 10/2005 | Fomovskaia et al. |
| D512,155 S | 11/2005 | Matsumoto |
| 6,964,747 B2 | 11/2005 | Banerjee et al. |
| 6,977,163 B1 | 12/2005 | Mehta |
| 6,979,424 B2 | 12/2005 | Northrup et al. |
| 6,984,516 B2 | 1/2006 | Briscoe et al. |
| D515,707 S | 2/2006 | Sinohara et al. |
| D516,221 S | 2/2006 | Wohlstadter et al. |
| 7,001,853 B1 | 2/2006 | Brown et al. |
| 7,004,184 B2 | 2/2006 | Handique et al. |
| D517,554 S | 3/2006 | Yanagisawa et al. |

(56) References Cited

U.S. PATENT DOCUMENTS

| | | |
|---|---|---|
| 7,010,391 B2 | 3/2006 | Handique et al. |
| 7,023,007 B2 | 4/2006 | Gallagher |
| 7,024,281 B1 | 4/2006 | Unno |
| 7,036,667 B2 | 5/2006 | Greenstein et al. |
| 7,037,416 B2 | 5/2006 | Parce et al. |
| 7,038,472 B1 | 5/2006 | Chien |
| 7,039,527 B2 | 5/2006 | Tripathi et al. |
| 7,040,144 B2 | 5/2006 | Spaid et al. |
| 7,049,558 B2 | 5/2006 | Baer et al. |
| D523,153 S | 6/2006 | Akashi et al. |
| 7,055,695 B2 | 6/2006 | Greenstein et al. |
| 7,060,171 B1 | 6/2006 | Nikiforov et al. |
| 7,066,586 B2 | 6/2006 | Dias da Silva |
| 7,069,952 B1 | 7/2006 | McReynolds et al. |
| 7,072,036 B2 | 7/2006 | Jones et al. |
| 7,099,778 B2 | 8/2006 | Chien |
| D528,215 S | 9/2006 | Malmsater |
| 7,101,467 B2 | 9/2006 | Spaid |
| 7,105,304 B1 | 9/2006 | Nikiforov et al. |
| D531,321 S | 10/2006 | Godfrey et al. |
| 7,118,892 B2 | 10/2006 | Ammann et al. |
| 7,118,910 B2 | 10/2006 | Unger et al. |
| 7,122,799 B2 | 10/2006 | Hsieh et al. |
| 7,135,144 B2 | 11/2006 | Christel et al. |
| 7,138,032 B2 | 11/2006 | Gandhi et al. |
| D534,280 S | 12/2006 | Gomm et al. |
| 7,150,814 B1 | 12/2006 | Parce et al. |
| 7,150,999 B1 | 12/2006 | Shuck |
| D535,403 S | 1/2007 | Isozaki et al. |
| 7,160,423 B2 | 1/2007 | Chien et al. |
| 7,161,356 B1 | 1/2007 | Chien |
| 7,169,277 B2 | 1/2007 | Ausserer et al. |
| 7,169,601 B1 | 1/2007 | Northrup et al. |
| 7,169,618 B2 | 1/2007 | Skold |
| D537,951 S | 3/2007 | Okamoto et al. |
| D538,436 S | 3/2007 | Patadia et al. |
| 7,188,001 B2 | 3/2007 | Young et al. |
| 7,192,557 B2 | 3/2007 | Wu et al. |
| 7,195,986 B1 | 3/2007 | Bousse et al. |
| 7,205,154 B2 | 4/2007 | Corson |
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |
| D549,827 S | 8/2007 | Maeno et al. |
| 7,252,928 B1 | 8/2007 | Hafeman et al. |
| 7,255,833 B2 | 8/2007 | Chang et al. |
| 7,270,786 B2 | 9/2007 | Parunak et al. |
| D554,069 S | 10/2007 | Bolotin et al. |
| D554,070 S | 10/2007 | Bolotin et al. |
| 7,276,208 B2 | 10/2007 | Sevigny et al. |
| 7,276,330 B2 | 10/2007 | Chow et al. |
| 7,288,228 B2 | 10/2007 | Lefebvre |
| 7,297,313 B1 | 11/2007 | Northrup et al. |
| D556,914 S | 12/2007 | Okamoto et al. |
| 7,303,727 B1 | 12/2007 | Dubrow et al. |
| D559,995 S | 1/2008 | Handique et al. |
| 7,315,376 B2 | 1/2008 | Bickmore et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,480,042 B1 | 1/2009 | Phillips et al. |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Burd Mehta |
| 7,527,769 B2 | 5/2009 | Bunch et al. |
| D595,423 S | 6/2009 | Johansson et al. |
| 7,553,671 B2 | 6/2009 | Sinclair et al. |
| D596,312 S | 7/2009 | Giraud et al. |
| D598,566 S | 8/2009 | Allaer |
| 7,578,976 B1 | 8/2009 | Northrup et al. |
| D599,234 S | 9/2009 | Ito |
| 7,595,197 B2 | 9/2009 | Brasseur |
| 7,604,938 B2 | 10/2009 | Takahashi et al. |
| 7,622,296 B2 | 11/2009 | Joseph et al. |
| 7,628,902 B2 | 12/2009 | Knowlton et al. |
| 7,633,606 B2 | 12/2009 | Northrup et al. |
| 7,635,588 B2 | 12/2009 | King et al. |
| 7,645,581 B2 | 1/2010 | Knapp et al. |
| 7,670,559 B2 | 3/2010 | Chien et al. |
| 7,674,431 B2 | 3/2010 | Ganesan |
| 7,689,022 B2 | 3/2010 | Weiner et al. |
| 7,704,735 B2 | 4/2010 | Facer et al. |
| 7,705,739 B2 | 4/2010 | Northrup et al. |
| 7,723,123 B1 | 5/2010 | Murphy et al. |
| D618,820 S | 6/2010 | Wilson et al. |
| 7,727,371 B2 | 6/2010 | Kennedy et al. |
| 7,727,477 B2 | 6/2010 | Boronkay et al. |
| 7,744,817 B2 | 6/2010 | Bui |
| D621,060 S | 8/2010 | Handique |
| 7,785,868 B2 | 8/2010 | Yuan et al. |
| D628,305 S | 11/2010 | Gorrec et al. |
| 7,829,025 B2 | 11/2010 | Ganesan et al. |
| 7,858,366 B2 | 12/2010 | Northrup et al. |
| 7,867,776 B2 | 1/2011 | Kennedy et al. |
| 7,892,819 B2 | 2/2011 | Wilding et al. |
| D637,737 S | 5/2011 | Wilson et al. |
| 7,955,864 B2 | 6/2011 | Cox et al. |
| 7,987,022 B2 | 7/2011 | Handique et al. |
| 7,998,708 B2 | 8/2011 | Handique et al. |
| 8,053,214 B2 | 11/2011 | Northrup |
| 8,071,056 B2 | 12/2011 | Burns et al. |
| 8,088,616 B2 | 1/2012 | Handique |
| 8,105,783 B2 | 1/2012 | Handique |
| 8,110,158 B2 | 2/2012 | Handique |
| 8,133,671 B2 | 3/2012 | Williams et al. |
| 8,182,763 B2 | 5/2012 | Duffy et al. |
| 8,246,919 B2 | 8/2012 | Herchenbach et al. |
| 8,273,308 B2 | 9/2012 | Handique et al. |
| D669,597 S | 10/2012 | Cavada et al. |
| 8,287,820 B2 | 10/2012 | Williams et al. |
| 8,323,584 B2 | 12/2012 | Ganesan |
| 8,323,900 B2 | 12/2012 | Handique et al. |
| 8,324,372 B2 | 12/2012 | Brahmasandra et al. |
| 8,415,103 B2 | 4/2013 | Handique |
| 8,420,015 B2 | 4/2013 | Ganesan et al. |
| 8,440,149 B2 | 5/2013 | Handique |
| 8,470,586 B2 | 6/2013 | Wu et al. |
| 8,473,104 B2 | 6/2013 | Handique et al. |
| D686,749 S | 7/2013 | Trump |
| D687,567 S | 8/2013 | Jungheim et al. |
| D692,162 S | 10/2013 | Lentz et al. |
| 8,592,157 B2 | 11/2013 | Petersen et al. |
| 8,679,831 B2 | 3/2014 | Handique et al. |
| D702,854 S | 4/2014 | Nakahana et al. |
| 8,685,341 B2 | 4/2014 | Ganesan |
| 8,703,069 B2 | 4/2014 | Handique et al. |
| 8,709,787 B2 | 4/2014 | Handique |
| 8,710,211 B2 | 4/2014 | Brahmasandra et al. |
| 8,734,733 B2 | 5/2014 | Handique |
| D710,024 S | 7/2014 | Guo |
| 8,765,076 B2 | 7/2014 | Handique et al. |
| 8,765,454 B2 | 7/2014 | Zhou et al. |
| 8,768,517 B2 | 7/2014 | Handique et al. |
| 8,852,862 B2 | 10/2014 | Wu et al. |
| 8,883,490 B2 | 11/2014 | Handique et al. |
| 8,894,947 B2 | 11/2014 | Ganesan et al. |
| 8,895,311 B1 | 11/2014 | Handique et al. |
| D729,404 S | 5/2015 | Teich et al. |
| 9,028,773 B2 | 5/2015 | Ganesan |
| 9,040,288 B2 | 5/2015 | Handique et al. |
| 9,051,604 B2 | 6/2015 | Handique |
| 9,080,207 B2 | 7/2015 | Handique et al. |

(56) References Cited

U.S. PATENT DOCUMENTS

| | | |
|---|---|---|
| D742,027 S | 10/2015 | Lentz et al. |
| 9,186,677 B2 | 11/2015 | Williams et al. |
| 9,217,143 B2 | 12/2015 | Brahmasandra et al. |
| 9,222,954 B2 | 12/2015 | Lentz et al. |
| 9,234,236 B2 | 1/2016 | Thomas et al. |
| 9,238,223 B2 | 1/2016 | Handique |
| 9,259,734 B2 | 2/2016 | Williams et al. |
| 9,259,735 B2 | 2/2016 | Handique et al. |
| 9,347,586 B2 | 5/2016 | Williams et al. |
| 9,480,983 B2 | 11/2016 | Lentz et al. |
| 9,528,142 B2 | 12/2016 | Handique |
| 9,618,139 B2 | 4/2017 | Handique |
| D787,087 S | 6/2017 | Duffy et al. |
| 9,670,528 B2 | 6/2017 | Handique et al. |
| 9,677,121 B2 | 6/2017 | Ganesan et al. |
| 9,701,957 B2 | 7/2017 | Wilson et al. |
| 9,745,623 B2 | 8/2017 | Steel |
| 9,765,389 B2 | 9/2017 | Gubatayao et al. |
| 9,789,481 B2 | 10/2017 | Petersen et al. |
| 9,802,199 B2 | 10/2017 | Handique et al. |
| 9,815,057 B2 | 11/2017 | Handique |
| 9,958,466 B2 | 5/2018 | Dalbert et al. |
| 10,065,185 B2 | 9/2018 | Handique |
| 10,071,376 B2 | 9/2018 | Williams et al. |
| 10,076,754 B2 | 9/2018 | Lentz et al. |
| 10,100,302 B2 | 10/2018 | Brahmasandra et al. |
| 10,139,012 B2 | 11/2018 | Handique |
| 10,179,910 B2 | 1/2019 | Duffy et al. |
| 10,234,474 B2 | 3/2019 | Williams et al. |
| 10,351,901 B2 | 7/2019 | Ganesan et al. |
| 10,364,456 B2 | 7/2019 | Wu et al. |
| 10,443,088 B1 | 10/2019 | Wu et al. |
| 10,494,663 B1 | 12/2019 | Wu et al. |
| 10,571,935 B2 | 2/2020 | Handique et al. |
| 10,590,410 B2 | 3/2020 | Brahmasandra et al. |
| 10,604,788 B2 | 3/2020 | Wu et al. |
| 10,695,764 B2 | 6/2020 | Handique et al. |
| 10,710,069 B2 | 7/2020 | Handique et al. |
| 10,717,085 B2 | 7/2020 | Williams et al. |
| 10,731,201 B2 | 8/2020 | Handique et al. |
| 2001/0005489 A1 | 6/2001 | Roach et al. |
| 2001/0012492 A1 | 8/2001 | Acosta et al. |
| 2001/0016358 A1 | 8/2001 | Osawa et al. |
| 2001/0021355 A1 | 9/2001 | Baugh et al. |
| 2001/0023848 A1 | 9/2001 | Gjerde et al. |
| 2001/0038450 A1 | 11/2001 | McCaffrey et al. |
| 2001/0045358 A1 | 11/2001 | Kopf-Sill et al. |
| 2001/0046702 A1 | 11/2001 | Schembri |
| 2001/0048899 A1 | 12/2001 | Marouiss et al. |
| 2001/0055765 A1 | 12/2001 | O'Keefe et al. |
| 2002/0001848 A1 | 1/2002 | Bedingham et al. |
| 2002/0008053 A1 | 1/2002 | Hansen et al. |
| 2002/0009015 A1 | 1/2002 | Laugharn, Jr. et al. |
| 2002/0014443 A1 | 2/2002 | Hansen et al. |
| 2002/0015667 A1 | 2/2002 | Chow |
| 2002/0021983 A1 | 2/2002 | Comte et al. |
| 2002/0022261 A1 | 2/2002 | Anderson et al. |
| 2002/0037499 A1 | 3/2002 | Quake et al. |
| 2002/0039783 A1 | 4/2002 | McMillan et al. |
| 2002/0047003 A1 | 4/2002 | Bedingham et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0068821 A1 | 6/2002 | Gundling |
| 2002/0090320 A1 | 7/2002 | Burow et al. |
| 2002/0092767 A1 | 7/2002 | Bjornson et al. |
| 2002/0094303 A1 | 7/2002 | Yamamoto et al. |
| 2002/0131903 A1 | 9/2002 | Ingenhoven et al. |
| 2002/0141903 A1 | 10/2002 | Parunak et al. |
| 2002/0143297 A1 | 10/2002 | Francavilla et al. |
| 2002/0155010 A1 | 10/2002 | Karp et al. |
| 2002/0155477 A1 | 10/2002 | Ito |
| 2002/0169518 A1 | 11/2002 | Luoma et al. |
| 2002/0173032 A1 | 11/2002 | Zou et al. |
| 2002/0176804 A1 | 11/2002 | Strand et al. |
| 2002/0187557 A1 | 12/2002 | Hobbs et al. |
| 2002/0192808 A1 | 12/2002 | Gambini et al. |
| 2003/0008308 A1 | 1/2003 | Enzelberger et al. |
| 2003/0019522 A1 | 1/2003 | Parunak |
| 2003/0022392 A1 | 1/2003 | Hudak |
| 2003/0049833 A1 | 3/2003 | Chen et al. |
| 2003/0059823 A1 | 3/2003 | Matsunaga et al. |
| 2003/0064507 A1 | 4/2003 | Gallagher et al. |
| 2003/0072683 A1 | 4/2003 | Stewart et al. |
| 2003/0073106 A1 | 4/2003 | Johansen et al. |
| 2003/0083686 A1 | 5/2003 | Freeman et al. |
| 2003/0087300 A1 | 5/2003 | Knapp et al. |
| 2003/0096310 A1 | 5/2003 | Hansen et al. |
| 2003/0099954 A1 | 5/2003 | Miltenyi et al. |
| 2003/0127327 A1 | 7/2003 | Kurnik |
| 2003/0136679 A1 | 7/2003 | Bohn et al. |
| 2003/0156991 A1 | 8/2003 | Halas et al. |
| 2003/0180192 A1 | 9/2003 | Seippel |
| 2003/0186295 A1 | 10/2003 | Colin et al. |
| 2003/0190608 A1 | 10/2003 | Blackburn et al. |
| 2003/0199081 A1 | 10/2003 | Wilding et al. |
| 2003/0211517 A1 | 11/2003 | Carulli et al. |
| 2004/0014202 A1 | 1/2004 | King et al. |
| 2004/0014238 A1 | 1/2004 | Krug et al. |
| 2004/0018116 A1 | 1/2004 | Desmond et al. |
| 2004/0018119 A1 | 1/2004 | Massaro |
| 2004/0022689 A1 | 2/2004 | Wulf et al. |
| 2004/0029258 A1 | 2/2004 | Heaney et al. |
| 2004/0029260 A1 | 2/2004 | Hansen et al. |
| 2004/0037739 A1 | 2/2004 | McNeely et al. |
| 2004/0043479 A1 | 3/2004 | Briscoe et al. |
| 2004/0053290 A1 | 3/2004 | Terbrueggen et al. |
| 2004/0063217 A1 | 4/2004 | Webster et al. |
| 2004/0065655 A1 | 4/2004 | Brown |
| 2004/0072278 A1 | 4/2004 | Chou et al. |
| 2004/0072375 A1 | 4/2004 | Gjerde et al. |
| 2004/0076996 A1 | 4/2004 | Kondo et al. |
| 2004/0086427 A1 | 5/2004 | Childers et al. |
| 2004/0086956 A1 | 5/2004 | Bachur |
| 2004/0132059 A1 | 7/2004 | Scurati et al. |
| 2004/0141887 A1 | 7/2004 | Mainquist et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0189311 A1 | 9/2004 | Glezer et al. |
| 2004/0197810 A1 | 10/2004 | Takenaka et al. |
| 2004/0200909 A1 | 10/2004 | McMillan et al. |
| 2004/0209331 A1 | 10/2004 | Ririe |
| 2004/0209354 A1 | 10/2004 | Mathies et al. |
| 2004/0224317 A1 | 11/2004 | Kordunsky et al. |
| 2004/0235154 A1 | 11/2004 | Oh et al. |
| 2004/0240097 A1 | 12/2004 | Evans |
| 2005/0009174 A1 | 1/2005 | Nikiforov et al. |
| 2005/0013737 A1 | 1/2005 | Chow et al. |
| 2005/0019902 A1 | 1/2005 | Mathies et al. |
| 2005/0037471 A1 | 2/2005 | Liu et al. |
| 2005/0041525 A1 | 2/2005 | Pugia et al. |
| 2005/0042639 A1 | 2/2005 | Knapp et al. |
| 2005/0048540 A1 | 3/2005 | Inami et al. |
| 2005/0058574 A1 | 3/2005 | Bysouth et al. |
| 2005/0058577 A1 | 3/2005 | Micklash et al. |
| 2005/0064535 A1 | 3/2005 | Favuzzi et al. |
| 2005/0069898 A1 | 3/2005 | Moon et al. |
| 2005/0084424 A1 | 4/2005 | Ganesan et al. |
| 2005/0106066 A1 | 5/2005 | Saltsman et al. |
| 2005/0112754 A1 | 5/2005 | Yoon et al. |
| 2005/0121324 A1 | 6/2005 | Park et al. |
| 2005/0129580 A1 | 6/2005 | Swinehart et al. |
| 2005/0130198 A1 | 6/2005 | Ammann et al. |
| 2005/0133370 A1 | 6/2005 | Park et al. |
| 2005/0135655 A1 | 6/2005 | Kopf-sill et al. |
| 2005/0142036 A1 | 6/2005 | Kim et al. |
| 2005/0158781 A1 | 7/2005 | Woudenberg et al. |
| 2005/0170362 A1 | 8/2005 | Wada et al. |
| 2005/0186585 A1 | 8/2005 | Juncosa et al. |
| 2005/0196321 A1 | 9/2005 | Huang |

(56) References Cited

U.S. PATENT DOCUMENTS

| | | |
|---|---|---|
| 2005/0202470 A1 | 9/2005 | Sundberg et al. |
| 2005/0202489 A1 | 9/2005 | Cho et al. |
| 2005/0202504 A1 | 9/2005 | Anderson et al. |
| 2005/0208676 A1 | 9/2005 | Kahatt |
| 2005/0214172 A1 | 9/2005 | Burgisser |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0238545 A1 | 10/2005 | Parce et al. |
| 2005/0239127 A1 | 10/2005 | Ammann et al. |
| 2005/0266489 A1 | 12/2005 | Ammann et al. |
| 2005/0276728 A1 | 12/2005 | Muller-Cohn et al. |
| 2006/0002817 A1 | 1/2006 | Bohm et al. |
| 2006/0003373 A1 | 1/2006 | Ammann et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0058519 A1 | 3/2006 | Deggerdal et al. |
| 2006/0062696 A1 | 3/2006 | Chow et al. |
| 2006/0094004 A1 | 5/2006 | Nakajima et al. |
| 2006/0094108 A1 | 5/2006 | Yoder et al. |
| 2006/0113190 A1 | 6/2006 | Kurnik |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |
| 2006/0154341 A1* | 7/2006 | Chen ............. B01L 7/52 435/91.2 |
| 2006/0165558 A1 | 7/2006 | Witty et al. |
| 2006/0165559 A1* | 7/2006 | Greenstein ....... G01N 35/00584 422/63 |
| 2006/0177376 A1 | 8/2006 | Tomalia et al. |
| 2006/0177855 A1 | 8/2006 | Utermohlen et al. |
| 2006/0183216 A1 | 8/2006 | Handique |
| 2006/0201887 A1 | 9/2006 | Siddiqi |
| 2006/0205085 A1 | 9/2006 | Handique |
| 2006/0207944 A1 | 9/2006 | Siddiqi |
| 2006/0210435 A1 | 9/2006 | Alavie et al. |
| 2006/0223169 A1 | 10/2006 | Bedingham et al. |
| 2006/0228734 A1 | 10/2006 | Vann et al. |
| 2006/0246493 A1 | 11/2006 | Jensen et al. |
| 2006/0246533 A1 | 11/2006 | Fathollahi et al. |
| 2006/0269641 A1 | 11/2006 | Atwood et al. |
| 2006/0269961 A1 | 11/2006 | Fukushima et al. |
| 2007/0004028 A1 | 1/2007 | Lair et al. |
| 2007/0009386 A1 | 1/2007 | Padmanabhan et al. |
| 2007/0020699 A1 | 1/2007 | Carpenter et al. |
| 2007/0020764 A1 | 1/2007 | Miller |
| 2007/0026421 A1 | 2/2007 | Sundberg et al. |
| 2007/0042441 A1 | 2/2007 | Masters et al. |
| 2007/0048188 A1 | 3/2007 | Bigus |
| 2007/0054413 A1 | 3/2007 | Aviles et al. |
| 2007/0077648 A1 | 4/2007 | Okamoto et al. |
| 2007/0092901 A1 | 4/2007 | Ligler et al. |
| 2007/0098600 A1 | 5/2007 | Kayyem et al. |
| 2007/0099200 A1 | 5/2007 | Chow et al. |
| 2007/0104617 A1 | 5/2007 | Coulling et al. |
| 2007/0116613 A1 | 5/2007 | Elsener |
| 2007/0154895 A1* | 7/2007 | Spaid ............. G01N 33/54366 435/6.19 |
| 2007/0177147 A1 | 8/2007 | Parce |
| 2007/0178607 A1 | 8/2007 | Prober et al. |
| 2007/0184463 A1 | 8/2007 | Molho et al. |
| 2007/0184547 A1 | 8/2007 | Handique et al. |
| 2007/0196237 A1 | 8/2007 | Neuzil et al. |
| 2007/0196238 A1 | 8/2007 | Kennedy et al. |
| 2007/0199821 A1 | 8/2007 | Chow |
| 2007/0215554 A1 | 9/2007 | Kreuwel et al. |
| 2007/0218459 A1 | 9/2007 | Miller et al. |
| 2007/0231213 A1 | 10/2007 | Prabhu et al. |
| 2007/0243626 A1 | 10/2007 | Windeyer et al. |
| 2007/0248958 A1 | 10/2007 | Jovanovich et al. |
| 2007/0261479 A1 | 11/2007 | Spaid et al. |
| 2007/0269861 A1 | 11/2007 | Williams et al. |
| 2007/0292941 A1 | 12/2007 | Handique et al. |
| 2008/0000774 A1 | 1/2008 | Park et al. |
| 2008/0003649 A1 | 1/2008 | Maltezos et al. |
| 2008/0017306 A1 | 1/2008 | Liu et al. |
| 2008/0056948 A1 | 3/2008 | Dale et al. |
| 2008/0069729 A1 | 3/2008 | McNeely |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |
| 2008/0176230 A1 | 7/2008 | Owen et al. |
| 2008/0192254 A1* | 8/2008 | Kim .................. G01N 21/645 356/436 |
| 2008/0226502 A1 | 9/2008 | Jonsmann et al. |
| 2008/0240898 A1 | 10/2008 | Manz et al. |
| 2008/0247914 A1 | 10/2008 | Edens et al. |
| 2008/0257882 A1 | 10/2008 | Turner |
| 2008/0280285 A1 | 11/2008 | Chen et al. |
| 2008/0308500 A1 | 12/2008 | Brassard |
| 2009/0047180 A1 | 2/2009 | Kawahara |
| 2009/0066339 A1 | 3/2009 | Glezer et al. |
| 2009/0136385 A1 | 5/2009 | Handique et al. |
| 2009/0148933 A1 | 6/2009 | Battrell et al. |
| 2009/0189089 A1 | 7/2009 | Bedingham et al. |
| 2009/0223925 A1 | 9/2009 | Morse et al. |
| 2009/0325164 A1 | 12/2009 | Vossenaar et al. |
| 2009/0325276 A1 | 12/2009 | Battrell et al. |
| 2010/0009351 A1 | 1/2010 | Brahmasandra et al. |
| 2010/0120129 A1 | 5/2010 | Amshey et al. |
| 2010/0233763 A1* | 9/2010 | Shigeura ............. G05D 23/192 435/91.2 |
| 2010/0284864 A1 | 11/2010 | Holenstein et al. |
| 2011/0008825 A1 | 1/2011 | Ingber et al. |
| 2011/0027151 A1 | 2/2011 | Handique et al. |
| 2011/0097493 A1 | 4/2011 | Kerr et al. |
| 2011/0127292 A1 | 6/2011 | Sarofim et al. |
| 2011/0158865 A1 | 6/2011 | Miller et al. |
| 2011/0287447 A1 | 11/2011 | Norderhaug |
| 2011/0300033 A1 | 12/2011 | Battisti |
| 2012/0122231 A1 | 5/2012 | Tajima |
| 2012/0160826 A1 | 6/2012 | Handique |
| 2012/0171678 A1 | 7/2012 | Maltezos et al. |
| 2012/0258463 A1 | 10/2012 | Duffy et al. |
| 2013/0183769 A1 | 7/2013 | Tajima |
| 2013/0217013 A1 | 8/2013 | Steel et al. |
| 2013/0315800 A1 | 11/2013 | Yin et al. |
| 2014/0030798 A1 | 1/2014 | Wu et al. |
| 2014/0227710 A1 | 8/2014 | Handique et al. |
| 2014/0329301 A1 | 11/2014 | Handique et al. |
| 2015/0045234 A1 | 2/2015 | Stone et al. |
| 2015/0064702 A1 | 3/2015 | Handique et al. |
| 2015/0174579 A1 | 6/2015 | Iten et al. |
| 2015/0315631 A1 | 11/2015 | Handique et al. |
| 2016/0038942 A1 | 2/2016 | Roberts |
| 2017/0275702 A1 | 9/2017 | Dahiya et al. |
| 2018/0112252 A1 | 4/2018 | Handique |
| 2018/0135102 A1 | 5/2018 | Gubatayao et al. |
| 2018/0154364 A1 | 6/2018 | Handique et al. |
| 2018/0333722 A1 | 11/2018 | Handique |
| 2019/0054467 A1 | 2/2019 | Handique |
| 2019/0054471 A1 | 2/2019 | Williams et al. |
| 2019/0144849 A1 | 5/2019 | Duffy et al. |
| 2019/0145546 A1 | 5/2019 | Handique |
| 2019/0151854 A1 | 5/2019 | Baum et al. |
| 2019/0154719 A1 | 5/2019 | LaChance et al. |
| 2019/0324050 A1 | 10/2019 | Williams et al. |
| 2019/0390255 A1 | 12/2019 | Wu et al. |
| 2020/0010872 A1 | 1/2020 | Ganesan et al. |
| 2020/0139363 A1 | 5/2020 | Handique et al. |
| 2020/0156059 A1 | 5/2020 | Handique et al. |
| 2020/0156060 A1 | 5/2020 | Handique et al. |
| 2020/0164363 A1 | 5/2020 | Handique et al. |
| 2020/0215536 A1 | 7/2020 | Handique et al. |
| 2020/0216831 A1 | 7/2020 | Brahmasandra et al. |

FOREIGN PATENT DOCUMENTS

| | | |
|---|---|---|
| AU | 4437602 | 7/2002 |
| AU | 4437702 | 7/2002 |
| AU | 764319 B2 | 8/2003 |
| CA | 2574107 | 9/1998 |

(56) References Cited

FOREIGN PATENT DOCUMENTS

| | | |
|---|---|---|
| CA | 2294819 | 1/1999 |
| CN | 1312287 C | 4/2007 |
| CN | 1942590 A | 4/2007 |
| CN | 1968754 A | 5/2007 |
| CN | 101466848 | 6/2009 |
| CN | 101522909 | 9/2009 |
| CN | 103540518 | 1/2014 |
| DE | 19929734 | 12/1999 |
| DE | 19833293 C1 | 1/2000 |
| EP | 0136126 A2 | 4/1985 |
| EP | 0365828 A2 | 5/1990 |
| EP | 0483620 A2 | 5/1992 |
| EP | 0688602 A2 | 12/1995 |
| EP | 0766256 | 4/1997 |
| EP | 0772494 B1 | 5/1997 |
| EP | 0810030 A1 | 12/1997 |
| EP | 1059458 A2 | 12/2000 |
| EP | 1064090 A1 | 1/2001 |
| EP | 1077086 A2 | 2/2001 |
| EP | 1346772 A2 | 9/2003 |
| EP | 1541237 A2 | 6/2005 |
| EP | 1574586 A2 | 9/2005 |
| EP | 1745153 | 1/2007 |
| EP | 1780290 A2 | 5/2007 |
| EP | 1792656 A1 | 6/2007 |
| EP | 2372367 A1 | 10/2011 |
| FR | 2672301 | 8/1992 |
| FR | 2795426 | 12/2000 |
| GB | 2453432 A | 4/2009 |
| JP | S50-100881 | 8/1975 |
| JP | 58212921 A | 12/1983 |
| JP | S62-119460 | 5/1987 |
| JP | H01-502319 | 8/1989 |
| JP | H 03181853 | 8/1991 |
| JP | 04-053555 U | 5/1992 |
| JP | 06-064156 U | 9/1994 |
| JP | 07-020010 | 1/1995 |
| JP | H07-290706 | 11/1995 |
| JP | H08-122336 | 5/1996 |
| JP | H08-173194 | 7/1996 |
| JP | H08-211071 | 8/1996 |
| JP | H08-285859 | 11/1996 |
| JP | H08-337116 | 12/1996 |
| JP | H09-304385 | 11/1997 |
| JP | H09-325151 | 12/1997 |
| JP | 2001-502790 | 1/1998 |
| JP | H01-219669 | 9/1998 |
| JP | H10-327515 | 12/1998 |
| JP | H11-009258 | 1/1999 |
| JP | H11-501504 | 2/1999 |
| JP | H11-503315 | 3/1999 |
| JP | 2000-514928 | 4/1999 |
| JP | H11-156231 | 6/1999 |
| JP | H11-316226 | 11/1999 |
| JP | H11-515106 | 12/1999 |
| JP | 2000-180455 | 6/2000 |
| JP | 2000-266760 | 9/2000 |
| JP | 2000-275255 | 10/2000 |
| JP | 2001-502319 | 2/2001 |
| JP | 2001-204462 | 7/2001 |
| JP | 2001-509437 | 7/2001 |
| JP | 3191150 B2 | 7/2001 |
| JP | 2001-515216 | 9/2001 |
| JP | 2001-523812 | 11/2001 |
| JP | 2001-527220 | 12/2001 |
| JP | 2002-503331 | 1/2002 |
| JP | 2002-085961 | 3/2002 |
| JP | 2002-517735 | 6/2002 |
| JP | 2002-215241 | 7/2002 |
| JP | 2002-540382 | 11/2002 |
| JP | 2002-544476 | 12/2002 |
| JP | 2003-500674 | 1/2003 |
| JP | 2003-047839 A | 2/2003 |
| JP | 2003-047840 A | 2/2003 |
| JP | 2003-516125 | 5/2003 |
| JP | 2003-164279 | 6/2003 |
| JP | 2003-185584 | 7/2003 |
| JP | 2003-299485 | 10/2003 |
| JP | 2003-329693 | 11/2003 |
| JP | 2003-329696 | 11/2003 |
| JP | 2003-532382 A | 11/2003 |
| JP | 2004-003989 | 1/2004 |
| JP | 2004-506179 A | 2/2004 |
| JP | 2004-150797 A | 5/2004 |
| JP | 2004-531360 A | 10/2004 |
| JP | 2004-533838 | 11/2004 |
| JP | 2004-361421 | 12/2004 |
| JP | 2004-536291 | 12/2004 |
| JP | 2004-536689 A | 12/2004 |
| JP | 2005-009870 | 1/2005 |
| JP | 2005-010179 | 1/2005 |
| JP | 2005-511264 | 4/2005 |
| JP | 2005-514718 | 5/2005 |
| JP | 2005-518825 | 6/2005 |
| JP | 2005-176613 A | 7/2005 |
| JP | 2005-192439 | 7/2005 |
| JP | 2005-192554 | 7/2005 |
| JP | 2005-519751 | 7/2005 |
| JP | 2005-204661 | 8/2005 |
| JP | 2005-525816 | 9/2005 |
| JP | 2005-291954 A | 10/2005 |
| JP | 2005-532043 | 10/2005 |
| JP | 2005-323519 | 11/2005 |
| JP | 2005-533652 | 11/2005 |
| JP | 2005-535904 | 11/2005 |
| JP | 2006-021156 A | 1/2006 |
| JP | 2006-055837 A | 3/2006 |
| JP | 2006-094866 A | 4/2006 |
| JP | 2006-145458 | 6/2006 |
| JP | 2006-167569 | 6/2006 |
| JP | 2006-284409 | 10/2006 |
| JP | 2007-024742 A | 2/2007 |
| JP | 2007-074960 | 3/2007 |
| JP | 2007-097477 | 4/2007 |
| JP | 2007-101364 | 4/2007 |
| JP | 2007-510518 | 4/2007 |
| JP | 2007-514405 A | 6/2007 |
| JP | 2007-178328 | 7/2007 |
| JP | 2007-535933 | 12/2007 |
| JP | 2009-515140 | 4/2009 |
| JP | 2009-542207 | 12/2009 |
| JP | 3193848 U | 10/2014 |
| KR | 1020060044489 A | 5/2006 |
| RU | 2418633 C2 | 5/2011 |
| WO | WO 1988/006633 | 9/1988 |
| WO | WO 1990/012350 | 10/1990 |
| WO | WO 1992/005443 | 4/1992 |
| WO | WO 1994/005414 | 3/1994 |
| WO | WO 1994/011103 | 5/1994 |
| WO | WO 1996/004547 | 2/1996 |
| WO | WO 1996/018731 | 6/1996 |
| WO | WO 1996/039547 | 12/1996 |
| WO | WO 1997/005492 | 2/1997 |
| WO | WO 1997/016835 | 5/1997 |
| WO | WO 1997/021090 | 6/1997 |
| WO | WO 1997/027324 | 7/1997 |
| WO | WO 1998/000231 | 1/1998 |
| WO | WO 1998/022625 | 5/1998 |
| WO | WO 1998/035013 | 8/1998 |
| WO | WO 1998/038487 | 9/1998 |
| WO | WO 1998/049548 | 11/1998 |
| WO | WO 1998/050147 | 11/1998 |
| WO | WO 1998/053311 | 11/1998 |
| WO | WO 1999/001688 | 1/1999 |
| WO | WO 1999/009042 | 2/1999 |
| WO | WO 1999/012016 | 3/1999 |
| WO | WO 1999/017093 | 4/1999 |
| WO | WO 1999/029703 | 6/1999 |
| WO | WO 1999/033559 | 7/1999 |
| WO | WO 2000/022436 | 4/2000 |
| WO | WO 2000/075623 | 12/2000 |
| WO | WO 2000/078455 | 12/2000 |
| WO | WO 2001/005510 | 1/2001 |
| WO | WO 2001/014931 | 3/2001 |

(56) References Cited

FOREIGN PATENT DOCUMENTS

| | | |
|---|---|---|
| WO | WO 2001/027614 | 4/2001 |
| WO | WO 2001/028684 | 4/2001 |
| WO | WO 2001/030995 | 5/2001 |
| WO | WO 2001/041931 | 6/2001 |
| WO | WO 2001/046474 | 6/2001 |
| WO | WO 2001/054813 | 8/2001 |
| WO | WO 2001/089681 | 11/2001 |
| WO | WO 2001/089705 | 11/2001 |
| WO | WO 2002/048164 | 6/2002 |
| WO | WO 2002/072264 | 9/2002 |
| WO | WO 2002/078845 | 10/2002 |
| WO | WO 2002/086454 | 10/2002 |
| WO | WO 2003/007677 | 1/2003 |
| WO | WO 2003/012325 | 2/2003 |
| WO | WO 2003/012406 | 2/2003 |
| WO | WO 2003/048295 | 6/2003 |
| WO | WO 2003/055605 | 7/2003 |
| WO | WO 2003/076661 | 9/2003 |
| WO | WO 2003/078065 | 9/2003 |
| WO | WO 2003/080868 | 10/2003 |
| WO | WO 2003/087410 | 10/2003 |
| WO | WO 2004/007081 | 1/2004 |
| WO | WO 2004/010760 | 2/2004 |
| WO | WO 2004/048545 | 6/2004 |
| WO | WO 2004/055522 | 7/2004 |
| WO | WO 2004/056485 | 7/2004 |
| WO | WO 2004/074848 | 9/2004 |
| WO | WO 2004/094986 | 11/2004 |
| WO | WO 2005/008255 | 1/2005 |
| WO | WO 2005/011867 | 2/2005 |
| WO | WO 2005/030984 | 4/2005 |
| WO | WO 2005/072353 | 8/2005 |
| WO | WO 2005/094981 | 10/2005 |
| WO | WO 2005/107947 | 11/2005 |
| WO | WO 2005/108571 | 11/2005 |
| WO | WO 2005/108620 | 11/2005 |
| WO | WO 2005/116202 | 12/2005 |
| WO | WO 2005/118867 | 12/2005 |
| WO | WO 2005/120710 | 12/2005 |
| WO | WO 2006/010584 | 2/2006 |
| WO | WO 2006/032044 | 3/2006 |
| WO | WO 2006/035800 | 4/2006 |
| WO | WO 2006/043642 | 4/2006 |
| WO | WO 2006/066001 | 6/2006 |
| WO | WO 2006/079082 | 7/2006 |
| WO | WO 2006/081995 | 8/2006 |
| WO | WO 2006/113198 | 10/2006 |
| WO | WO 2006/118420 | 11/2006 |
| WO | WO 2006/119280 | 11/2006 |
| WO | WO 2007/044917 | 4/2007 |
| WO | WO 2007/050327 | 5/2007 |
| WO | WO 2007/064117 | 6/2007 |
| WO | WO 2007/075919 | 7/2007 |
| WO | WO 2007/091530 | 8/2007 |
| WO | WO 2007/112114 | 10/2007 |
| WO | WO 2007/120240 | 10/2007 |
| WO | WO 2007/120241 | 10/2007 |
| WO | WO 2008/005321 | 1/2008 |
| WO | WO 2008/030914 | 3/2008 |
| WO | WO 2008/060604 | 5/2008 |
| WO | WO 2008/149282 | 12/2008 |
| WO | WO 2009/012185 | 1/2009 |
| WO | WO 2009/054870 | 4/2009 |
| WO | WO 2010/118541 | 10/2010 |
| WO | WO 2010/130310 | 11/2010 |
| WO | WO 2010/140680 | 12/2010 |
| WO | WO 2011/009073 | 1/2011 |
| WO | WO 2011/101467 | 8/2011 |

OTHER PUBLICATIONS

Becker H., "Hype, hope and hubris: the quest for the killer application in microfluidics", Lab on a Chip, The Royal Society of Chemistry (2009) 9:2119-2122.

Becker H., "Collective Wisdom", Lab on a Chip, The Royal Society of Chemistry (2010) 10:1351-1354.
Bollet, C. et al., "A simple method for the isolation of chromosomal DNA from Gram positive or acid-fast bacteria", Nucleic Acids Research, vol. 19, No. 8 (1991), p. 1955.
Brahmasandra et al., On-chip DNA detection in microfabricated separation systems, SPIE Conference on Microfluidic Devices and Systems, 1998, vol. 3515, pp. 242-251, Santa Clara, CA.
Breadmore, M.C. et al., "Microchip-Based Purification of DNA from Biological Samples", Anal. Chem., vol. 75 (2003), pp. 1880-1886.
Brody, et al., Diffusion-Based Extraction in a Microfabricated Device, Sensors and Actuators Elsevier, 1997, vol. A58, No. 1, pp. 13-18.
Broyles et al., "Sample Filtration, Concentration, and Separation Integrated on Microfluidic Devices" Analytical Chemistry (American Chemical Society), (2003) 75(11): 2761-2767.
Burns et al., "An Integrated Nanoliter DNA Analysis Device", Science 282:484-487 (1998).
Chang-Yen et al., "Design, fabrication, and packaging of a practical multianalyte-capable optical biosensor," J Microlith Microfab Microsyst. (2006) 5(2):021105 in 8 pages.
Chaudhari et al., "Transient Liquid Crystal Thermometry of Microfabricated PCR Vessel Arrays", J Microelectro Sys., (1998) 7(4):345-355.
Chen et al., "Total nucleic acid analysis integrated on microfluidic devices," Lab on a Chip. (2007) 7:1413-1423.
Chung, Y. et al., "Microfluidic chip for high efficiency DNA extraction", Miniaturisation for Chemistry, Biology & Bioengineering, vol. 4, No. 2 (Apr. 2004), pp. 141-147.
Cooley et al., "Applications of Ink-Jet Printing Technology to BioMEMS and Microfluidic Systems", Proceedings, SPIE Conference on Microfluids and BioMEMS, (Oct. 2001), 12 pages.
Cui et al., "Design and Experiment of Silicon PCR Chips," Proc. SPIE 4755, Design, Test, Integration, and Packaging of MEMS/MOEMS 2002, (Apr. 19, 2002) pp. 71-76.
Edwards, "Silicon (Si)," in "Handbook of Optical Constants of Solids" (Ghosh & Palik eds., 1997) in 24 pages.
European Extended Search Report dated Feb. 16, 2017 for Application No. EP 16191793.5, filed Sep. 30, 2016.
European Extended Search Report dated May 11, 2017 for Application No. EP 16191787.7, filed Sep. 30, 2016.
Goldmeyer et al., "Identification of *Staphylococcus aureus* and Determination of Methicillin Resistance Directly from Positive Blood Cultures by Isothermal Amplification and a Disposable Detection Device", J Clin Microbiol. (Apr. 2008) 46(4): 1534-1536.
Grunenwald H., "Optimization of Polymerase Chain Reactions," in Methods in Molecular Biology, PCR Protocols., Second Edition by Bartlett et al. [Eds.] Humana Press (2003) vol. 226, pp. 89-99.
Hale et al., "Optical constants of Water in the 200-nm to 200- μm Wavelength Region", Applied Optics, 12(3): 555-563 (1973).
Handal et al., "DNA mutation detection and analysis using miniaturized microfluidic systems", Expert Rev Mol Diagn. (2006) 6(1):29-38.
Handique et al, "Microfluidic flow control using selective hydrophobic patterning", SPIE, (1997) 3224: 185-194.
Handique et al., "On-Chip Thermopneumatic Pressure for Discrete Drop Pumping", Anal. Chem., (2001) 73(8):1831-1838.
Handique et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.
Handique et al., "Mathematical Modeling of Drop Mixing in a Slit-Type Microchannel", J. Micromech. Microeng., 11:548-554 (2001).
Handique et al., "Nanoliter Liquid Metering in Microchannels Using Hydrophobic Patterns", Anal. Chem., 72(17):4100-4109 (2000).
Harding et al., "DNA isolation using Methidium-Spermine-Sepharose", Meth Enzymol. (1992) 216: 29-39.
Harding et al., "Rapid isolation of DNA from complex biological samples using a novel capture reagent—methidium-spermine-sepharose", Nucl Acids Res. (1989) 17(17): 6947-6958.

(56) References Cited

OTHER PUBLICATIONS

He et al., Microfabricated Filters for Microfluidic Analytical Systems, Analytical Chemistry, American Chemical Society, 1999, vol. 71, No. 7, pp. 1464-1468.
Ibrahim, et al., Real-Time Microchip PCR for Detecting Single-Base Differences in Viral and Human DNA, Analytical Chemistry, American Chemical Society, 1998, 70(9): 2013-2017.
International Preliminary Report on Patentability and Written Opinion dated Jan. 19, 2010 for Application No. PCT/US2008/008640, filed Jul. 14, 2008.
International Preliminary Report on Patentability dated Jan. 19, 2010 for Application No. PCT/US2008/069897, filed Jul. 11, 2008.
International Search Report and Written Opinion dated Apr. 4, 2008 for PCT/US2007/007513, filed Mar. 26, 2007.
International Search Report and Written Opinion dated Jan. 5, 2009 for PCT/US2007/024022, filed Nov. 14, 2007.
International Search Report and Written Opinion, dated Oct. 3, 2008, issued in International Application No. PCT/US2008/069897, filed Jul. 11, 2008.
International Search Report dated Jun. 17, 2009 for Application No. PCT/US2008/008640, filed Jul. 14, 2008.
Irawan et al., "Cross-Talk Problem on a Fluorescence Multi-Channel Microfluidic Chip System," Biomed Micro. (2005) 7(3):205-211.
Khandurina et al., Microfabricated Porous Membrane Structure for Sample Concentration and Electrophoretic Analysis, Analytical Chemistry American Chemical Society, 1999, 71(9): 1815-1819.
Khandurina et al., "Bioanalysis in microfluidic devices," J Chromatography A, (2002) 943:159-183.
Kim et al., "Electrohydrodynamic Generation and Delivery of Monodisperse Picoliter Droplets Using a Poly(dimethylsiloxane) Microchip", Anal Chem. (2006) 78: 8011-8019.
Kopp et al., Chemical Amplification: Continuous-Flow PCR on a Chip, www.sciencemag.org, 1998, vol. 280, pp. 1046-1048.
Kuo et al., "Remnant cationic dendrimers block RNA migration in electrophoresis after monophasic lysis", J Biotech. (2007) 129: 383-390.
Kutter et al., Solid Phase Extraction on Microfluidic Devices, J. Microcolumn Separations, John Wiley & Sons, Inc., 2000, 12(2): 93-97.
Labchem; Sodium Hydroxide, 0,5N (0.5M); Safety Data Sheet, 2015; 8 pages.
Liao et al., "Miniature RT-PCR system for diagnosis of RNA-based viruses," Nucl Acids Res. (2005) 33(18):e156 in 7 pages.
Lin et al., "Thermal Uniformity of 12-in Silicon Wafer During Rapid Thermal Processing by Inverse Heat Transfer Method," IEEE Transactions on Semiconductor Manufacturing, (2000) 13(4):448-456.
Livache et al., "Polypyrrole DNA chip on a Silicon Device: Example of Hepatitis C Virus Genotyping", Analytical Biochemistry, (1998) 255: 188-194.
Malitson, "Interspecimen Comparison of the Refractive Index of Fused Silica," J Optical Society of America, 55:1205-1209 (1965).
Manz et al., "Miniaturized Total Chemical Analysis Systems: a Novel Concept for Chemical Sensing," Sensors and Actuators B1, (1990) 244-248.
Mastrangelo et al., Microfabricated Devices for Genetic Diagnostics. Proceedings of the IEEE (1998) 86(8):1769-1787.
Mascini et al., "DNA electrochemical biosensors", Fresenius J. Anal. Chem., 369: 15-22, (2001).
Meyers, R.A., Molecular Biology and Biotechnology: A Comprehensive Desk Reference; VCH Publishers, Inc. New York, NY; (1995) pp. 418-419.
Minco, "Conductive Heating Technologies for Medical Diagnostic Equipment," (2006) in 13 pages.
Nakagawa et al., Fabrication of amino silane-coated microchip for DNA extraction from whole blood, J of Biotechnology, Mar. 2, 2005, 116: 105-111.
Northrup et al., A Miniature Analytical Instrument for Nucleic Acids Based on Micromachined Silicon Reaction Chambers, Analytical Chemistry, American Chemical Society, 1998, 70(5): 918-922.
Oh K.W. et al., "A Review of Microvalves", J Micromech Microeng. (2006) 16:R13-R39.
Oleschuk et al., Trapping of Bead-Based Reagents within Microfluidic Systems: On-Chip Solid-Phase Extraction and Electrochromatography, Analytical Chemistry, American Chemical Society, 2000, 72(3): 585-590.
Pal et al., "Phase Change Microvalve for Integrated Devices," Anal. Chem. (2004), 76(13):3740-3748, Jul. 1, 2004, in 9 pages.
Palina et al., "Laser Assisted Boron Doping of Silicon Wafer Solar Cells Using Nanosecond and Picosecond Laser Pulses," 2011 37th IEEE Photovoltaic Specialists Conference, pp. 002193-002197, IEEE (2011).
Paulson et al., "Optical dispersion control in surfactant-free DNA thin films by vitamin B2 doping," Nature, Scientific Reports 8:9358 (2018) published at www.nature.com/scientificreports, Jun. 19, 2018.
Picard et al., Laboratory Detection of Group B *Streptococcus* for Prevention of Perinatal Disease, Eur. J. Clin. Microbiol. Infect. Dis., Jul. 16, 2004, 23: 665-671.
Plambeck et al., "Electrochemical Studies of Antitumor Antibiotics", J. Electrochem Soc.: Electrochemical Science and Technology (1984), 131(11): 2556-2563.
Roche et al. "Ectodermal commitment of insulin-producing cells derived from mouse embryonic stem cells" Faseb J (2005) 19: 1341-1343.
Rohsenow et al. [Eds.], Handbook of Heat Transfer, 3rd Edition McGraw-Hill Publishers (1998) Chapters 1 & 3; pp. 108.
Ross et al., Analysis of DNA Fragments from Conventional and Microfabricated PCR Devices Using Delayed Extraction MALDI-TOF Mass Spectrometry, Analytical Chemistry, American Chemical Society, 1998, 70(10): 2067-2073.
Sanchez et al., "Linear-After-The-Exponential (LATE)-PCR: An advanced method of asymmetric PCR and its uses in quantitative real-time analysis", PNAS (2004) 101(7): 1933-1938.
Shen et al., "A microchip-based PCR device using flexible printed circuit technology," Sensors and Actuators B (2005), 105:251-258.
Shoffner et al., Chip PCR.I. Surface Passivation of Microfabricated Silicon-Glass Chips for PCR, Nucleic Acids Research, Oxford University Press, (1996) 24(2): 375-379.
Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.
Spitzack et al., "Polymerase Chain Reaction in Miniaturized Systems: Big Progress in Little Devices", in Methods in Molecular Biology—Microfluidic Techniques, Minteer S.D. [Ed.] Humana Press (2006), Chapter 10, pp. 97-129.
Supplementary European Search dated Jan. 10, 2008 for European Patent Application No. 05745564, filed May 3, 2005.
Supplementary European Search Report dated Jun. 3, 2005 for European Patent Application No. 02723636.3, filed Mar. 27, 2002.
Velten et al., "Packaging of Bio-MEMS: Strategies, Technologies, and Applications," IEEE Transactions on Advanced Packaging, (2005) 28(4):533-546.
Wang, "Survey and Summary, from DNA Biosensors to Gene Chips", Nucleic Acids Research, 28(16):3011-3016, (2000).
Waters et al., Microchip Device for Cell Lysis, Multiplex PCR Amplification, and Electrophoretic Sizing, Analytical Chemistry, American Chemical Society, 1998, 70(1): 158-162.
Weigl, et al., Microfluidic Diffusion-Based Separation and Detection, www.sciencemag.org, 1999, vol. 283, pp. 346-347.
Written Opinion (Rule 66) dated Oct. 24, 2013 for Application No. PCT/US2012/063091, filed Nov. 1, 2012.
Wu et al., "Polycationic dendrimers interact with RNA molecules: polyamine dendrimers inhibit the catalytic activity of Candida ribozymes", Chem Commun. (2005) 3: 313-315.
Yoza et al., "Fully Automated DNA Extraction from Blood Using Magnetic Particles Modified with a Hyperbranched Polyamidoamine Dendrimer", J Biosci Bioeng, 2003, 95(1): 21-26.

(56) References Cited

OTHER PUBLICATIONS

Yoza et al., DNA extraction using bacterial magnetic particles modified with hyperbranched polyamidoamine dendrimer, J Biotechnol., Mar. 20, 2003, 101(3): 219-228.
Zhang et al., "PCR Microfluidic Devices for DNA Amplification," Biotechnology Advances, 24:243-284 (2006).
Zhang et al., "Miniaturized PCR chips for nucleic acid amplification and analysis: latest advances and future trends," Nucl Acids Res., (2007) 35(13):4223-4237.
Zhou et al., "Cooperative binding and self-assembling behavior of cationic low molecular-weight dendrons with RNA molecules", Org Biomol Chem. (2006) 4(3): 581-585.
Zhou et al., "PAMAM dendrimers for efficient siRNA delivery and potent gene silencing", Chem Comm.(Camb.) (2006) 22: 2362-2364.
Zou et al., "A Micromachined Integratable Thermal Reactor," technical digest from International Electron Devices Meeting, IEEE, Washington, D.C., Dec. 2-5, 2001 (6 pages).
Petition for Inter Partes Review of U.S. Pat. No. 7,998,708 (Paper 1 in IPR2019-00488) dated Dec. 20, 2018 (94 pages).
Declaration of Bruce K. Gale, Ph.D. (Exhibit 1001 in IPR2019-00488 and IPR2019-00490) dated Dec. 20, 2018 (235 pages).
Patent Owner Preliminary Response to Petition for Inter Partes Review of U.S. Pat. No. 7,998,708 and Exhibit List (Papers 5 and 6 in IPR2019-00488) dated Apr. 18, 2019 (79 pages).
Decision instituting Inter Partes Review of U.S. Pat. No. 7,998,708 (Paper 8 in IPR2019-00488) dated Jul. 16, 2019 (20 pages).
Petition for Inter Partes Review of U.S. Pat. No. 8,323,900 (Paper 1 in IPR201900490) dated Dec. 20, 2018 (85 pages).
Declaration of Michael G. Mauk, Ph.D. In Support of Patent Owner Preliminary Responses in IPR2019-00488 and IPR2019-00490 dated Apr. 18, 2019 (43 pages).
Patent Owner Preliminary Response to Petition for Inter Partes Review of U.S. Pat. No. 8,323,900 and Exhibit List (Papers 5 and 6 in IPR2019-00490) dated Apr. 18, 2019 (73 pages).
Decision instituting Inter Partes Review of U.S. Pat. No. 8,323,900 (Paper 8 in IPR2019-00490) dated Jul. 16, 2019 (23 pages).
Patent Owner's Response in Inter Partes Review of U.S. Pat. No. 8,323,900 and Exhibit List (Paper 25 in IPR2019-00490) dated Oct. 16, 2019 (80 pages).
Patent Owner's Response in Inter Partes Review of U.S. Pat. No. 7,998,708 and Exhibit List (Paper 25 in IPR 2019-00488) dated Oct. 16, 2019 (93 pages).
Transcript of Deposition of Bruce K. Gale, Ph.D., in Support of Patent Owner's Responses (Exhibit 2012 in IPR2019-00488 and IPR2019-00490), taken Sep. 24, 2019 (124 pages).
Declaration of M. Allen Northrup, Ph.D. in Support of Patent Owner's Responses (Exhibit 2036 in IPR2019-00488 and IPR2019-00490) dated Oct. 16, 2019 (365 pages).
Complaint filed by *Becton, Dickinson et al.*, v. *NeuModx Molecular, Inc.* on Jun. 18, 2019 in U.S. District Court, Delaware, Case #1:19-cv-01126-LPS, Infringement Action involving U.S. Pat. No. 7,998,708; 8,273,308; 8,323,900; 8,415,103; 8,703,069; and 8,709,787 (29 pages).
Answer to Complaint filed by NeuModx Molecular, Inc. on Aug. 9, 2019 in U.S. District Court, Delaware, Case #1:19-cv-01126-LPS (24 pages).
Amended Answer to Complaint filed by NeuModx Molecular, Inc. on Oct. 4, 2019 in U.S. District Court, Delaware, Case #1:19-cv-01126-LPS (31 pages).
Altet et al., [Eds.] "Thermal Transfer and Thermal Coupling in IC's", Thermal Testing of Integrated Circuits; Chapter 2 (2002) Springer Science pp. 23-51.
Ateya et al., "The good, the bad, and the tiny: a review of microflow cytometry", Anal Bioanal Chem. (2008) 391(5):1485-1498.
Auroux et al., "Miniaturised nucleic acid analysis", Lab Chip. (2004) 4(6):534-546.
Baechi et al., "High-density microvalve arrays for sample processing in PCR chips", Biomed Microdevices. (2001) 3(3):183-190.

Baker M., "Clever PCR: more genotyping, smaller volumes." Nature Methods (May 2010) 70(5):351-356.
Becker H. "Fabrication of Polymer Microfluidic Devices", in Biochip Technology (2001), Chapter 4, pp. 63-96.
Becker, H., "Microfluidic Devices Fabricated by Polymer Hot Embossing," in Integrated Microfabricated Biodevices: Advanced Technologies for Genomics, Drug Discovery, Bioanalysis, and Clinical Diagnostics (2002), Chapter 13, 32 pages.
Becker H., "Microfluidics: A Technology Coming of Age", Med Device Technol. (2008) 19(3):21-24.
Becker et al., "Portable CE system with contactless conductivity detection in an injection molded polymer chip for on-site food analysis", SPIE Proceedings MOEMS-MEMS 2008 Micro and Nanofabrication (2008) vol. 6886 in 8 pages.
Belgrader et al., "Rapid PCR for Identity Testing Using a Battery-Powered Miniature Thermal Cycler", J Forensic Sci. (1998) 43(2):315-319.
Belgrader et al., "A minisonicator to rapidly disrupt bacterial spores for DNA analysis.", Anal Chem. (1999) 71(19):4232-4236.
Belgrader et al., "Real-time PCR Analysis on Nucleic Acids Purified from Plasma Using a Silicon Chip", Micro Total Analysis Systems 2000 (pp. 525-528). Springer, Dordrecht.
Belgrader et al., "A microfluidic cartridge to prepare spores for PCR analysis", Biosens Bioelectron. (2000) 14(10-11):849-852.
Belgrader et al., "A Battery-Powered Notebook Thermal Cycler for Rapid Multiplex Real-Time PCR Analysis", Anal Chem. (2001) 73(2):286-289.
Belgrader et al., "Rapid and Automated Cartridge-based Extraction of Leukocytes from Whole Blood for Microsatellite DNA Analysis by Capillary Electrophoresis", Clin Chem. (2001) 47(10):1917-1933.
Belgrader et al., "A Rapid, Flow-through, DNA Extraction Module for Integration into Microfluidic Systems", Micro Total Analysis Systems (2002) pp. 697-699). Springer, Dordrecht.
Belgrader et al., "Development of a Battery-Powered Portable Instrumentation for Rapid PCR Analysis", in Integrated Microfabicated Devices, (2002) Ch. 8, pp. 183-206, CRC Press.
Bell M., "Integrated Microsystems in Clinical Chemistry", in Integrated Microfabicated Devices, (2002) Ch. 16, pp. 415-435, CRC Press.
Berthier et al., "Managing evaporation for more robust microscale assays Part 1. Volume loss in high throughput assays", Lab Chip (2008) 8(6):852-859.
Berthier et al., "Managing evaporation for more robust microscale assays Part 2. Characterization of convection and diffusion for cell biology", Lab Chip (2008) 8(6):860-864.
Berthier et al., "Microdrops," in Microfluidics for Biotechnology (2006), Chapter 2, pp. 51-88.
Biomerieux Press Release: "bioMérieux—2018 Financial Results," dated Feb. 27, 2019, accessed at www.biomerieux.com, pp. 13.
Blanchard et al., "Micro structure mechanical failure characterization using rotating Couette flow in a small gap", J Micromech Microengin. (2005) 15(4):792-801.
Blanchard et al., "Single-disk and double-disk viscous micropumps", Sensors and Actuators A (2005) 122:149-158.
Blanchard et al., "Performance and Development of a Miniature Rotary Shaft Pump", J Fluids Eng. (2005) 127(4):752-760.
Blanchard et al., "Single-disk and double-disk viscous micropump", ASME 2004 Inter'l Mechanical Engineering Congress & Exposition, Nov. 13-20, 2004, Anaheim, CA, IMECE2004-61705:411-417.
Blanchard et al., "Miniature Single-Disk Viscous Pump (Single-DVP), Performance Characterization", J Fluids Eng. (2006) 128(3):602-610.
Brahmasandra et al., "Microfabricated Devices for Integrated DNA Analysis", in Biochip Technology by Cheng et al., [Eds.] (2001) pp. 229-250.
Bu et al., "Design and theoretical evaluation of a novel microfluidic device to be used for PCR", J Micromech Microengin. (2003) 13(4):S125-S130.
Cady et al., "Real-time PCR detection of Listeria monocytogenes using an integrated microfluidics platform", Sensors Actuat B. (2005) 107:332-341.

(56) References Cited

OTHER PUBLICATIONS

Carlen et al., "Paraffin Actuated Surface Micromachined Valve," in IEEE MEMS 2000 Conference, Miyazaki, Japan, (Jan. 2000) pp. 381-385.
Carles et al., "Polymerase Chain Reaction on Microchips" in Methods in Molecular Biology—Microfluidic Techniques, Reviews & Protocols by Minteer S.D. [Ed.] Humana Press (2006), vol. 321; Chapter 11, pp. 131-140.
Chang-Yen et al., "A novel integrated optical dissolved oxygen sensor for cell culture and micro total analysis systems", IEEE Technical Digest MEMS International Conference Jan. 24, 2002, 4 pages.
Chang-Yen et al., "A PDMS microfluidic spotter for fabrication of lipid microarrays", IEEE 3rd EMBS Special Topic Conference May 12-15, 2005; 2 pages.
Chang-Yen et al., "Design and fabrication of a multianalyte-capable optical biosensor using a multiphysics approach", IEEE 3rd EMBS Special Topic Conference May 12-15, 2005; 2 pages.
Chang-Yen et al., "A Novel PDMS Microfluidic Spotter for Fabrication of Protein Chips and Microarrays", IEEE J of Microelectromech Sys. (2006) 15(5): 1145-1151.
Chang-Yen et al., "Spin-assembled nanofilms for gaseous oxygen sensing." Sens Actuators B: Chemical (2007), 120(2):426-433.
Chen P-C., "Accelerating micro-scale PCR (polymerase chain reactor) for modular lab-on-a-chip system", LSU Master's Theses—Digital Commons, (2006) 111 pages.
Cheng et al., "Biochip-Based Portable Laboratory", Biochip Tech. (2001):296-289.
Cho et al., "A facility for characterizing the steady-state and dynamic thermal performance of microelectromechanical system thermal switches", Rev Sci Instrum. (2008) 79(3):034901-1 to -8.
Chong et al., "Disposable Polydimethylsioxane Package for 'Bio-Microfluidic System'", IEEE Proceedings Electronic Components and Technology (2005); 5 pages.
Chou et al., "A miniaturized cyclic PCR device—modeling and experiments", Microelec Eng. (2002) 61-62:921-925.
Christel et al., "Nucleic Acid Concentration and PCR for Diagnostic Applications", in Micro Total Analysis Systems. (1998) D.J. Harrison et al. [Eds.] pp. 277-280.
Christel et al., "Rapid, Automated Nucleic Acid Probe Assays Using Silicon Microstructures for Nucleic Acid Concentration", J Biomech Eng. (1999) 121(1):22-27.
Christensen et al., "Characterization of interconnects used in PDMS microfluidic systems", J Micromech Microeng. (2005) 15:928 in 8 pages.
Crews et al, "Rapid Prototyping of a Continuous-Flow PCR Microchip", Proceedings of the AiChE Annual Meeting(Nov. 15, 2006) (335a) 3 pages.
Crews et al., Thermal gradient PCR in a continuous-flow microchip. In Microfluidics, BioMEMS, and Medical Microsystems V; Jan. 2007; vol. 6465, p. 646504; 12 pages.
Crews et al., "Continuous-flow thermal gradient PCR", Biomed Microdevices. (2008) 10(2):187-195.
Cui et al., "Electrothermal modeling of silicon PCR chips", In MEMS Design, Fabrication, Characterization, and Packaging, (Apr. 2001) (vol. 4407, pp. 275-280.
Danaher Press Release: "Danaher to Acquire Cepheid for $53.00 per share, or approximately $4 Billion," dated Sep. 6, 2016, accessed at www.danaher.com, pp. 3.
Demchenko A.P., "The problem of self-calibration of fluorescence signal in microscale sensor systems", Lab Chip. (2005) 5(11):1210-1223.
Dineva et al., "Sample preparation: a challenge in the development of point-of-care nucleic acid-based assays for resource-limited settings", Analyst. (2007) 132(12):1193-1199.
Dishinger et al., "Multiplexed Detection and Applications for Separations on Parallel Microchips", Electophoresis. (2008) 29(16):3296-3305.

Dittrich et al., "Single-molecule fluorescence detection in microfluidic channels—the Holy Grail in muTAS?", Anal Bioanal Chem. (2005) 382(8):1771-1782.
Dittrich et al., "Lab-on-a-chip: microfluidics in drug discovery", Nat Rev Drug Discov. (2006) 5(3):210-208.
Dunnington et al., "Approaches to Miniaturized High-Throughput Screening of Chemical Libraries", in Integrated Microfabicated Devices, (2002) Ch. 15, pp. 371-414, CRC Press.
Eddings et al., "A PDMS-based gas permeation pump for on-chip fluid handling in microfluidic devices", J Micromech Microengin. (2006) 16(11):2396-2402.
Edwards et al., "Micro Scale Purification Systems for Biological Sample Preparation", Biomed Microdevices (2001) 3(3):211-218.
Edwards et al., "A microfabricated thermal field-flow fractionation system", Anal Chem. (2002) 74(6):1211-1216.
Ehrlich et al., "Microfluidic devices for DNA analysis", Trends Biotechnol. (1999) 17(8):315-319.
El-Ali et al., "Simulation and experimental validation of a SU-8 based PCR thermocycler chip with integrated heaters and temperature sensor", Sens Actuators A: Physical (2004) 110(1-3):3-10.
Erickson et al., "Joule heating and heat transfer in poly(dimethylsiloxane) microfluidic systems", Lab Chip (2003) 3(3):141-149.
Erickson et al., "Integrated Microfluidic Devices", Analytica Chim Acta. (2004) 507:11-26.
Erill et al., "Development of a CMOS-compatible PCR chip: comparison of design and system strategies", J Micromech Microengin. (2004) 14(11):1-11.
Fair R.B., Digital microfluidics: is a true lab-on-a-chip possible? Microfluidics Nanofluid. (2007) 3:245-281.
Fan et al., "Integrated Plastic Microfluidic Devices for Bacterial Detection", in Integrated Biochips for DNA Analysis by Liu et al. [Eds], (2007) Chapter 6, pp. 78-89.
Fiorini et al., "Disposable microfluidic devices: fabrication, function, and application", Biotechniques (2005) 38(3):429-446.
Frazier et al., "Integrated micromachined components for biological analysis systems", J Micromech. (2000) 1(1):67-83.
Gale et al., "Micromachined electrical field-flow fractionation (mu-EFFF) system", IEEE Trans Biomed Eng. (1998) 45(12):1459-1469.
Gale et al., "Geometric scaling effects in electrical field flow fractionation. 1. Theoretical analysis", Anal Chem. (2001) 73(10):2345-2352.
Gale et al., "BioMEMS Education at Louisiana Tech University", Biomed Microdevices, (2002) 4:223-230.
Gale et al., "Geometric scaling effects in electrical field flow fractionation. 2. Experimental results", Anal Chem. (2002) 74(5):1024-1030.
Gale et al., "Cyclical electrical field flow fractionation", Electrophoresis. (2005) 26(9):1623-1632.
Gale et al., "Low-Cost MEMS Technologies", Elsevier B.V. (2008), Chapter 1.12; pp. 342-372.
Garst et al., "Fabrication of Multilayered Microfluidic 3D Polymer Packages", IEEE Proceedings Electronic Components & Tech, Conference May/Jun. 2005, pp. 603-610.
Gärtner et al., "Methods and instruments for continuous-flow PCR on a chip", Proc. SPIE 6465, Microfluidics, BioMEMS, and Medical Microsystems V, (2007) 646502; 8 pages.
Giordano et al., "Toward an Integrated Electrophoretic Microdevice for Clinical Diagnostics", in Integrated Microfabricated Biodevices: Advanced Technologies for Genomics, Drug Discovery, Bioanalysis, and Clinical Diagnostics (2002) Chapter 1; pp. 1-34.
Graff et al., "Nanoparticle Separations Using Miniaturized Field-flow Fractionation Systems", Proc. Nanotechnology Conference and Trade Show (NSTI) (2005); pp. 8-12.
Greer et al., "Comparison of glass etching to xurography prototyping of microfluidic channels for DNA melting analysis", J Micromech Microengin. (2007) 17(12):2407-2413.
Guijt et al., "Chemical and physical processes for integrated temperature control in microfluidic devices", Lab Chip. (2003) 3(1):1-4.
Gulliksen A., "Microchips for Isothermal Amplification of RNA", Doctoral Thesis (2007); Department of Mol. Biosciences—University of Oslo; 94 pages.

(56) References Cited

OTHER PUBLICATIONS

Guttenberg et al., "Planar chip device for PCR and hybridization with surface acoustic wave pump", Lab Chip. (2005) 5(3):308-317.
Haeberle et al., "Microfluidic platforms for lab-on-a-chip applications", Lab Chip. (2007) 7(9):1094-1110.
Hansen et al., "Microfluidics in structural biology: smaller, faster . . . better", Curr Opin Struct Biol. (2003) 13(5):538-544.
Heid et al., "Genome Methods—Real Time Quantitative PCR", Genome Res. (1996) 6(10):986-994.
Henry C.S. [Ed], "Microchip Capillary electrophoresis", Methods in Molecular Biology, Humana Press 339 (2006) Parts I-IV in 250 pages.
Herr et al., "Investigation of a miniaturized capillary isoelectric focusing (cIEF) system using a full-field detection approach", Solid State Sensor and Actuator Workshop, Hilton Head Island (2000), pp. 4-8.
Herr et al., "Miniaturized Isoelectric Focusing (μIEF) as a Component of a Multi-Dimensional Microfluidic System", Micro Total Analysis Systems (2001) pp. 51-53.
Herr et al., Miniaturized Capillary Isoelectric Focusing (cIEF): Towards a Portable High-Speed Separation Method. In Micro Total Analysis Systems (2000) Springer, Dordrecht; pp. 367-370.
Holland et al., "Point-of-care molecular diagnostic systems—past, present and future", Curr Opin Microbiol. (2005) 8(5):504-509.
Hong et al., "Integrated nanoliter systems", Nat Biotechnol. (2003) 21(10):1179-1183.
Hong et al., "Molecular biology on a microfluidic chip", J Phys.: Condens Matter (2006) 18(18):S691-S701.
Hong et al., "Integrated Nucleic Acid Analysis in Parallel Matrix Architecture", in Integrated Biochips for DNA Analysis by Liu et al. [Eds], (2007) Chapter 8, pp. 107-116.
Horsman et al., "Forensic DNA Analysis on Microfluidic Devices: A Review", J Forensic Sci. (2007) 52(4):784-799.
Hsieh et al., "Enhancement of thermal uniformity for a microthermal cycler and its application for polymerase chain reaction", Sens Actuators B: Chemical. (2008) 130(2):848-856.
Huang et al., "Temperature Uniformity and DNA Amplification Efficiency in Micromachined Glass PCR Chip", TechConnect Briefs; Tech Proc. of the 2005 NSTI Nanotechnology Conference and Trade Show. (2005) vol. 1:452-455.
Huebner et al., "Microdroplets: A sea of applications?", Lab Chip. (2008) 8(8):1244-1254.
Iordanov et al., "PCT Array on Chip—Thermal Characterization", IEEE Sensors (2003) Conference Oct. 22-24, 2003; pp. 1045-1048.
Ji et al., "DNA Purification Silicon Chip", Sensors and Actuators A: Physical (2007) 139(1-2):139-144.
Jia et al., "A low-cost, disposable card for rapid polymerase chain reaction", Colloids Surfaces B: Biointerfaces (2007) 58:52-60.
Kaigala et al., "An inexpensive and portable microchip-based platform for integrated RT-PCR and capillary electophoresis", The Analyst (2008) 133(3):331-338.
Kajiyama et al., "Genotyping on a Thermal Gradient DNA Chip", Genome Res. (2003) 13(3):467-475.
Kang et al., "Simulation and Optimization of a Flow-Through Micro PCR Chip", NSTI-Nanotech (2006) vol. 2, pp. 585-588.
Kantak et al.,"Microfluidic platelet function analyzer for shear-induced platelet activation studies", 2nd Annual International IEEE-EMBS Special Topic Conference on Microtechnologies in Med and Biol. (May 2002) 5 pages.
Kantak et al., "Microfabricated cyclical electrical field flow fractionation", 7th International Conference on Miniaturized Chomical and Biochem Analysis Sys. (2003) pp. 1199-1202.
Kantak et al., "Platelet function analyzer: Shear activation of platelets in microchannels", Biomedical Microdevices (2003) 5(3):207-215.
Kantak et al., "Characterization of a microscale cyclical electrical field flow fractionation system", Lab Chip. (2006) 6(5):645-654.
Kantak et al., "Effect of carrier ionic strength in microscale cyclical electrical field-flow fractionation", Anal Chem. (2006) 78(8):2557-2564.

Kantak et al., "Improved theory of cyclical electrical field flow fractions", Electrophoresis (2006) 27(14):2833-2843.
Karunasiri et al.,"Extraction of thermal parameters of microbolometer infrared detectors using electrical measurement", SPIE's Inter'l Symposium on Optical Science, Engineering, and Instrumentation; Proceedings (1998) vol. 3436, Infrared Technology and Applications XXIV; (1998) 8 pages.
Kelly et al., "Microfluidic Systems for Integrated, High-Throughput DNA Analysis," Analytical Chemistry, (2005), 97A-102A, Mar. 1, 2005, in 7 pages.
Kim et al., "Reduction of Microfluidic End Effects in Micro-Field Flow Fractionation Channels", Proc. MicroTAS 2003, pp. 5-9.
Kim et al., "Multi-DNA extraction chip based on an aluminum oxide membrane integrated into a PDMS microfluidic structure", 3rd IEEE/EMBS Special Topic Conference on Microtechnology in Med and Biol. (May 2005).
Kim et al., "Geometric optimization of a thin film ITO heater to generate a uniform temperature distribution", (2006), Tokyo, Japan; pp. 293-295; Abstract.
Kim et al., "Micro-Raman thermometry for measuring the temperature distribution inside the microchannel of a polymerase chain reaction chip", J Micromech Microeng. (2006) 16(3):526-530.
Kim et al., "Patterning of a Nanoporous Membrane for Multi-sample DNA Extraction", J Micromech Microeng. (2006) 16:33-39.
Kim et al., "Performance evaluation of thermal cyclers for PCR in a rapid cycling condition", Biotechniques. (2008) 44(4):495-505.
Kim et al., "Quantitative and qualitative analysis of a microfluidic DNA extraction system using a nanoporous AlO(x) membrane", Lab Chip. (2008) 8(9):1516-1523.
Kogi et al., "Microinjection-microspectroscopy of single oil droplets in water: an application to liquid/liquid extraction under solution-flow conditions", Anal Chim Acta. (2000) 418(2):129-135.
Kopf-Sill et al., "Creating a Lab-on-a-Chip with Microfluidic Technologies", in Integrated Microfabricated Biodevices: Advanced Technologies for Genomics, Drug Discovery, Bioanalysis, and Clinical Diagnostics (2002) Chapter 2; pp. 35-54.
Kricka L.J., "Microchips, Bioelectronic Chips, and Gene Chips—Microanalyzers for the Next Century", in Biochip Technology by Cheng et al. [Eds]; (2006) Chapter 1, pp. 1-16.
Krishnan et al., "Polymerase chain reaction in high surface-to-volume ratio SiO2 microstructures", Anal Chem. (2004) 76(22):6588-6593.
Kuswandi et al., "Optical sensing systems for microfluidic devices: a review", Anal Chim Acta. (2007) 601(2):141-155.
Lagally et al., "Genetic Analysis Using Portable PCR-CE Microsystem", Proceedings 7th International Conference on Miniaturized Chemical and Biochemical Analysis Systems (2003) pp. 1283-1286.
Lagally et al., "Integrated portable genetic analysis microsystem for pathogen/infectious disease detection", Anal Chem. (2004) 76(11):3152-3170.
Lauerman L.H., "Advances in PCR technology", Anim Health Res Rev. (2004) 5(2):247-248.
Lawyer et al., "High-level Expression, Purification, and Enzymatic Characterization of Full-length Thermus aquaticus DNA Polymerase and a Truncated Form Deficient in 5′ to 3′ Exonuclease Activity." Genome research (1993) 2(4):275-287.
Lee et al., "Submicroliter-volume PCR chip with fast thermal response and very power consumption", 7th International Conference on Miniaturized Chemical and Biochemical Analysis Systems, (2003) pp. 187-190.
Lee et al., "Bulk-micromachined submicroliter-volume PCR chip with very rapid thermal response and low power consumption", Lab Chip. (2004) 4(4):401-407.
Lewin et al., "Use of Real-Time PCR and Molecular Beacons to Detect Virus Replication in Human Immunodeficiency Virus Type 1-infected Individuals on Prolonged Effective Antiretroviral Therapy". J Virol. (1999) 73(7), 6099-6103.
Li et al., "Effect of high-aspect-ratio microstructures on cell growth and attachment", 1st Annual Inter'l IEEE-EMBS Special Topic Conference on Microtechnologies in Med and Biol. Proceedings Cat. No. 00EX451; (Oct. 2000) Poster 66, pp. 531-536.

(56) References Cited

OTHER PUBLICATIONS

Li PCH., "Micromachining Methods et al." in Microfluidic Lab-on-a-Chip for Chemical and Biological Analysis and Discovery, CRC Press (2005), Chapter 2-3 to 2-5; pp. 10-49.

Li PCH., "Microfluidic Flow" in Microfluidic Lab-on-a-Chip for Chemical and Biological Analysis and Discovery, CRC Press (2005), Chapter 3, pp. 55-99.

Li PCH., "Detection Methods" in Microfluidic Lab-on-a-Chip for Chemical and Biological Analysis and Discovery, CRC Press (2005), Chapter 7, pp. 187-249.

Li PCH., "Applications to Nucleic Acids Analysis" in Microfluidic Lab-on-a-Chip for Chemical and Biological Analysis and Discovery, CRC Press (2005), Chapter 9; pp. 293-325.

Li et al., "A Continuous-Flow Polymerase Chain Reaction Microchip With Regional Velocity Control", J Microelectromech Syst. (2006) 15(1):223-236.

Lien et al., "Integrated reverse transcription polymerase chain reaction systems for virus detection", Biosens Bioelectron. (2007) 22(8):1739-1748.

Lien et al., "Microfluidic Systems Integrated with a Sample Pretreatment Device for Fast Nucleic-Acid Amplification", J Microelectro Sys. (2008) 17(2):288-301.

Lifesciences et al., "Microfluidics in commercial applications; an industry perspective." Lab Chip (2006) 6:1118-1121.

Lin et al., "Simulation and experimental validation of micro polymerase chain reaction chips", Sens Actuators B: Chemical. (2000) 71(1-2):127-133.

Linder et al., "Microfluidics at the Crossroad with Point-of-care Diagnostics", Analyst (2007) 132:1186-1192.

Liu et al., "Integrated portable polymerase chain reaction-capillary electrophoresis microsystem for rapid forensic short tandem repeat typing", Anal Chem. (2007) 79(5):1881-1889.

Liu et al. [Eds], Integrated Biochips for DNA Analysis—Biotechnology Intelligence Unit; Springer/Landes Bioscience (2007) ISBN:978-0-387-76758-1; 216 pages.

Locascio et al., "Anyl 67 Award Address—Microfluidics as a tool to enable research and discovery in the life sciences", Abstract; The 236th ACS National Meeting (Aug. 2008); 2 pages.

Mahjoob et al., "Rapid microfluidic thermal cycler for polymerase chain reaction nucleic acid amplification", Inter'l J Heat Mass Transfer. (2008) 51(9-10):2109-2122.

Marcus et al., "Parallel picoliter rt-PCR assays using microfluidics", Anal Chem. (2006) 78(3):956-958.

Mariella R.P. Jr., "Microtechnology", Thrust Area Report FY 96 UCRL-ID-125472; Lawrence Livermore National Lab., CA (Feb. 1997) Chapter 3 in 44 pages.

Mariella R., "Sample preparation: the weak link in microfluidics-based biodetection", Biomed Microdevices. (2008) 10(6):777-784.

McMillan et al., "Application of advanced microfluidics and rapid PCR to analysis of microbial targets", In Proceedings of the 8th international symposium on microbial ecology (1999), in 13 pages.

Melin et al., "Microfluidic large-scale integration: the evolution of design rules for biological automation", Annu Rev Biophys Biomol Struct. (2007) 36:213-231.

Merugu et al., "High Throughput Separations Using a Microfabricated Serial Electric Split Ssystem" (2003), Proceedings of µTAS 2003, 7th International Conference on Miniaturized Chemical and Biochemical Analysis Systems, Oct. 5-9, 2003, Squaw Valley, California; 1191-1194, in 3 pages.

Miao et al., "Low cost micro-PCR array and micro-fluidic integration on single silicon chip", Int'l J Comput Eng Science (2003) 4(2):231-234.

Miao et al., "Flip-Chip packaged micro-plate for low cost thermal multiplexing", Int'l J Comput Eng Science. (2003) 4(2):235-238.

Micheletti et al., "Microscale Bioprocess Optimisation", Curr Opin Biotech. (2006) 17:611-618.

MicroTAS 2005., "Micro Total Analysis Systems", Proceedings 9th Int. Conference on Miniaturized Systems for Chemistry and Life Sciences; Presentations/Posters/Articles for Conference; Boston, MA in Oct. 10-12, 2005 in 1667 pages.

MicroTAS 2007., "Micro Total Analysis Systems", Proceedings 11th Int. Conference on Miniaturized Systems for Chemistry and Life Sciences; Presentations/Posters/Articles for Conference; Paris, France in Oct. 7-11, 2007 in 1948 pages.

MicroTAS 2007., "Micro Total Analysis Systems", Advance Program for the Proceedings 11th Int. Conference on Miniaturized Systems for Chemistry and Life Sciences; Presentations/Posters/Articles for Conference; Paris, France in Oct. 7-11, 2007 in 42 pages.

Mitchell et al., "Modeling and validation of a molded polycarbonate continuous-flow polymerase chain reaction device," Microfluidics, BioMEMS, and Medical Microsystems, Proc. SPIE (2003) 4982:83-98.

Myers et al., "Innovations in optical microfluidic technologies for point-of-care diagnostics", Lab Chip (2008) 8:2015-2031.

Namasivayam et al., "Advances in on-chip photodetection for applications in miniaturized genetic analysis systems", J Micromech Microeng. (2004) 14:81-90.

Narayanan et al., "A microfabricated electrical SPLITT system," Lab Chip, (2006) 6:105-114.

Neuzil et al., "Disposable real-time microPCR device: lab-on-a-chip at a low cost," Mol. Biosyst., (2006) 2:292-298.

Neuzil et al., "Ultra fast miniaturized real-time PCR: 40 cycles in less than six minutes," Nucleic Acids Research, (2006) 34(11)e77, in 9 pages.

Nguyen et al. [Eds], "Microfluidics for Internal Flow Control: Microfluidics" in Fundamentals and Applications of Microfluidics; 2nd Edition (2006) Introduction Chapter 1, pp. 1-9.

Nguyen et al. [Eds], "Microfluidics for Internal Flow Control: Microvalves" in Fundamentals and Applications of Microfluidics; (2006) 2nd Edition, Chapter 6, pp. 211-254.

Nguyen et al. [Eds], "Microfluidics for Internal Flow Control: Micropumps" in Fundamentals and Applications of Microfluidics; (2006) 2nd Edition, Chapter 7, pp. 255-309.

Nguyen et al. [Eds], "Microfluidics for Life Sciences and Chemistry: Microdispensers" in Fundamentals and Applications of Microfluidics; (2006) , Chapter 11, pp. 395-418.

Nguyen et al. [Eds], "Microfluidics for Life Sciences and Chemistry: Microreactors" in Fundamentals and Applications of Microfluidics; (2006) 2nd Edition, Chapter 13, pp. 443-477.

Ning et al., "Microfabrication Processes for Silicon and Glass Chips", in Biochip Technology, CRC-Press (2006) Chapter 2, pp. 17-38.

Northrup et al., "A MEMs-based Miniature DNA Analysis System," Lawrence Livermore National Laboratory, (1995), submitted to Transducers '95, Stockholm, Sweden, Jun. 25-29, 1995, in 7 pages.

Northrup et al., "Advantages Afforded by Miniaturization and Integration of DNA Analysis Instrumentation," Microreaction Technology, (1998) 278-288.

Northrup et al., "A New Generation of PCR Instruments and Nucleic Acid Concentration Systems," in PCR Applications: Protocols for Functional Genomics, (1999), Chapter 8, pp. 105-125.

Northrup, "Microfluidics, A few good tricks," Nature materials (2004), 3:282-283.

Northrup et al.,"Microfluidics-based integrated airborne pathogen detection systems," Abstract, Proceedings of the SPIE, (2006), vol. 6398, Abstract in 2 pages.

Oh et al., "World-to-chip microfluidic interface with built-in valves for multichamber chip-based PCR assays," Lab Chip, (2005), 5:845-850.

Ohno et al., "Microfluidics: Applications for analytical purposes in chemistry and biochemistry," Electrophoresis (2008), 29:4443-4453.

Pal et al., "An integrated microfluidic for influenza and other genetic analyses," Lab Chip, (2005), 5:1024-1032, in 9 pages.

Pamme, "Continuous flow separations in microfluidic devices," Lab Chip, (2007), 7:1644-1659.

Pang et al., "A novel single-chip fabrication technique for three-dimensional MEMS structures," Institute of Microelectronics, Tsinghua University, Beijing, P.R. China, (1998), IEEE, 936-938.

Pang et al., "The Study of Single-Chip Integrated Microfluidic System," Tsinghua University, Beijing, P.R. China, (1998), IEEE, 895-898.

(56) References Cited

OTHER PUBLICATIONS

Papautsky et al., "Effects of rectangular microchannel aspect ratio on laminar friction constant", in Microfluidic Devices and Systems II (1999) 3877:147-158.
Petersen, Kurt E., "Silicon as a Mechanical Material." Proceedings of the IEEE, (May 1982) 70(5):420-457.
Petersen et al., "Toward Next Generation Clinical Diagnostic Instruments: Scaling and New Processing Paradigms," Biomedical Microdevices (1998) 1(1):71-79.
Poser et al., "Chip elements for fast thermocycling," Sensors and Actuators A, (1997), 62:672-675.
Pourahmadi et al., "Toward a Rapid, Integrated, and Fully Automated DNA Diagnostic Assay for Chlamydia trachomatis and Neisseria gonorrhea," Clinical Chemistry, (2000), 46(9):1511-1513.
Pourahmadi et al., "Versatile, Adaptable and Programmable Microfluidic Platforms for DNA Diagnostics and Drug Discovery Assays," Micro Total Analysis Systems, (2000), 243-248.
Raisi et al., "Microchip isoelectric focusing using a miniature scanning detection system," Electrophoresis, (2001), 22:2291-2295.
Raja et al., "Technology for Automated, Rapid, and Quantitative PCR or Reverse Transcription-PCR Clinical Testing," Clinical Chemistry, (2005), 51(5):882-890.
Reyes et al., "Micro Total Analysis Systems. 1. Introduction, Theory, and Technology", Anal Chem (2002) 74:2623-2636.
Rodriguez et al., "Practical integration of polymerase chain reaction amplification and electrophoretic analysis in microfluidic devices for genetic analysis," Electrophoresis, (2003), 24:172-178.
Roper et al., "Advances in Polymer Chain Reaction on Microfluidic Chips," Anal. Chem., (2005), 77:3887-3894.
Ross et al., "Scanning Temperature Gradient Focusing for Simultaneous Concentration and Separation of Complex Samples," Micro Total Analysis Systems 2005, vol. 2, (2005), Proceedings of μTAS 2005, Ninth International Conference on Miniaturized Systems for Chemistry and Life Sciences, Oct. 9-13, 2005, Boston, Massachusetts; 1022-1024.
Ross et al., "Simple Device for Multiplexed Electrophoretic Separations Using Gradient Elution Moving Boundary Electrophoresis with Channel Current Detection," Anal. Chem., (2008), 80(24):9467-9474.
Sadler et al., "Thermal Management of BioMEMS: Temperature Control for Ceramic-Based PCR and DNA Detection Devices," IEEE Transactions on Components and Packaging Technologies, (2003) 26(2):309-316.
Sant et al., "An Integrated Optical Detector for Microfabricated Electrical Field Flow Fractionation System," Proceedings of μTAS 2003, 7th International Conference on Miniaturized Chemical and Biochemical Analysis Systems, Oct. 5-9, 2003, Squaw Valley, California; pp. 1259-1262.
Sant et al., "Geometric scaling effects on instrumental plate height in field flow fractionation", J Chromatography A (2006) 1104:282-290.
Sant H.J., "Reduction of End Effect-Induced Zone Broadening in Field-Flow Fractionation Channels", Anl Chem. (2006) 78:7978-7985.
Sant et al., "Microscale Field-Flow Fractionation: Theory and Practice", in Microfluidic Technologies for Miniaturized Analysis Systems. (2007) Chapter 12, pp. 4710521.
Schäferling et al., "Optical technologies for the read out and quality control of DNA and protein microarrays," Anal Bioanal Chem, (2006), 385: 500-517.
Serpengüzel et al., "Microdroplet identification and size measurement in sprays with lasing images", Optics express (2002) 10(20):1118-1132.
Shackman et al., "Gradient Elution Moving Boundary Electrophoresis for High-Throughput Multiplexed Microfluidic Devices," Anal. Chem. (2007), 79(2), 565-571.
Shackman et al., "Temperature gradient focusing for microchannel separations," Anal Bioanal Chem, (2007), 387:155-158.
Shadpour et al., "Multichannel Microchip Electrophoresis Device Fabricated in Polycarbonate with an Integrated Contact Conductivity Sensor Array," Anal Chem., (2007), 79(3), 870-878.
Sia et al., "Microfluidic devices fabricated in poly(dimethylsiloxane) for biological studies," Electrophoresis, (2003), 24:3563-3576.
Sigurdson M., "AC Electrokinetic Enhancement for Assay Enhancement", ProQuest LLC (2008) Doctoral Thesis UMI Microform 3319791 in 24 pages.
Singh et al., "PCR thermal management in an integrated Lab on Chip," Journal of Physics: Conference Series, (2006), 34:222-227.
Situma et al., "Merging microfluidics with microarray-based bioassays", Biomol Engin. (2006) 23:213-231.
Smith et al., "(576d) Micropatterned fluid lipid bilayers created using a continuous flow microspotter for multi-analyte assays," (2007), Biosensors II, 2007 AIChE Annual Meeting, Nov. 8, 2007, Abstract in 2 pages.
Sommer et al., "Introduction to Microfluidics", in Microfluidics for Biological Applications by Tian et al. [Eds] (2008) Chapter 1, pp. 1-34.
Squires et al., "Microfluidics: Fluid physics at the nanoliter scale," Reviews of Modern Physics, (2005), 77(3):977-1026.
Sundberg et al., "Solution-phase DNA mutation scanning and SNP genotyping by nanoliter melting analysis," Biomed Microdevices, (2007), 9:159-166, in 8 pages.
Tabeling, P. [Ed.], "Physics at the micrometric scale," in Introduction to Microfluidics (2005) Chapter 1, pp. 24-69.
Tabeling, P. [Ed.], "Hydrodynamics of Microfluidic Systems", in Introduction to Microfluidics; (2005) Chapter 2, pp. 70-129.
Tabeling, P. [Ed.], Introduction to Microfluidics; (2005) Chapters 5-7, pp. 216-297.
Tanaka et al., "Improved Method of DNA Extraction from Seeds Using Amine-Dendrimer Modified Magnetic Particles", Proceedings of the 74th Annual Meeting of the Electrochemical Society of Japan; Abstract #2E09 on p. 149, Mar. 29, 2007; Faculty of Engineering, Science University of Tokyo; 4 pages.
Taylor et al., Fully Automated Sample Preparation for Pathogen Detection Performed in a Microfluidic Cassette, in Micro Total Analysis Systems, Springer (2001), pp. 670-672.
Taylor et al., "Lysing Bacterial Spores by Sonication through a Flexible Interface in a Microfluidic System," Anal. Chem., (2001), 73(3):492-496.
Taylor et al., "Microfluidic Bioanalysis Cartridge with Interchangeable Microchannel Separation Components," (2001), The 11th International Conference on Solid-State Sensors and Actuators, Jun. 10-14, 2001, Munich, Germany; 1214-1247.
Taylor et al., "Disrupting Bacterial Spores and Cells using Ultrasound Applied through a Solid Interface," (2002), 2nd Annual International IEEE-EMBS Special Topic Conference on Microtechnologies in Medicine & Biology, May 2-4, 2002, Madison, Wisconsin; 551-555.
Thorsen et al., "Microfluidic Large-scale integration," Science, (2002), 298:580-584.
Toriello et al., "Multichannel Reverse Transcription-Polymerase Chain Reaction Microdevice for Rapid Gene Expression and Biomarker Analysis," Anal. Chem., (2006) 78(23):7997-8003.
Ugaz et al., "Microfabricated electrophoresis systems for DNA sequencing and genotyping applications," Phil. Trans. R. Soc. Lond. A, (2004), 362:1105-1129.
Ugaz et al., "PCR in Integrated Microfluidic Systems", in Integrated Biochips for DNA Analysis by Liu et al. [Eds]; (2007) Chapter 7, pp. 90-106.
Ullman et al., "Luminescent oxygen channeling assay (LOCI™): sensitive, broadly applicable homogeneous immunoassay method". Clin Chem. (1996) 42(9), 1518-1526.
Vinet et al., "Microarrays and microfluidic devices: miniaturized systems for biological analysis," Microelectronic Engineering, (2002), 61-62:41-47.
Wang et al., "From biochips to laboratory-on-a-chip system", in Genomic Signal Processing and Statistics by Dougherty et al. [Eds]; (2005) Chapter 5, pp. 163-200.
Wang et al., "A disposable microfluidic cassette for DNA amplification and detection", Lab on a Chip (2006) 6(1):46-53.

(56) References Cited

OTHER PUBLICATIONS

Wang et al., "Micromachined Flow-through Polimerase Chain Reaction Chip Utilizing Multiple Membrane-activated Micropumps," (2006), MEMS 2006, Jan. 22-26, 2006, Istanbul, Turkey; 374-377.
Woolley A.T., "Integrating Sample Processing and Detection with Microchip Capillary Electrophoresis of DNA", in Integrated Biochips for DNA Analysis by Liu et al. [Eds]; (2007) Chapter 5, pp. 68-77.
Xiang et al., "Real Time PCR on Disposable PDMS Chip with a Miniaturized Thermal Cycler," Biomedical Microdevices, (2005), 7(4):273-279.
Xuan, "Joule heating in electrokinetic flow," Electrophoresis, (2008), 298:33-43.
Yang et al., "High sensitivity PCR assay in plastic micro reactors," Lab Chip, (2002), 2:179-187.
Yang et al., "An independent, temperature controllable-microelectrode array," Anal. Chem., (2004), 76(5):1537-1543.
Yang et al., "Cost-effective thermal isolation techniques for use on microfabricated DNA amplification and analysis devices," J Micromech Microeng, (2005), 15:221-230.
Yobas et al., Microfluidic Chips for Viral RNA Extraction & Detection, (2005), 2005 IEEE, 49-52.
Yobas et al., "Nucleic Acid Extraction, Amplification, and Detection on Si-Based Microfluidic Platforms," IEEE Journal of Solid-State Circuits, (2007), 42(8):1803-1813.
Yoon et al., "Precise temperature control and rapid thermal cycling in a micromachined DNA polymer chain reaction chip," J. Micromech. Microeng., (2002), 12:813-823.
Zhang et al, "Temperature analysis of continuous-flow micro-PCR based on FEA," Sensors and Actuators B, (2002), 82:75-81.
Zhang et al, "Continuous-Flow PCR Microfluidics for Rapid DNA Amplification Using Thin Film Heater with Low Thermal Mass," Analytical Letters, (2007), 40:1672-1685, in 15 pages.
Zhang et al, "Direct Adsorption and Detection of Proteins, Including Ferritin, onto Microlens Array Patterned Bioarrays," J Am Chem Soc., (2007), 129:9252-9253.
Zhang et al, "Micropumps, microvalves, and micromixers within PCR microfluidic chips: Advances and trens," Biotechnology Advances, (2007), 25:483-514.
Zhao et al, "Heat properties of an integrated micro PCR vessel," Proceedings of SPIE, (2001), International Conference on Sensor Technology, 4414:31-34.
Zou et al., "Micro-assembled multi-chamber thermal cycler for low-cost reaction chip thermal multiplexing," Sensors and Actuators A, (2002), 102:114-121.
Zou et al., "Miniaturized Independently Controllable Multichamber Thermal Cycler," IEEE Sensors Journal, (2003), 3(6):774-780.
Petitioner's Reply to Patent Owner's Response to Petition in Inter Partes Review of U.S. Pat. No. 7,998,708 and Exhibit List (Paper 32 in IPR 2019-00488) dated Jan. 31, 2020 (34 pages).
Petitioner's Reply to Patent Owner's Response to Petition in Inter Partes Review of U.S. Pat. No. 8,323,900 and Exhibit List (Paper 32 in IPR 2019-00490) dated Jan. 31, 2020 (35 pages).
Second Declaration of Bruce K. Gale, Ph.D. (Exhibit 1026 in IPR2019-00488 and IPR2019-00490) dated Jan. 31, 2020 (91 pages).
Transcript of Deposition of M. Allen Northrup, Ph.D., (Exhibit 1027 in IPR2019-00488 and IPR2019-00490), taken Dec. 19, 2019 (109 pages).
Patent Owner's Sur-Reply in Inter Partes Review of U.S. Pat. No. 8,323,900 (Paper 42 in IPR2019-00490) dated Mar. 12, 2020 (39 pages).
Patent Owner's Sur-Reply in Inter Partes Review of U.S. Pat. No. 7,998,708 (Paper 43 in IPR 2019-00488) dated Mar. 12, 2020 (41 pages).
Transcript of Second Deposition of Bruce K. Gale, Ph.D., (Exhibit 2068 in IPR2019-00488 and IPR2019-00490), taken Feb. 19, 2020 (352 pages).
Anderson et al., "Microfluidic biochemical analysis system" Proc. 1997 IEEE Int. Conf. Solid-State Sens. Actuat. (1997) pp. 477-480.

Anderson et al., "Advances in Integrated Genetic Analysis" Micro Total Analysis Systems '98 Conference Proceedings, D. Kluwer Academic Publishers (1998) in 6 pages.
Anderson et al., "A Miniature Integrated Device for Automated Multistep Genetic Assays" Nucleic Acids Research (2000) 28(12), i-vi.
Burns et al., "Microfabricated Structures for Integrated DNA Analysis" Proc. Natl. Acad. Sci. USA (May 1996) 93: 5556-5561.
Harrison et al., "Capillary Electrophoresis and Sample Injection Systems Integrated on a Planar Glass Chip", Anal. Chem., (1992) 64: 1926-1932.
Hsueh et al., "A microfabricated, electrochemiluminescence cell for the detection of amplified DNA" Proc. 1995 IEEE Int. Conf. Solid-State Sens. Actuators (1995) pp. 768-771.
Hsueh et al., "DNA quantification with an electrochemiluminescence microcell" Proc. 1997 IEEE Int. Conf. Solid-State Sens. Actuators (1997) pp. 175-178.
Jiang et al., "Directing cell migration with asymmetric micropatterns" Proc. Natl. Acad. Sci. USA (2005) 102, 975-978.
Lagally et al., "Monolithic integrated microfluidic DNA amplification and capillary electrophoresis analysis system" Sensors and Actuators B (2000) 63:138-146.
Manz et al., "Design of an open-tubular column liquid chromatograph using silicon chip technology" Sensors and Actuators B (1990) 1:249-255.
Manz et al., "Planar chips technology for miniaturization and integration of separation techniques into monitoring systems: Capillary electrophoresis on a chip" Journal of Chromatography A (1992) 593:253-258.
Rhee et al., "Drop Mixing in a Microchannel for Lab-on-a-Chip Applications" Langmuir (2008) 24 (2): 590-601.
Sammarco et al., "Thermocapillary Pumping of Discrete Drops in Microfabricated Analysis Devices" AIChE Journal (1999) 45(2): 350-366.
Taylor et al., "Optimization of the performance of the polymerase chain reaction in silicon-based microstructures" Nucleic Acids Res. (1997) vol. 25, pp. 3164-3168.
Terry et al., "A Gas Chromatographic Air Analyzer Fabricated on a Silicon Wafer" IEEE T Electron Dev (1979) 26:1880-1886.
Whitesides G.M., "The origins and the future of microfluidics" Nature (2006) 442(7101):368-373.
Woias P., "Micropumps—past, progress and future prospects" Sensors and Actuators B (2005) 105, 28-38.
Woolley et al., "Functional integration of PCR amplification and capillary electrophoresis in a microfabricated DNA analysis device" Anal. Chem. (1996) vol. 68, pp. 4081-4086.
Wu et al., "Fabrication of Complex Three-dimensional Microchannel Systems in PDMS" J. Am. Chem. Soc. (2003) 125, 554-559.
Zhang et al., "Parallel DNA amplification by convective polymerase chain reaction with various annealing temperatures on a thermal gradient device," Analytical Biochemistry, (2009) 387:102-112.
Record of Oral Hearing in IPR2019-00488 and IPR2019-00490 held Apr. 21, 2020 in 80 pages; Petitioner's Demonstratives for Oral Hearing in IPR2019-00488 and IPR2019-00490 held Apr. 21, 2020 in 72 pages; Patent Owner's Demonstratives for Oral Hearing in IPR2019-00488 and IPR2019-00490 held Apr. 21, 2020 in 88 pages; Patent Owner's Objections to Petitioner's Oral Hearing Demonstratives in IPR2019-00488 and IPR2019-00490 dated Apr. 16, 2020 (4 pages).
Judgment/Final Written Decision in Inter Partes Review of U.S. Pat. No. 7,998,708 (Paper No. 52 in IPR2019-00488) dated Jul. 14, 2020 (43 pages).
Judgment/Final Written Decision in Inter Partes Review of U.S. Pat. No. 8,323,900 (Paper No. 51 in IPR2019-00490) dated Jul. 14, 2020 (43 pages).
Petition for Inter Partes Review of U.S. Pat. No. 8,273,308 (Paper 2 in IPR2020-01083) dated Jun. 12, 2020 (104 pages).
Petition for Inter Partes Review of U.S. Pat. No. 8,273,308 (Paper 2 in IPR2020-01091) dated Jun. 12, 2020 (105 pages).
Petition for Inter Partes Review of U.S. Pat. No. 8,803,069 (Paper 2 in IPR2020-01095) dated Jun. 12, 2020 (84 pages).
Petition for Inter Partes Review of U.S. Pat. No. 8,803,069 (Paper 3 in IPR2020-01100) dated Jun. 12, 2020 (83 pages).

(56) References Cited

OTHER PUBLICATIONS

Petition for Inter Partes Review of U.S. Pat. No. 8,709,787 (Paper 2 in IPR2020-01132) dated Jun. 18, 2020 (96 pages).
Petition for Inter Partes Review of U.S. Pat. No. 8,415,103 (Paper 2 in IPR2020-01133) dated Jun. 18, 2020 (96 pages).
Petition for Inter Partes Review of U.S. Pat. No. 8,709,787 (Paper 2 in IPR2020-01137) dated Jun. 19, 2020 (86 pages).
Petition for Inter Partes Review of U.S. Pat. No. 8,415,103 (Paper 2 in IPR2020-01136) dated Jun. 19, 2020 (85 pages).
Declaration of Mark A. Burns, Ph.D. (Exhibit N1001 in IPR2020-01083, IPR2020-01091, IPR2020-01095 and IPR2020-01100) dated Jun. 12, 2020 (378 pages).
Declaration of Mark A. Burns, Ph.D. (Exhibit N1101 in IPR2020-01132 and IPR2020-01133) dated Jun. 17, 2020 (253 pages).
Declaration of Mark A. Burns, Ph.D. (Exhibit N1201 in IPR2020-01136 and IPR2020-01137) dated Jun. 19, 2020 (205 pages).
First Amended and Supplemental Complaint filed by Becton, Dickinson et al. On Jun. 25, 2020 in U.S. District Court, Delaware, Case #1:19-cv-01126-LPS (55 pages).
Answer to Amended and Supplemental Complaint filed by NeuModx Molecular, Inc. on Jul. 16, 2020 in U.S. District Court, Delaware, Case #1:19-cv-01126-LPS (42 pages).
Petitioner's Notice of Appeal in Inter Partes Review of U.S. Pat. No. 7,998,708 (Paper No. 54 in IPR2019-00488) dated Sep. 9, 2020 (48 pages).
Petitioner's Notice of Appeal in Inter Partes Review of U.S. Pat. No. 8,323,900 (Paper No. 53 in IPR2019-00490) dated Sep. 9, 2020 (48 pages).

\* cited by examiner

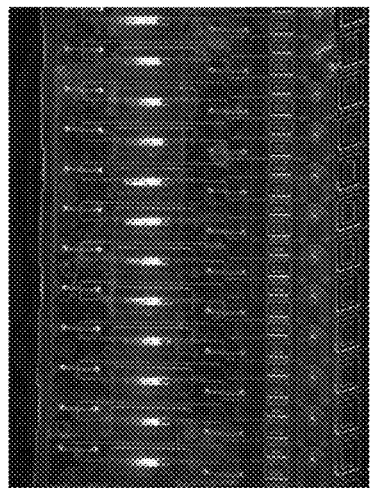
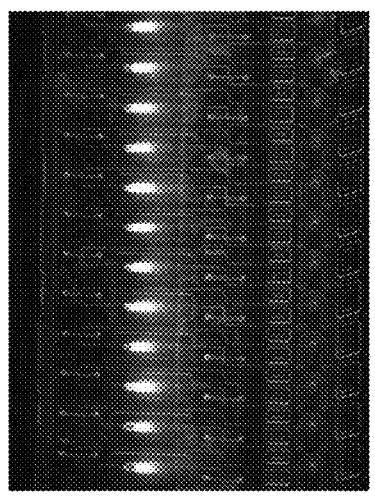
FIG. 8A

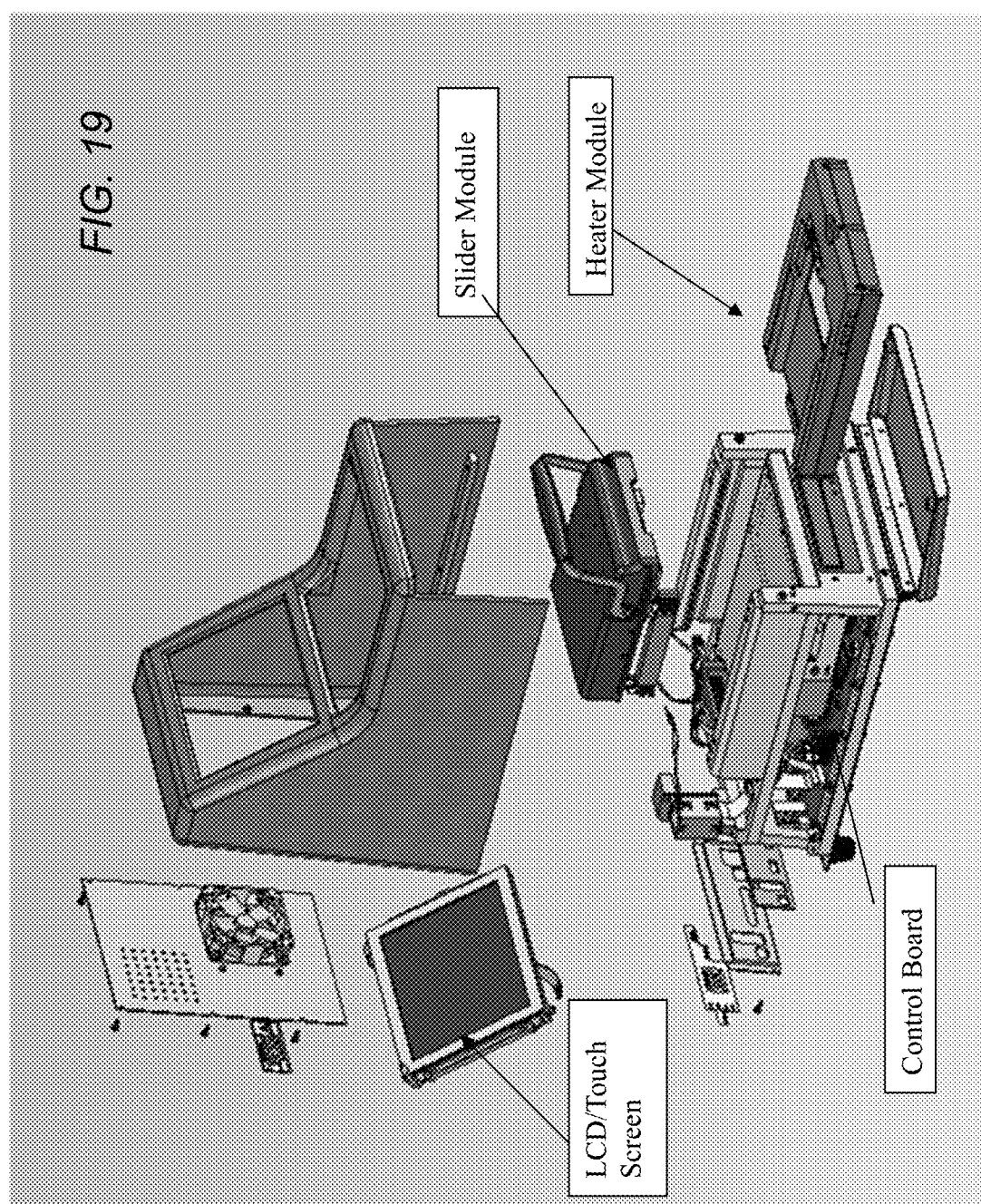

FLUORESCENCE DETECTOR FOR MICROFLUIDIC DIAGNOSTIC SYSTEM

CLAIM OF PRIORITY

This application is a continuation of U.S. patent application Ser. No. 15/795,842, filed Oct. 27, 2017 and scheduled to issue as U.S. Pat. No. 10,695,764 on Jun. 30, 2020, which is a continuation of U.S. patent application Ser. No. 14/537,517, filed Nov. 10, 2014 and issued as U.S. Pat. No. 9,802,199 on Oct. 31, 2017, which is a continuation of U.S. patent application Ser. No. 11/940,321, filed Nov. 14, 2007 and issued as U.S. Pat. No. 8,883,490 on Nov. 11, 2014, which claims the benefit of priority of U.S. Provisional Application No. 60/859,284, filed Nov. 14, 2006, and U.S. Provisional Application No. 60/959,437, filed Jul. 13, 2007. U.S. patent application Ser. No. 11/940,321 is also a continuation-in-part of U.S. patent application Ser. No. 11/728,964, filed Mar. 26, 2007 and issued as U.S. Pat. No. 9,040,288 on May 26, 2015, which claims the benefit of priority of U.S. Provisional Application No. 60/786,007, filed Mar. 24, 2006, and U.S. Provisional Application No. 60/859,284, filed Nov. 14, 2006. The disclosures of U.S. patent application Ser. No. 11/940,321; U.S. Provisional Application No. 60/859,284; U.S. Provisional Application No. 60/959,437; and U.S. patent application Ser. No. 11/728,964 are considered part of the disclosure of this application, and are incorporated by reference herein in their entirety.

TECHNICAL FIELD

The technology described herein generally relates to systems for detecting polynucleotides in samples, particularly from biological samples. The technology more particularly relates to microfluidic systems that carry out PCR on nucleotides of interest within microfluidic channels, and detect those nucleotides.

BACKGROUND

The medical diagnostics industry is a critical element of today's healthcare infrastructure. At present, however, diagnostic analyses no matter how routine have become a bottleneck in patient care. There are several reasons for this. First, many diagnostic analyses can only be done with highly specialist equipment that is both expensive and only operable by trained clinicians. Such equipment is found in only a few locations—often just one in any given urban area. This means that most hospitals are required to send out samples for analyses to these locations, thereby incurring shipping costs and transportation delays, and possibly even sample loss. Second, the equipment in question is typically not available 'on-demand' but instead runs in batches, thereby delaying the processing time for many samples because they must wait for a machine to fill up before they can be run.

Understanding that sample flow breaks down into several key steps, it would be desirable to consider ways to automate as many of these as possible. For example, a biological sample, once extracted from a patient, must be put in a form suitable for a processing regime that typically involves using PCR to amplify a vector of interest. Once amplified, the presence of a nucleotide of interest from the sample needs to be determined unambiguously. Sample preparation is a process that is susceptible to automation but is also relatively routinely carried out in almost any location. By contrast, steps such as PCR and nucleotide detection have customarily only been within the compass of specially trained individuals having access to specialist equipment.

There is a need for a method and apparatus of carrying out PCR and detection on prepared biological samples, and preferably with high throughput. In particular there is a need for an easy-to-use device that can deliver a diagnostic result on several samples in a short time.

The discussion of the background to the technology herein is included to explain the context of the technology. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

The present technology addresses systems for detecting polynucleotides in samples, particularly from biological samples. In particular, the technology relates to microfluidic systems that carry out PCR on nucleotides of interest within microfluidic channels, and detect those nucleotides.

The present technology provides for a fluorescent detector, comprising: a LED emitting light of a specified color that excites a probe associated with one or more polynucleotides contained within a microfluidic channel; and a photodiode configured to collect emitted light of the specified color, wherein the photodiode is connected to a pre-amplifier circuit having a time-constant of less than about 1 s.

A diagnostic apparatus, comprising: one or more microfluidic channels configured to amplify one or more polynucleotides; and one or more fluorescence detectors configured to detect presence of the one or more polynucleotides in the one or more channels by detecting fluorescent light emitted from a probe associated with the one or more polynucleotides, wherein the one or more detectors each comprise: a first LED emitting light of a first color; a second LED emitting light of a second color; a first photodiode configured to collect emitted light of the first color; a second photodiode configured to collect emitted light of the second color; and wherein the first and second photodiodes are each connected to a pre-amplifier circuit having a time-constant of less than of about 1 second. In certain embodiments, the time constant is 50-100 ms.

In certain other embodiments, the pre-amplifier circuit further comprises a resistor having a resistance in excess of 0.5 GΩ.

The detector can be configured to detect fluorescence from one or more microfluidic channels in a removable microfluidic cartridge, such as disposed within a receiving bay in the apparatus.

The technology further provides for a diagnostic apparatus, comprising: one or more microfluidic channels configured to amplify one or more polynucleotides; and one or more fluorescence detectors configured to detect presence of the one or more polynucleotides in the one or more channels by detecting fluorescent light emitted from a probe associated with the one or more polynucleotides, wherein the one or more detectors each comprise: a LED emitting light of a specified color that excites the probe; a photodiode configured to collect emitted light of the specified color; and wherein the photodiode is connected to a pre-amplifier circuit having a time-constant of less than about 1 s.

The technology further provides for a diagnostic apparatus, comprising: one or more microfluidic channels configured to amplify one or more polynucleotides; and one or more fluorescence detectors configured to detect presence of the one or more polynucleotides in the one or more channels by detecting fluorescent light emitted from a probe associated with the one or more polynucleotides, wherein the one or more detectors each comprise: a first LED emitting light of a first color; a second LED emitting light of a second color; a first photodiode configured to collect emitted light of the first color; a second photodiode configured to collect emitted light of the second color; and wherein the first and second photodiodes are each connected to a pre-amplifier circuit having a Gain of about $10^9$.

The details of one or more embodiments of the technology are set forth in the accompanying drawings and further description herein. Other features, objects, and advantages of the technology will be apparent from the description and drawings, and from the claims.

BRIEF DESCRIPTION OF THE DRAWINGS

FIG. 8A shows effects of aperturing on fluorescence intensity.

FIG. 19 shows an exploded view of an exemplary apparatus;

DETAILED DESCRIPTION

Overview

Figure 1:
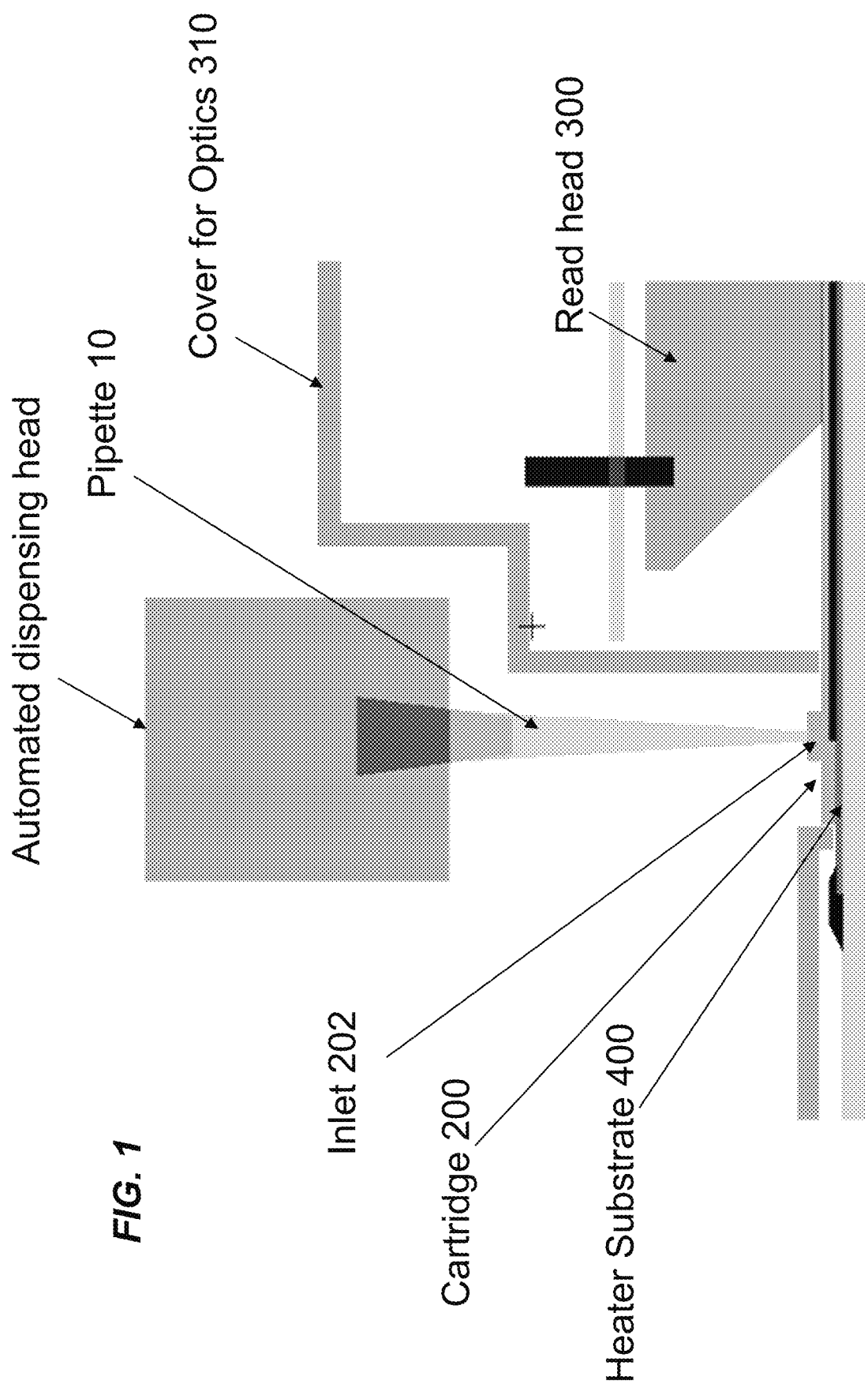
FIG. 1 shows a cross-section of a pipetting head, a detector, and a cartridge in position in a microfluidic apparatus.
Figure 2:
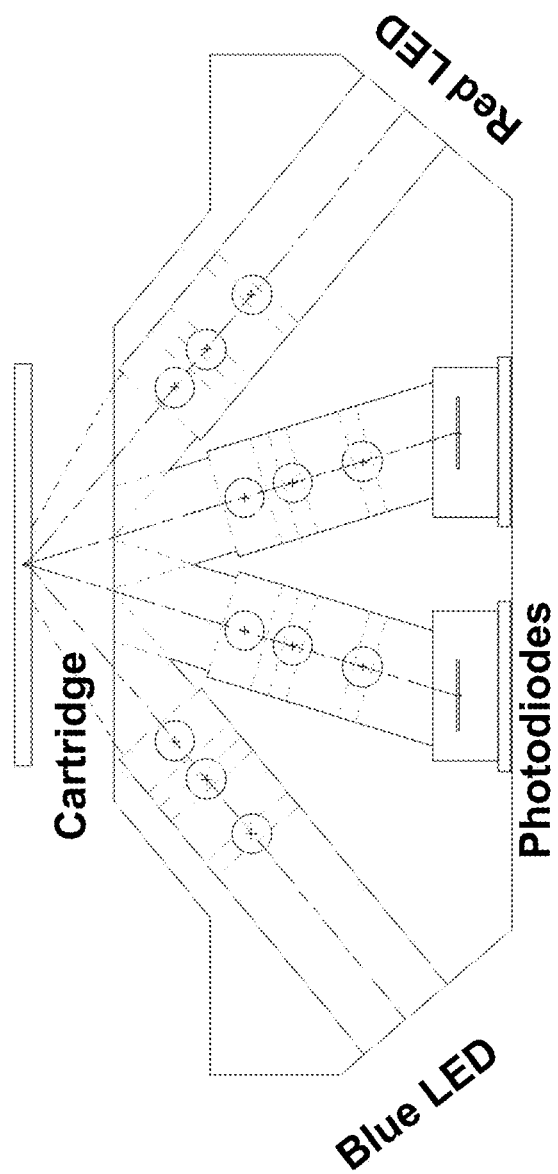
FIG. 2 shows a cross-sectional view of an exemplary detector, inverted relative to other views herein.
Figure 3:
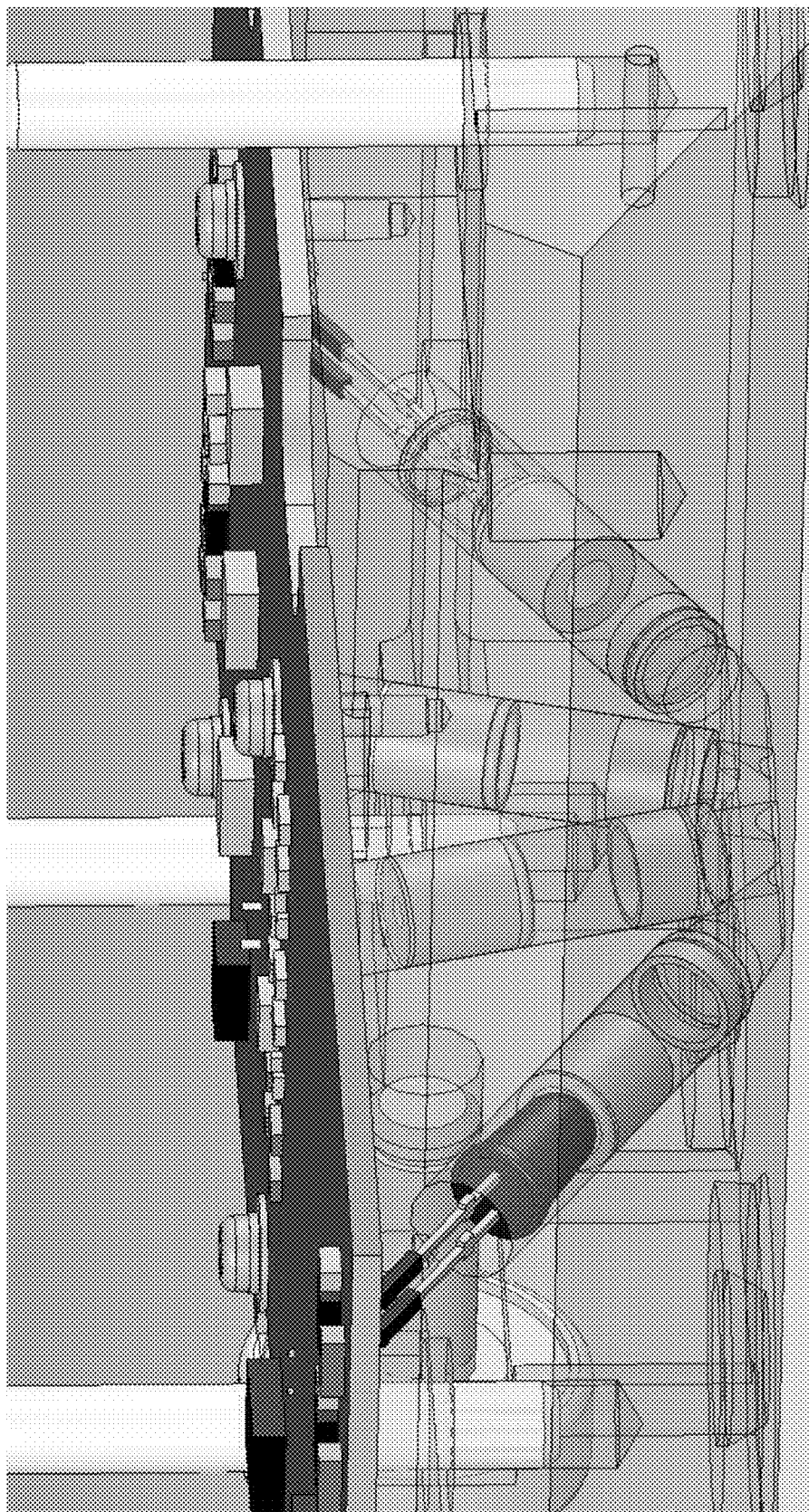
FIG. 3 shows a cutaway view of an exemplary detector in a read-head.

One aspect of the present technology relates to a fluorescence detection system for use with a microfluidic-based diagnostic system. In particular, the detection system described herein is configured to detect presence of a nucleotide amplified by, e.g., a polymerase chain reaction (PCR), in a microfluidic channel. It is to be understood that, unless specifically made clear to the contrary, where the term PCR is used herein, any variant of PCR including but not limited to real-time and quantitative, and any other form of polynucleotide amplification is intended to be encompassed.

As further described herein, a microfluidic channel, within which presence of an analyte is detected by the detection system, is typically a chamber or a reactor, such as a PCR reactor, wherein a sample is subjected to a temperature protocol that causes one or more reactions to occur.

Channels of a microfluidic network in a lane of a microfluidic substrate, such as in a cartridge, typically have at least one sub-millimeter cross-sectional dimension. For example, channels of such a network may have a width and/or a depth of about 1 mm or less (e.g., about 750 microns or less, about 500 microns, or less, about 250 microns or less).

By microfluidic, as used herein, is meant that volumes of sample, and/or reagent, and/or amplified polynucleotide are from about 0.1 Tl to about 999 Tl, such as from 1-100 Tl, or from 2-25 Tl. Similarly, as applied to a cartridge, the term microfluidic means that various components and channels of the cartridge, as further described herein, are configured to accept, and/or retain, and/or facilitate passage of microfluidic volumes of sample, reagent, or amplified polynucleotide.

Furthermore, the detection system can be configured to simultaneously detect presence of several nucleotides, distributed amongst several microfluidic channels. The microfluidic channel or channels may be in, for example, a microfluidic substrate, such as found in a microfluidic cartridge, with which the detector is in communication. In particular, the detection system is configured to detect very weak signals as are characteristic of samples having very small effective amounts of the analyte (e.g., polynucleotide) whose presence is being determined. The detector is typically mounted within an apparatus that controls the progress of the amplification reaction in the one or more microfluidic channels, such as by controlled selective application of localized heat to the one or more channels, wherein the apparatus is also typically able to accept user instructions as input, and to provide the result of detection as an output. Other characteristics of such an apparatus are described further herein.

Embodiments of the optical system described herein are configured to measure fluorescence from a real-time PCR reaction but it would be understood that the principles involved could be transferred to monitoring other reactions on the same or similar scales. The process amplifies a single copy of target DNA into millions or billions of copies depending on the number of PCR cycles performed in the reaction. As most of the real-time PCR reaction systems such as Taqman or Scorpion chemistries involve one to one correspondence between the number of target DNA copies and the number of fluorescent probes, the amount of fluorescence emanating from a reaction volume should be detectable by a sensitive fluorescent detection system, as is described herein. Assuming the PCR reaction is 100% efficient, the sensitivity of the PCR system is proportional to the detection volume seen by the photodetector. However, as DNA molecules will diffuse approximately a millimeter over a time of 14-20 minutes (the typical total time required to perform 45 cycles of PCR according to methods described herein) and the probe molecules may diffuse an even greater distance than DNA (probe molecules are much smaller than template DNA molecules), the detection volume can be slightly smaller than the full reaction volume in order to detect each and every copy of DNA initially present in the reactor at the start of the reaction. The detection volume may thus be 80% of, or as low as 50% of, the reaction volume.

The microfluidic PCR reactor used herein is typically a straight microchannel, 0.3 mm deep and 1.5 mm wide. Depending on the required reaction volume, the length of the reactor can be from 10 mm to 20 mm. The width of the channel can be varied from 100 microns to 3 mm to be able to use the same geometry of PCR heaters to maintain desired temperature uniformity and speed of heating (which depends on effective thermal mass heated by the heaters). The depth of the channel can also be increased to 350 microns or 400 microns without incurring loss of uniformity of temperature.

FIG. 1 shows a schematic cross-sectional view of a part of an apparatus as described herein, showing input of sample into a microfluidic cartridge 200 via a pipette 10 (such as a disposable pipette) and an inlet 202 in the cartridge. Suitable cartridges 200 are further described herein but it is to be understood that the detection system can also be configured to detect analytes in microfluidic channels found in situ in the apparatus. Such channels may therefore be fixed in the apparatus and reusable, for example by flushing through after each use, instead of being associated with a removable and disposable item such as a cartridge. Inlet 202 is preferably configured to receive a pipette or the bottom end of a PCR tube and thereby accept sample for analysis with minimum waste, and with minimum introduction of air. Although not apparent from FIG. 1, several pipettes 10 may operate in parallel with one another to introduce multiple samples into cartridge 200. Cartridge 200 is disposed on top of and in contact with a heater substrate 400. A detector, as further described herein, comprises a read head 300 and a cover 310. Read head 300 is positioned above cartridge 200, and a cover for optics 310 restricts the amount of ambient light that can be detected by the read head.

Fluorescence Detection System, Including Lenses and Filters, and Multiple Parallel Detection for a Multi-Lane Cartridge The detection system herein is configured to monitor fluorescence coming from one or more species involved in a biochemical reaction. The system can be, for example, an optical detector having a light source that selectively emits light in an absorption band of a fluorescent dye, and a light detector that selectively detects light in an emission band of the fluorescent dye, wherein the fluorescent dye corresponds to a fluorescent polynucleotide probe or a fragment thereof, as further described elsewhere herein. Alternatively, the optical detector can include a bandpass-filtered diode that selectively emits light in the absorption band of the fluorescent dye and a bandpass filtered photodiode that selectively detects light in the emission band of the fluorescent dye. For example, the optical detector can be configured to independently detect a plurality of fluorescent dyes having different fluorescent emission spectra, wherein each fluorescent dye corresponds to a fluorescent polynucleotide probe or a fragment thereof. For example, the optical detector can be configured to independently detect a plurality of fluorescent dyes at a plurality of different locations of, for example, a microfluidic substrate, wherein each fluorescent dye corresponds to a fluorescent polynucleotide probe or a fragment thereof. The detector further has potential for 2, 3 or 4 color detection and is controlled by software, preferably custom software, configured to sample information from the detector.

The detection system described herein is capable of detecting a fluorescence signal from nanoliter scale PCR reactions. Advantageously, the detector is formed from inexpensive components, having no moving parts. The detector can be configured to couple to a microfluidic cartridge as further described herein, and can also be part of a pressure application system, such as a sliding lid on an apparatus in which the detector is situated, that keeps the cartridge in place.

Figure 4A:
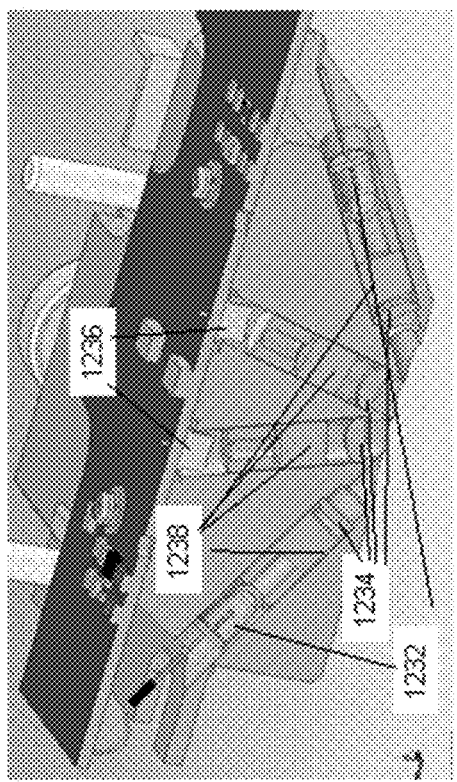
FIGS. 4A and 4B show perspective and cross-sectional views respectively of a detector in a read-head.
Figure 4B:
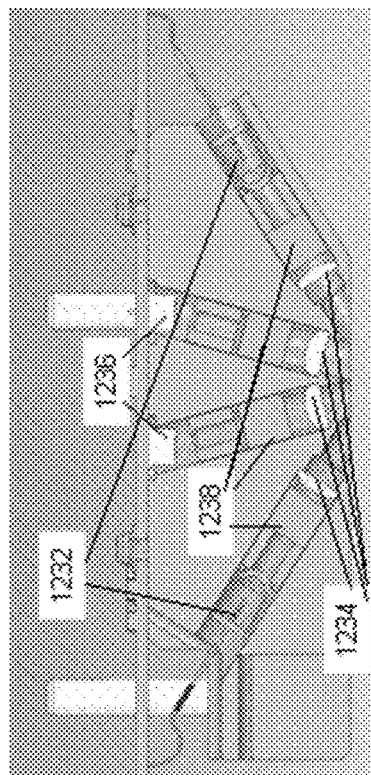

FIGS. 2-4B depict an embodiment of a highly sensitive fluorescence detection system that includes light emitting diodes (LED's), photodiodes, and filters/lenses for monitoring, in real-time, one or more fluorescent signals emanating from the microfluidic channel. The embodiment in FIGS. 2-4B displays a two-color detection system having a modular design that couples with a single microfluidic channel found, for example, in a microfluidic cartridge. It would be understood by one skilled in the art that the description herein could also be adapted to create a detector that just detects a single color of light. FIGS. 4A and 4B show elements of optical detector elements 1220 including light sources 1232 (for example, light emitting diodes), lenses 1234, light detectors 1236 (for example, photodiodes) and filters 1238. The detector comprises two LED's (blue and red, respectively) and two photodiodes. The two LED's are configured to transmit a beam of focused light on to a particular region of the cartridge. The two photodiodes are configured to receive light that is emitted from the region of the cartridge. One photodiode is configured to detect emitted red light, and the other photodiode is configured to detect emitted blue light. Thus, in this embodiment, two colors can be detected simultaneously from a single location. Such a detection system can be configured to receive light from multiple microfluidic channels by being mounted on an assembly that permits it to slide over and across the multiple channels. The filters can be, for example, bandpass filters, the filters at the light sources corresponding to the absorption band of one or more fluorogenic probes and the filters at the detectors corresponding to the emission band of the fluorogenic probes.

Figure 5:
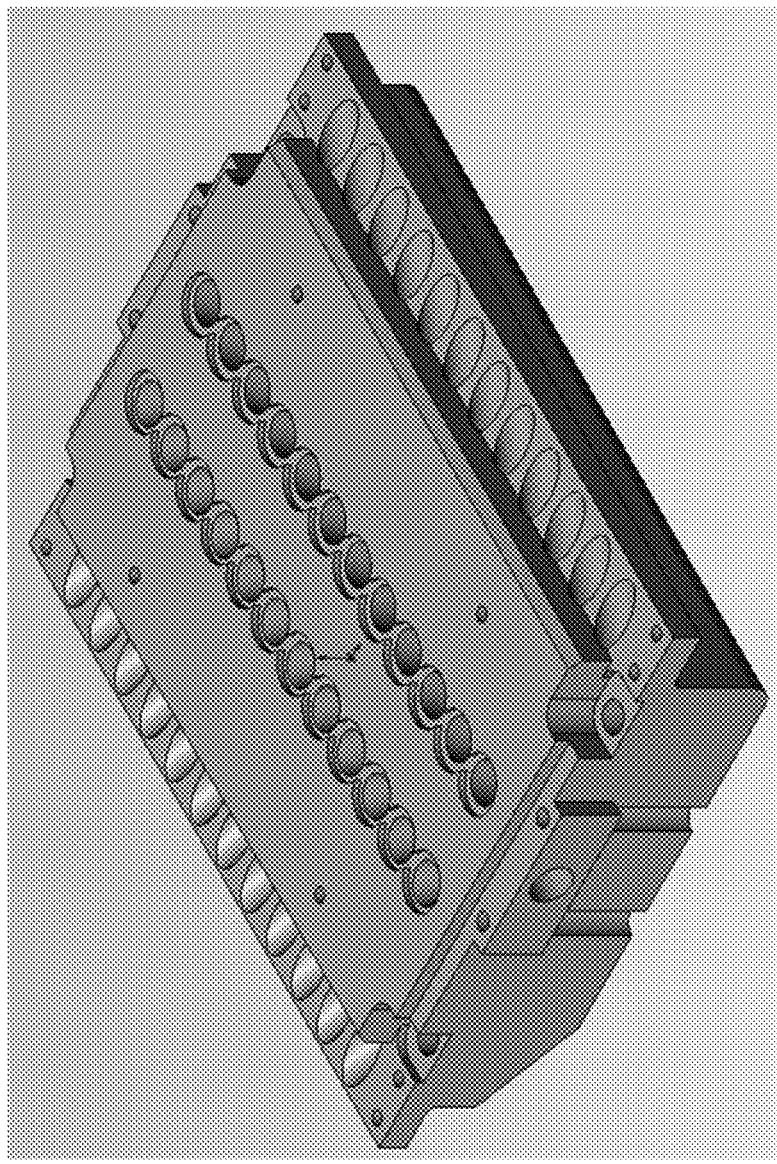
FIG. 5 shows an exterior view of an exemplary multiplexed read-head with an array of detectors therein.
Figure 6:
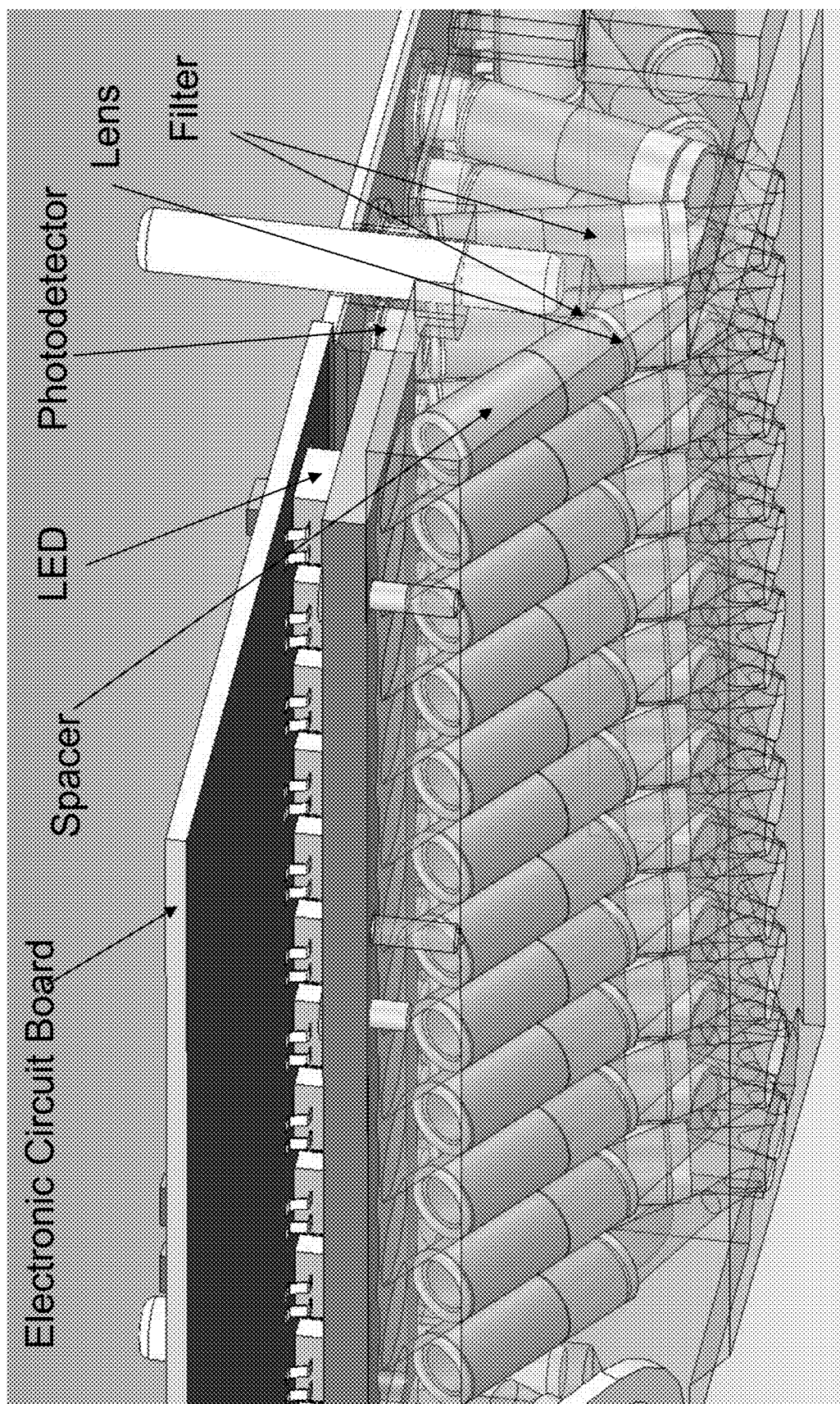
FIG. 6 shows a cutaway view of an exemplary multiplexed read-head, as in FIG. 5.

FIGS. 5 and 6 show an exemplary read-head comprising a multiplexed 2 color detection system that is configured to mate with a multi-lane microfluidic cartridge. FIG. 5 shows a view of the exterior of a multiplexed read-head. FIG. 6 is an exploded view that shows how various detectors are configured within an exemplary multiplexed read head, and in communication with an electronic circuit board.

Each of the detection systems multiplexed in the assembly of FIGS. 5 and 6 is similar in construction to the embodiment of FIGS. 2-4B. The module in FIGS. 5 and 6 is configured to detect fluorescence from each of 12 microfluidic channels, as found in, for example, the respective lanes of a 12-lane microfluidic cartridge. Such a module therefore comprises 24 independently controllable detectors, arranged as 12 pairs of identical detection elements. Each pair of elements is then capable of dual-color detection of a predetermined set of fluorescent probes. It would be understood by one of ordinary skill in the art that other numbers of pairs of detectors are consistent with the apparatus described herein. For example, 4, 6, 8, 10, 16, 20, 24, 25, 30, 32, 36, 40, and 48 pairs are also consistent and can be configured according to methods and criteria understood by one of ordinary skill in the art.

Detection Sensitivity, Time Constant and Gain

Figure 7:
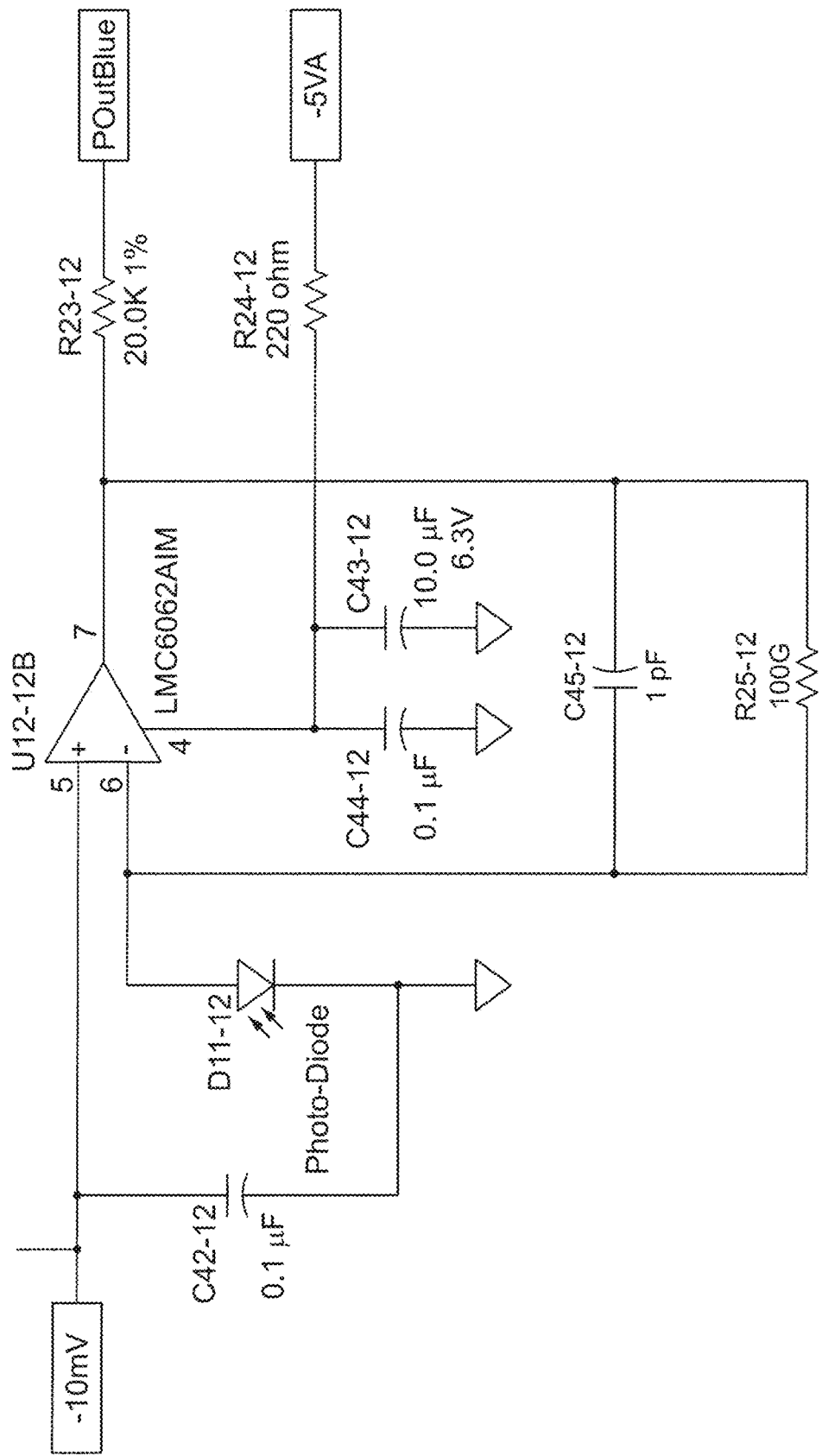
FIG. 7 shows exemplary pre-amplifier circuitry for a fluorescence detector.

A typical circuit that includes a detector as described herein includes, in series, a preamplifier, a buffer/inverter, a filter, and a digitizer. Sensitivity is important so that high gain is very desirable. In one embodiment of the preamplifier, a very large, for example 100 GΩ, resistor is placed in parallel with the diode. Other values of a resistor would be consistent with the technology herein: such values typically fall in the range 0.5-100 GΩ, such as 1-50 GΩ, or 2-10 GΩ. An exemplary pre-amplifier circuit configured in this way is shown in FIG. 7. Symbols in the figure have their standard meanings in electronic circuit diagrams.

The FIG. 7 shows a current-to-voltage converter/pre-amplifier circuit suitable for use with the detection system. D11 is the photodetector that collects the fluorescent light coming from the microfluidic channel and converts it into an electric current. The accompanying circuitry is used to convert these fluorescent currents into voltages suitable for measurement and output as a final measure of the fluorescence.

A resistor-capacitor circuit in FIG. 7 contains capacitor C45 and resistor R25. Together, the values of capacitance of C45 and resistance of R25 are chosen so as to impact the time constant $\tau_c$ (equal to the product of R25 and C45) of the circuit as well as gain of the detection circuit. The higher the time constant, the more sluggish is the response of the system to incident light. It typically takes the duration of a few time constants for the photodetector to completely charge to its maximum current or to discharge to zero from its saturation value. It is important for the photo current to decay to zero between measurements, however. As the PCR systems described herein are intended to afford rapid detection measurements, the product $R_{25}C_{45}$ should therefore be made as low as possible. However, the gain of the pre-amplifier whose circuitry is shown is directly proportional to the (fluorescent-activated) current generated in the photo-detector and the resistance $R_{25}$. As the fluorescence signal from the microfluidic channel device is very faint (due to low liquid volume as well as small path lengths of excitation), it is thus important to maximize the value of $R_{25}$. In some embodiments, $R_{25}$ is as high as 100 Giga-Ohms (for example, in the range 10-100 GΩ), effectively behaving as an open-circuit. With such values, the time-constant can take on a value of approximately 50-100 ms by using a low-value capacitor for C45. For example, the lowest possible available standard off-the-shelf capacitor has a value of 1 pF (1 picoFarad). A time-constant in the range 50-100 ms ensures that the photocurrent decays to zero in approximately 0.5 s (approx. 6 cycles) and therefore that approximately 2 samplings can be made per second. Other time constants are consistent with effective use of the technology herein, such as in the range 10 ms-1 s, or in the range 50 ms-500 ms, or in the range 100-200 ms. The actual time constant suitable for a given application will vary according to circumstance and choice of capacitor and resistor values. Additionally, the gain achieved by the pre-amplifier circuit herein may be in the range of $10^7$–$5 \times 10^9$, for example may be $1 \times 10^9$.

As the resistance value for R25 is very high (~100 GΩ), the manner of assembly of this resistor on the optics board is important for the overall efficiency of the circuit. Effective cleaning of the circuit during assembly and before use is important to achieve an optimal time-constant and gain for the optics circuit.

It is also important to test each photo-diode that is used, because many do not perform according to specification.

Sensitivity and Aperturing

The LED light passes through a filter before passing through the sample in the micro-fluidic channel (as described herein, typically 300 T deep). This is a very small optical path-length for the light in the sample. The generated fluorescence then also goes through a second filter, and into a photo-detector. Ultimately, then, the detector must be capable of detecting very little fluorescence. Various aspects of the detector configuration can improve sensitivity, however.

Figure 8B:
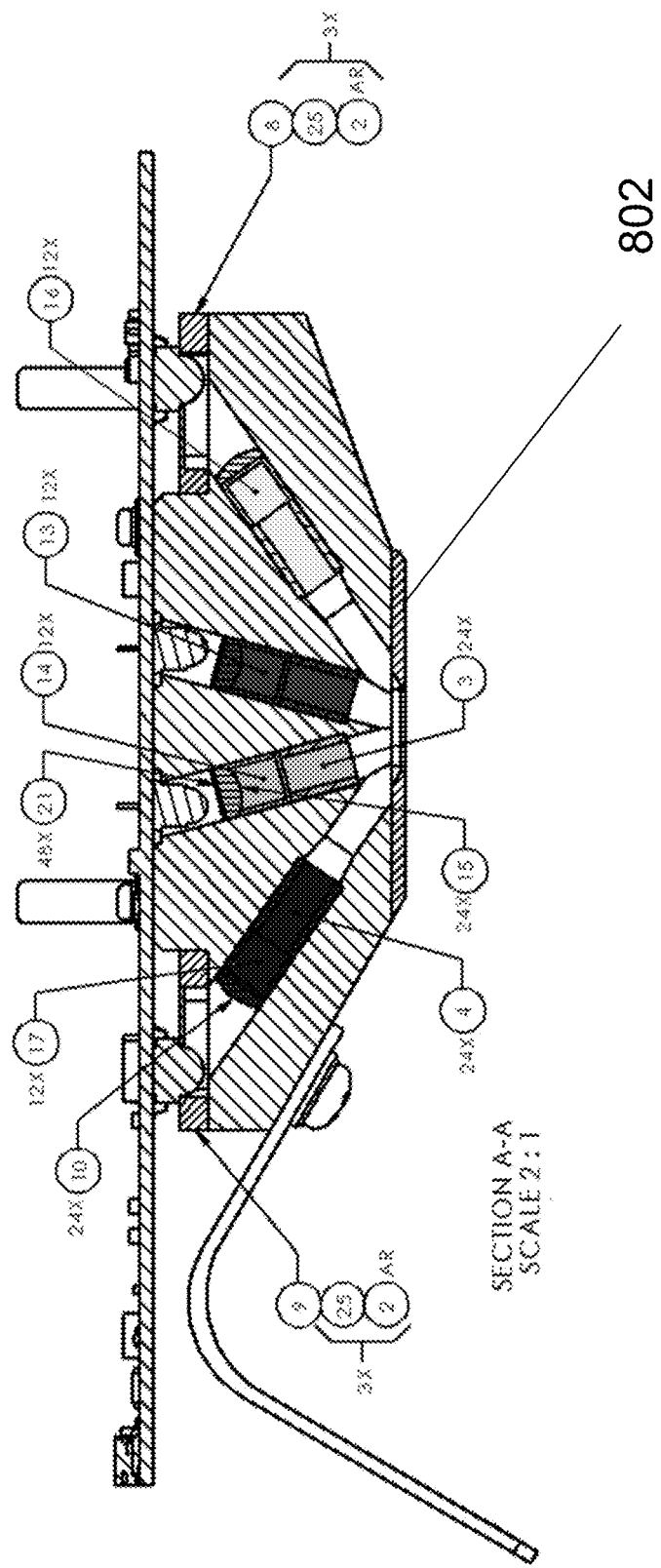
FIG. 8B shows a detector in cross section with an exemplary aperture.

The illumination optics can be designed so that the excitation light falling on the PCR reactor is incident along an area that is similar to the shape of the reactor. As the reactor is typically long and narrow, the illumination spot should be long and narrow, i.e., extended, as well. The length of the spot can be adjusted by altering a number of factors, including: the diameter of the bore where the LED is placed (the tube that holds the filter and lens has an aperturing effect); the distance of the LED from the PCR reactor; and the use of proper lens at the right distance in between. As the width of the beam incident on the reactor is determined by the bore of the optical element (approximately 6 mm in diameter), it is typical to use an aperture (a slit having a width approximately equal to the width of the reactor, and a length equal to the length of the detection volume) to make an optimal illumination spot. A typical spot, then, is commensurate with the dimensions of a PCR reaction chamber, for example 1.5 mm wide by 7 mm long. FIG. 8A shows the illumination spot across 12 PCR reactors for the two different colors used. A typical aperture is made of anodized aluminum and has very low autofluorescence in the wavelengths of interest. FIG. 8B illustrates a cross-section of a detector, showing an exemplary location for an aperture 802.

The optimal spot size and intensity is importantly dependent on the ability to maintain the correct position of the LED's with respect to the center of the optical axis. Special alignment procedures and checks can be utilized to optimize this. The different illuminations can also be normalized with respect to each other by adjusting the power current through each of the LED's or adjusting the fluorescence collection time (the duration for which the photodetector is on before measuring the voltage) for each detection spot. It is also important to align the detectors with the axis of the microchannels.

The aperturing is also important for successful fluorescence detection because as the cross-sectional area of the incident beam increases in size, so the background fluorescence increases, and the fluorescence attributable only to the molecules of interest (PCR probes) gets masked. Thus, as the beam area increases, the use of an aperture increases the proportion of collected fluorescence that originates only from the PCR reactor. Note that the aperture used in the detector herein not only helps collect fluorescence only from the reaction volume but it correspondingly adjusts the excitation light to mostly excite the reaction volume. The excitation and emission aperture is, of course, the same.

Based on a typical geometry of the optical excitation and emission system and aperturing, show spot sizes as small as 0.5 mm by 0.5 mm and as long as 8 mm×1.5 mm have been found to be effective. By using a long detector (having an active area 6 mm by 1 mm) and proper lensing, the aperture design can extend the detection spot to as long as 15-20 mm, while maintaining a width of 1-2 mm using an aperture. Correspondingly, the background fluorescence decreases as the spot size is decreased, thereby increasing the detection sensitivity.

Use of Detection System to Measure/Detect Fluid in PCR Chamber

The fluorescence detector is sensitive enough to be able to collect fluorescence light from a PCR chamber of a microfluidic substrate. The detector can also be used to detect the presence of liquid in the chamber, a measurement that provides a determination of whether or not to carry out a PCR cycle for that chamber. For example, in a multi-sample cartridge, not all chambers will have been loaded with sample; for those that are not, it would be unnecessary to apply a heating protocol thereto. One way to determine presence or absence of a liquid is as follows. A background reading is taken prior to filling the chamber with liquid. Another reading is taken after microfluidic operations have been performed that should result in filling the PCR chamber with liquid. The presence of liquid alters the fluorescence reading from the chamber. A programmable threshold value can be used to tune an algorithm programmed into a processor that controls operation of the apparatus as further described herein (for example, the second reading has to exceed the first reading by 20%). If the two readings do not differ beyond the programmed margin, the liquid is deemed to not have entered the chamber, and a PCR cycle is not initiated for that chamber. Instead, a warning is issued to a user.

Microfluidic Cartridge

Where the microfluidic channels that contain analytes detected by the detection system are situated in a microfluidic cartridge, the cartridge typically has attributes as follows. The microfluidic cartridge is designed so that it receives thermal energy from one or more heating elements present in the heater unit described elsewhere herein when it is in thermal communication therewith. The heater unit may be part of an apparatus, configured to receive the cartridge, and comprising other features such as control circuitry, user interface, and detector, as well as still other features. An exemplary such apparatus is further described herein; additional embodiments of such a apparatus are found in U.S. patent application Ser. No. 11/985,577, entitled "Microfluidic System for Amplifying and Detecting Polynucleotides in Parallel", and filed on even date herewith, the specification of which is incorporated herein by reference.

By cartridge is meant a unit that may be disposable, or reusable in whole or in part, and that is configured to be used in conjunction with some other apparatus that has been suitably and complementarily configured to receive and operate on (such as deliver energy to via a heater module as described herein) the cartridge.

One aspect of the present technology relates to a detector that is configured to selectively detect analytes in a microfluidic cartridge having two or more sample lanes arranged so that analyses can be carried out in two or more of the lanes in parallel, for example simultaneously, and wherein each lane is independently associated with a given sample.

A sample lane, as found in a microfluidic cartridge, is an independently controllable set of elements by which a sample can be analyzed, for example by carrying out PCR on a sample in which the presence or absence of one or more polynucleotides is to be determined, according to methods described in, e.g., U.S. patent application Ser. No. 11/940,310, entitled "Microfluidic Cartridge and Method of Making Same", and filed on even date herewith. A sample lane comprises at least a sample inlet, and a microfluidic network having one or more microfluidic components, as further described herein.

In various embodiments, a sample lane of a microfluidic cartridge can include a sample inlet port or valve, and a microfluidic network that comprises, in fluidic communication one or more components selected from the group consisting of: at least one thermally actuated valve, a bubble removal vent, at least one gate, at least one thermally actuated pump, a downstream thermally actuated valve, mixing channels, one or more positioning elements, and a PCR reaction zone. The detector described herein can be configured to detect light emitted from any one of the foregoing microfluidic components, but is typically configured to detect light from a reaction chamber.

In various embodiments, the microfluidic network can be configured to couple heat from an external heat source, such as provided by a heater unit described elsewhere herein, to a sample mixture comprising PCR reagent and neutralized polynucleotide sample under thermal cycling conditions suitable for creating PCR amplicons from the neutralized polynucleotide sample.

A multi-lane cartridge is typically configured to accept a number of samples in series or in parallel, in particular embodiments 12 samples and in other embodiments 24, or 48 samples, wherein the samples include at least a first sample and a second sample, wherein the first sample and the second sample each contain one or more polynucleotides in a form suitable for amplification. The polynucleotides in question may be the same as, or different from one another, in different samples and hence in different lanes of the cartridge. The cartridge typically processes each sample by increasing the concentration of a polynucleotide to be determined and/or by reducing the concentration of inhibitors relative to the concentration of polynucleotide to be determined.

Exemplary Microfluidic Cartridges

Figure 9A:
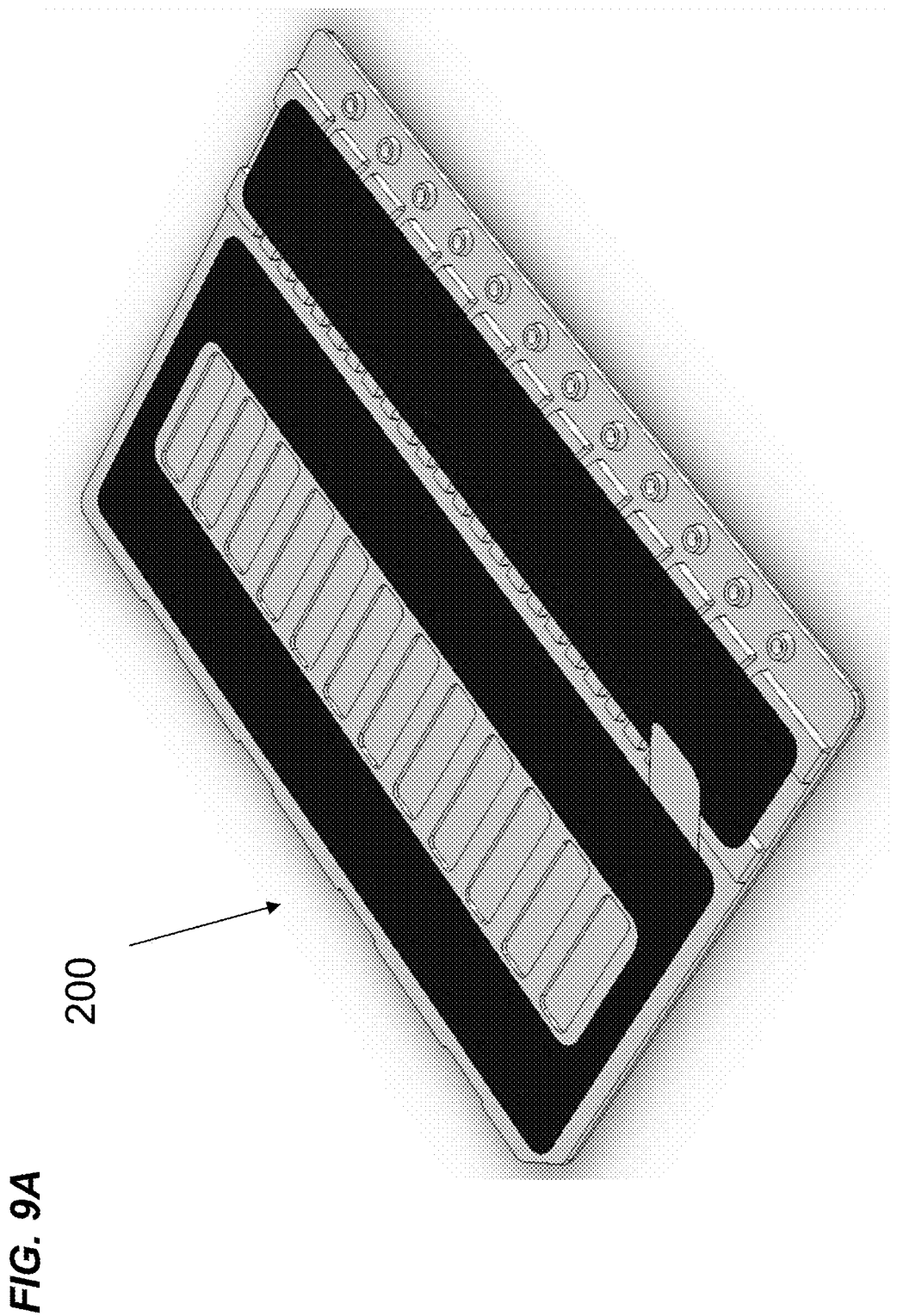
FIG. 9A shows an exemplary multi-lane cartridge.
Figure 9B:
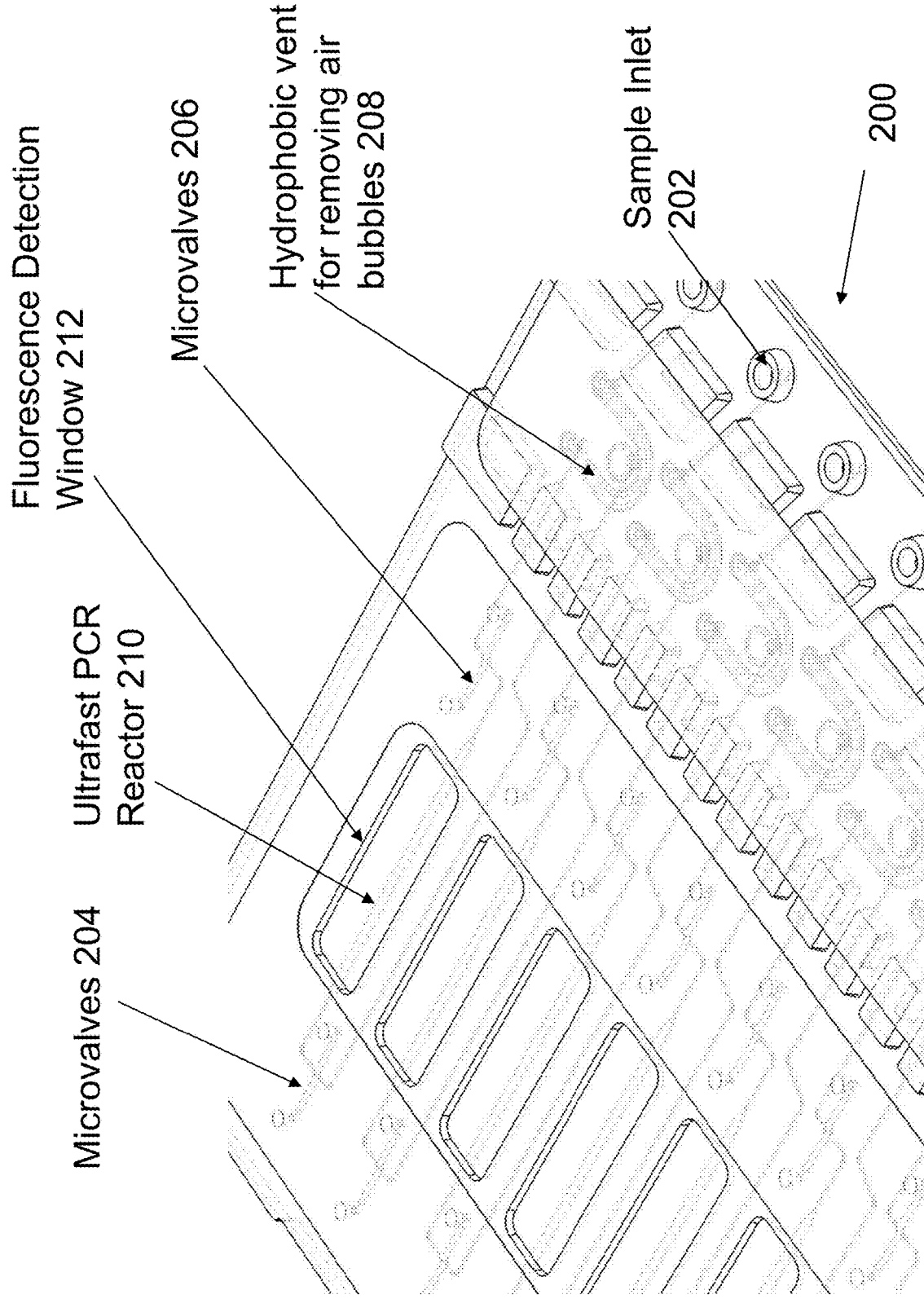
FIG. 9B shows a portion of an exemplary multi-lane cartridge.

FIG. 9A shows a perspective view of a portion of an exemplary microfluidic cartridge 200 according to the present technology. FIG. 9B shows a close-up view of a portion of the cartridge 200 of FIG. 9A illustrating various representative components. The cartridge 200 may be referred to as a multi-lane PCR cartridge with dedicated sample inlets 202. For example sample inlet 202 is configured to accept a liquid transfer member (not shown) such as a syringe, a pipette, or a PCR tube containing a PCR ready sample. More than one inlet 202 is shown in FIGS. 9A, 9B, wherein one inlet operates in conjunction with a single sample lane. Various components of microfluidic circuitry in each lane are also visible. For example, microvalves 204, and 206, and vents 208, are parts of microfluidic circuitry in a given lane. Microfluidic circuitry is typically disposed within a microfluidic substrate found in one or more layers of the cartridge.

Also shown is an ultrafast PCR reactor 210, which, as further described herein, is a microfluidic channel in a given sample lane that is long enough to permit PCR to amplify polynucleotides present in a sample. Above each PCR reactor 210 is a window 212 that permits detection of fluorescence from a fluorescent substance in PCR reactor 210 when a detector is situated above window 212. It is to be understood that other configurations of windows are possible including, but not limited to, a single window that straddles each PCR reactor across the width of cartridge 200.

A multi-sample cartridge comprises at least a first microfluidic network and a second microfluidic network, adjacent to one another, wherein each of the first microfluidic network and the second microfluidic network is as elsewhere described herein, and wherein the first microfluidic network accepts the first sample, and wherein the second microfluidic network accepts the second sample.

In some embodiments, the multi-sample cartridge has a size substantially the same as that of a 96-well plate as is customarily used in the art. Advantageously, then, the cartridge may be used with plate handlers used elsewhere in the art.

The sample inlets of adjacent sample lanes in a multi-sample cartridge are reasonably spaced apart from one another to prevent any contamination of one sample inlet from another sample when a user introduces a sample into any one cartridge. In an embodiment, the sample inlets are configured so as to prevent subsequent inadvertent introduction of sample into a given lane after a sample has already been introduced into that lane. Thus, the elements of the detector described herein are engineered to be compatible with the overall cartridge size and the separation between the respective lanes.

In other embodiments, the multi-sample cartridge is designed so that a spacing between the centroids of sample inlets is 9 mm, which is an industry-recognized standard. This means that, in certain embodiments the center-to-center distance between inlet holes in the cartridge that accept samples from PCR tubes, as further described herein, is 9 mm. The inlet holes are manufactured conical in shape with an appropriate conical angle so that industry-standard pipette tips (2 µl, 20 µl, 200 µl, volumes, etc.) fit snugly. The apparatus herein may be adapted to suit other, later-arising, industry standards not otherwise described herein.

Figure 10:
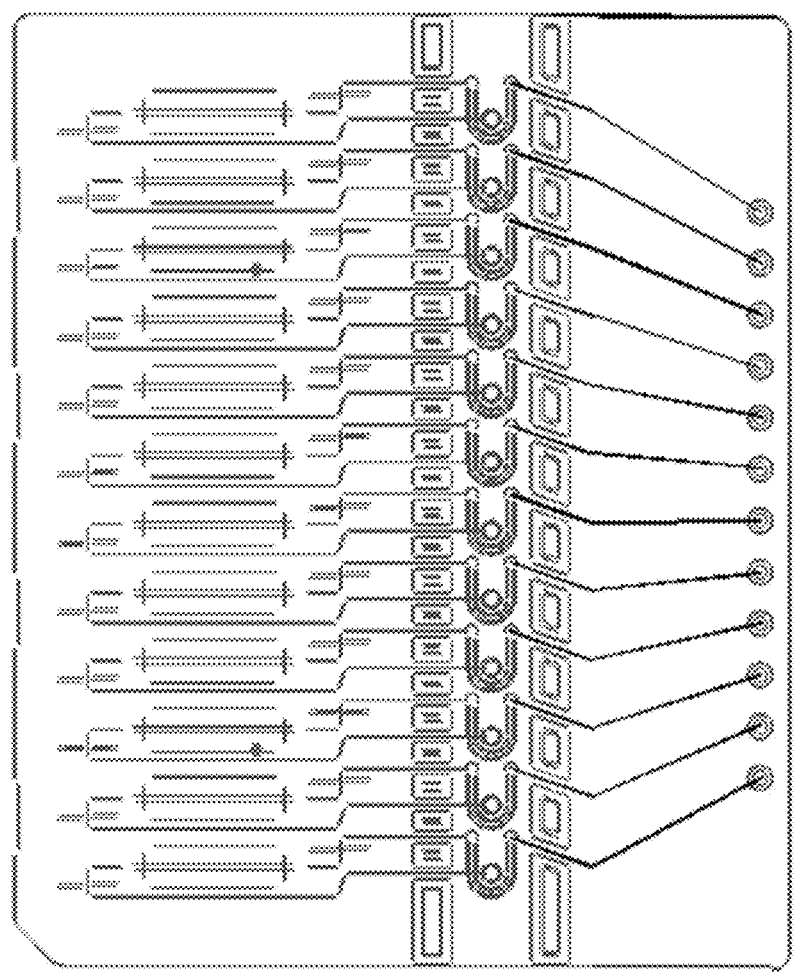
FIG. 10 shows a plan of microfluidic circuitry and inlets in an exemplary multi-lane cartridge.

FIG. 10 shows a plan view of an exemplary microfluidic cartridge having 12 lanes. The inlet ports have a 6 mm spacing, so that, when used in conjunction with an automated sample loader having 4 heads, spaced equidistantly at 18 mm apart, the inlets can be loaded in three batches of 4 inlets: e.g., inlets 1, 4, 7, and 10 together, followed by 2, 5, 8, and 11, then finally 3, 6, 9, and 12, wherein the 12 inlets are numbered consecutively from one side of the cartridge to the other.

In use, cartridge 200 is typically thermally associated with an array of heat sources configured to operate the components (e.g., valves, gates, actuators, and processing region 210) of the device. Particular components of exemplary microfluidic networks are further described in U.S. patent application Ser. No. 11/940,310, entitled "Microfluidic Cartridge and Method of Making Same" and filed on even date herewith.

Figure 11:
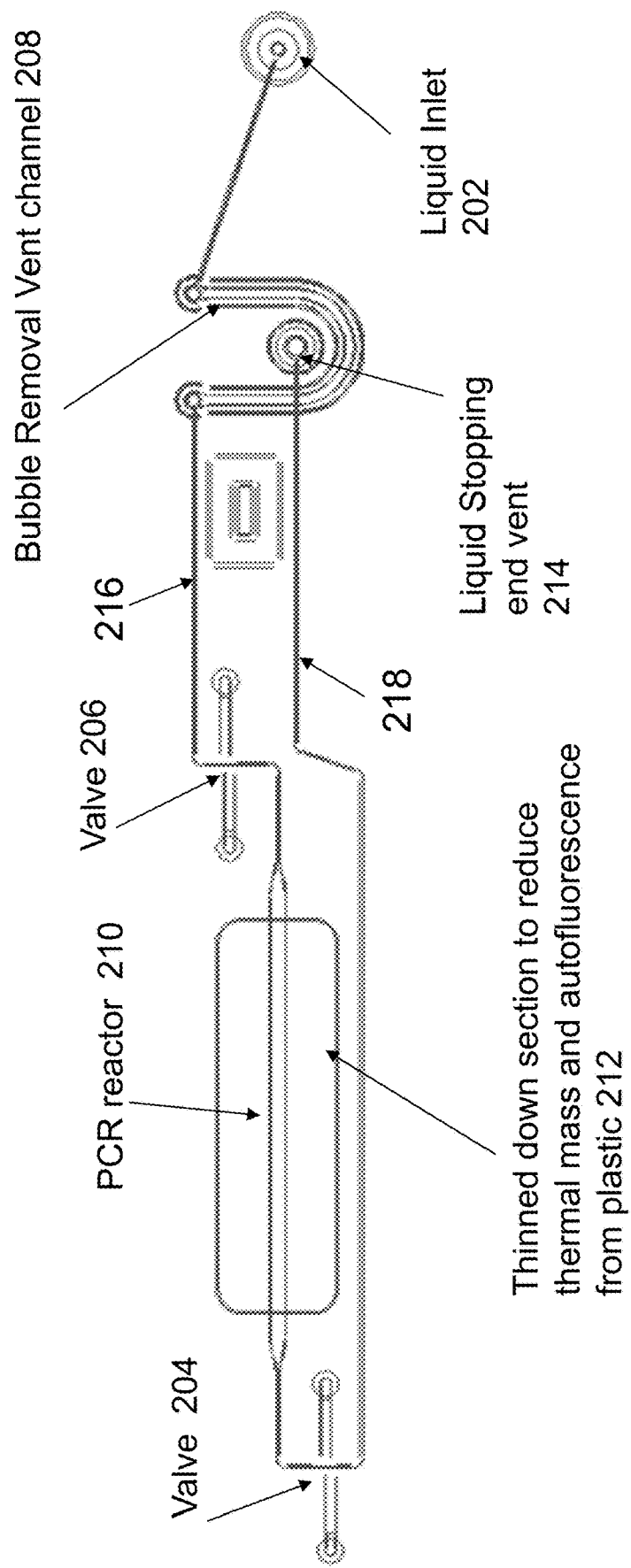
FIG. 11 shows an exemplary microfluidic network in a lane of a multi-lane cartridge.

FIG. 11 shows a plan view of a representative microfluidic circuit found in one lane of a multi-lane cartridge such as shown in FIG. 10. Other configurations of microfluidic network would be consistent with the function of the cartridges and apparatus described herein. In sequence, sample is introduced through liquid inlet 202, flows into a bubble removal vent channel 208 (which permits adventitious air bubbles introduced into the sample during entry, to escape), and continues along a channel 216. Throughout the operation of cartridge 200 the fluid is manipulated as a microdroplet (not shown in FIG. 5), and the various microfluidic components are actuated or controlled by application of heat from the heater unit further described herein. Valves 204 and 206 are initially open, so that a microdroplet of sample-containing fluid can be pumped into PCR reactor channel 210 from inlet hole 202. Upon initiating of processing, the detector present on top of the PCR reactor checks for the presence of liquid in the PCR channel, and then closes valves 204 and 206 to isolate the PCR reaction mix from the outside. The reactor 210 is a microfluidic channel that is heated through a series of cycles to carry out amplification of nucleotides in the sample, as further described herein. Both valves 204 and 206 are closed prior to thermocycling to prevent any evaporation of liquid, bubble generation, or movement of fluid from the PCR reactor. End vent 214 prevents a user from introducing any excess amount of liquid into the microfluidic cartridge, as well as playing a role of containing any sample from spilling over to unintended parts of the cartridge. A user may input sample volumes as small as an amount to fill from the bubble removal vent to the middle of the microreactor, or up to valve 204 or beyond valve 204. The use of microvalves prevents both loss of liquid or vapor thereby enabling even a partially filled reactor to successfully complete a PCR thermocycling reaction.

The cartridge can further include a heat sealable laminate layer (typically between about 100 and about 125 microns thick) attached to the bottom surface of a microfluidic substrate using, for example, heat bonding. The cartridge can further include a thermal interface material layer (typically about 125 microns thick), attached to the bottom of the heat sealable laminate layer using, for example, pressure sensitive adhesive. This layer can be compressible and have a higher thermal conductivity than common plastics, thereby serving to transfer heat across the membrane more efficiently to the components of the microfluidic network.

The application of pressure to contact the cartridge to the heater unit assists in achieving better thermal contact between the heater and the heat-receivable parts of the cartridge, and also prevents the bottom laminate structure—where present—from expanding, as would happen if the PCR channel was partially filled with liquid so that the entrapped air would be thermally expanded during thermocycling.

Further aspects of a microfluidic cartridge that adapt it to carrying out PCR efficiently are described in U.S. patent application Ser. No. 11/940,310, entitled "Microfluidic Cartridge and Method of Making Same" and filed on even date herewith, the specification of which is incorporated herein by reference.

Microfluidic cartridge 200 can be fabricated as desired, for example, according to methods described in U.S. patent application Ser. No. 11/940,310, entitled "Microfluidic Cartridge and Method of Making Same" and filed on even date herewith.

Highly Multiplexed Cartridge Embodiments

Embodiments of the apparatus and cartridge described herein may be constructed that have high-density microfluidic circuitry on a single cartridge that thereby permit processing of multiple samples in parallel, or in sequence, on a single cartridge. Preferred numbers of such multiple samples include 24, 36, 40, 48, 50, 60, 64, 72, 80, 84, 96, and 100, but it would be understood that still other numbers are consistent with the apparatus and cartridge herein, where deemed convenient and practical.

Accordingly, different configurations of lanes, sample inlets, and associated heater networks are contemplated that can facilitate processing such numbers of samples on a single cartridge are within the scope of the instant disclosure. Similarly, alternative configurations of detectors and heating elements for use in conjunction with such a highly multiplexed cartridge are also within the scope of the description herein.

It is also to be understood that the microfluidic cartridges and substrates described herein are not to be limited to rectangular configurations, but can include cartridges having circular, elliptical, triangular, rhombohedral, square, and other shapes. Such shapes may also be adapted to include some irregularity, such as a cut-out, to facilitate placement in a complementary apparatus as further described elsewhere herein.

Figure 12:
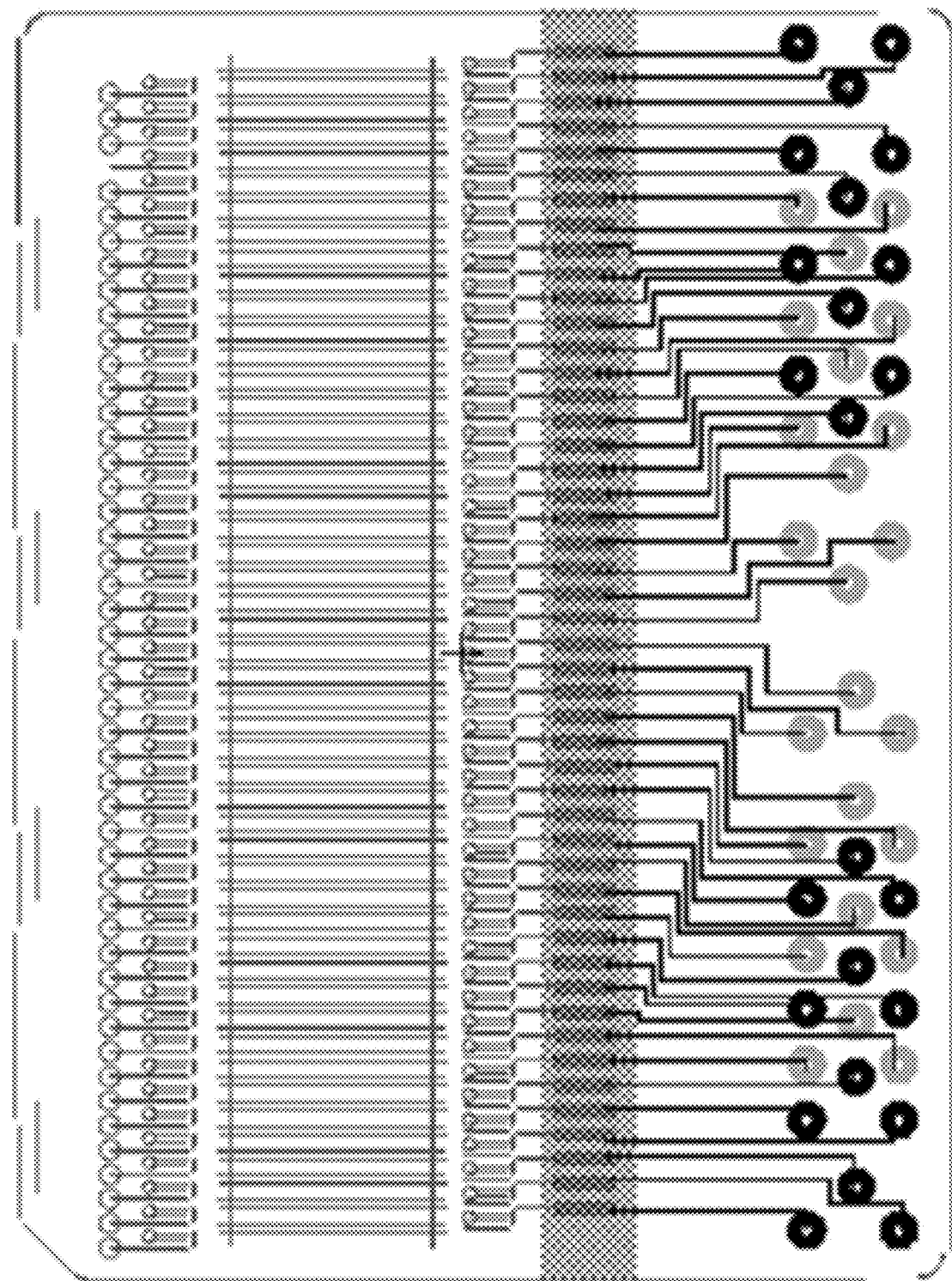
FIG. 12 shows an exemplary highly-multiplexed microfluidic cartridge.

FIG. 12 shows a representative 48-sample cartridge, and having an inlet configuration different from others described and depicted herein. The inlet configuration is exemplary and has been designed to maximize efficiency of space usage on the cartridge. The inlet configuration can be compatible with an automatic pipetting machine that has dispensing heads situated at a 9 mm spacing. For example, such a machine having 4 heads can load 4 inlets at once, in 12 discrete steps, for the cartridge of FIG. 12. Other configurations of inlets though not explicitly described are compatible with the technology described herein.

Figure 13:
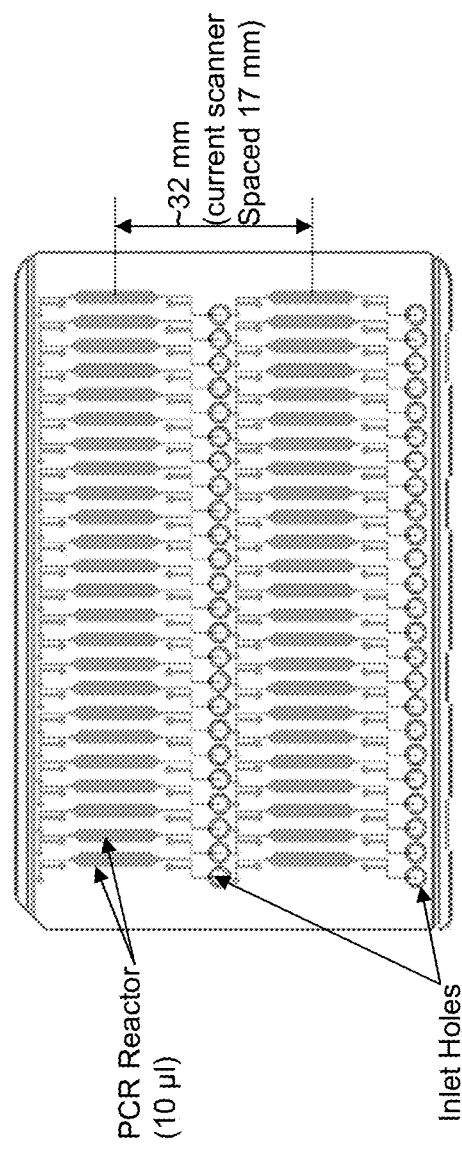
FIG. 13 shows an exemplary highly-multiplexed microfluidic cartridge.

In an exemplary embodiment, a highly multiplexed cartridge has 48 sample lanes, and permits independent control of each valve in each lane, with 2 banks of thermocycling protocols per lane, as shown in FIG. 13. This permits samples to be loaded into the cartridge at different times, and passed to the PCR reaction chambers independently of one another. Such embodiments permit batch processing of PCR samples, where multiple samples from different lanes are amplified by the same set of heating/cooling cycles. For example, the PCR heaters can be arranged in 2 banks (the heater arrays on the left and right are not in electrical communication with one another), thereby permitting a separate degree of sample control.

Figure 14:
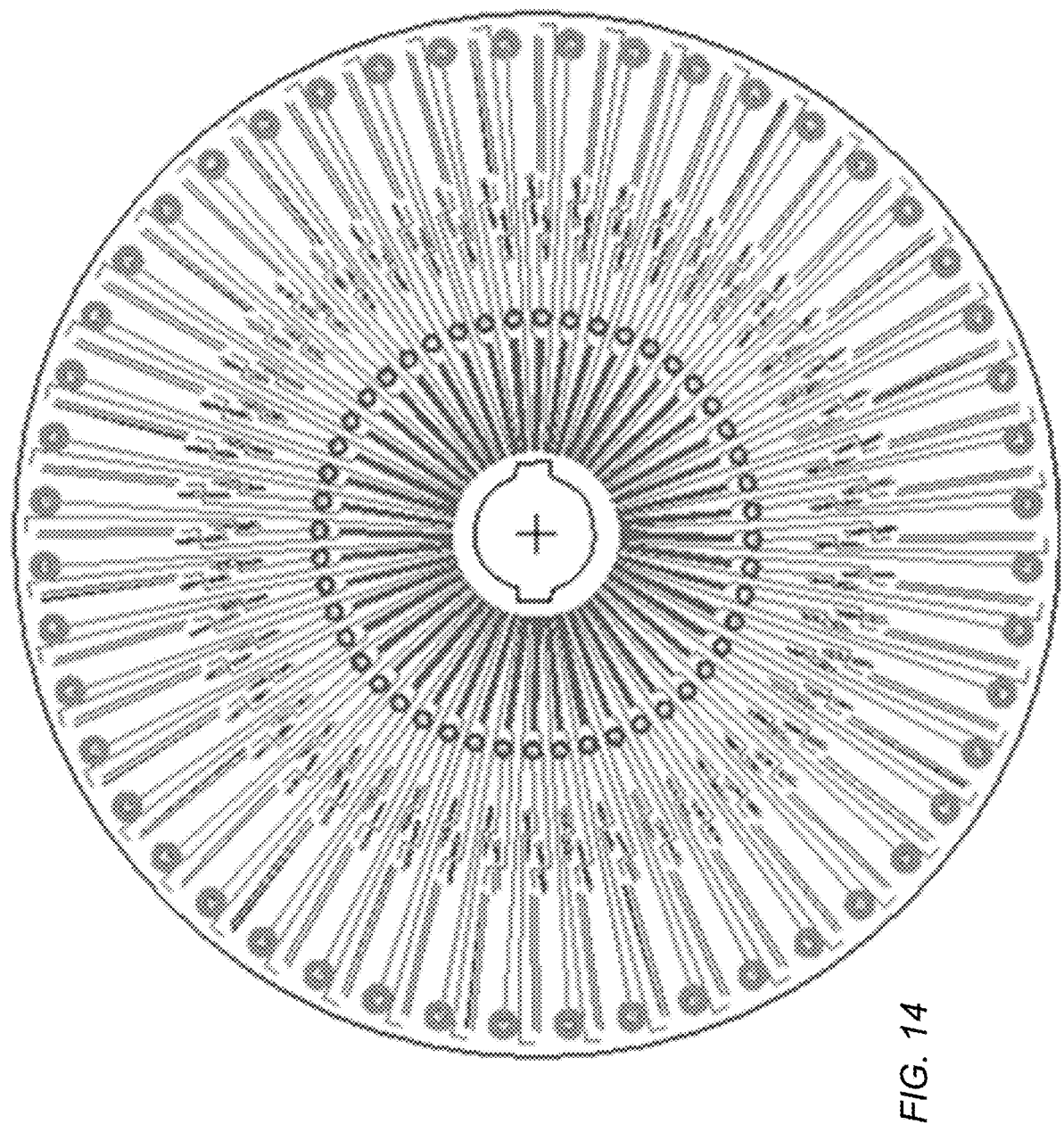
FIG. 14 shows a radially configured highly multiplexed microfluidic cartridge.

FIG. 14 shows an embodiment of a radially-configured highly-multiplexed cartridge, having a number of inlets, microfluidic lanes, and PCR reaction chambers.

The various embodiments shown in FIGS. 12-14 are compatible with liquid dispensers, receiving bays, heater units, and detectors that are configured differently from the other specific examples described herein. For example, such detectors may be configured to detect light from multiple sample lanes simultaneously, or to scan over sample lanes singly or in batches successively.

In another preferred embodiment (not shown in the FIGs.), a cartridge and apparatus is configured so that the read-head does not cover the sample inlets, thereby permitting loading of separate samples while other samples are undergoing PCR thermocycling.

PCR Reagent Mixtures

PCR reagent mixes, and methods of preparation and use thereof, are generally known in the art. Herein, general aspects of such methods are described, as they can be used with the apparatus and detection system. In various embodiments, the sample for introduction into a lane of the cartridge can include a PCR reagent mixture comprising a polymerase enzyme and a plurality of nucleotides, and at least one probe that selectively emits light detected by the detection system herein.

In various embodiments, preparation of a PCR-ready sample for use with an apparatus and cartridge as described herein can include contacting a neutralized polynucleotide sample with a PCR reagent mixture comprising a polymerase enzyme and a plurality of nucleotides (in some embodiments, the PCR reagent mixture can further include a positive control plasmid and a fluorogenic hybridization probe selective for at least a portion of the plasmid). Other aspects of suitable PCR reagent mixture, for example lyophilized formulations, are described in U.S. patent application Ser. No. 11/940,310, entitled "Microfluidic Cartridge and Method of Making Same", filed on even date herewith.

In various embodiments, the PCR-ready sample can include at least one probe that is selective for a polynucleotide sequence, e.g., the polynucleotide sequence that is characteristic of a pathogen selected from the group consisting of gram positive bacteria, gram negative bacteria, yeast, fungi, protozoa, and viruses. Steps by which such a PCR-ready sample is prepared involve contacting the neutralized polynucleotide sample or a PCR amplicon thereof with the probe. The probe can be a fluorogenic hybridization probe. The fluorogenic hybridization probe can include a polynucleotide sequence coupled to a fluorescent reporter dye and a fluorescence quencher dye.

In various embodiments, the PCR-ready sample further includes a sample buffer.

In various embodiments, the PCR reagent mixture can further include a polymerase enzyme, a positive control plasmid and a fluorogenic hybridization probe selective for at least a portion of the plasmid.

It is envisaged that the detection system herein is operable with any probe suitable for use in detecting a particular polynucleotide. The choice and use of a suitable probe is within the capability of one skilled in the art. In various embodiments, the probe can be selective for a polynucleotide sequence that is characteristic of an organism, for example any organism that employs deoxyribonucleic acid or ribonucleic acid polynucleotides. Thus, the probe can be selective for any organism. Suitable organisms include mammals (including humans), birds, reptiles, amphibians, fish, domesticated animals, wild animals, extinct organisms, bacteria, fungi, viruses, plants, and the like. The probe can also be selective for components of organisms that employ their own polynucleotides, for example mitochondria. In some embodiments, the probe is selective for microorganisms, for example, organisms used in food production (for example, yeasts employed in fermented products, molds or bacteria employed in cheeses, and the like) or pathogens (e.g., of humans, domesticated or wild mammals, domesticated or wild birds, and the like). In some embodiments, the probe is selective for organisms selected from the group consisting of gram positive bacteria, gram negative bacteria, yeast, fungi, protozoa, and viruses.

In various embodiments, the probe can be selective for a polynucleotide sequence that is characteristic of an organism selected from the group consisting of *Staphylococcus* spp., e.g., *S. epidermidis, S. aureus*, Methicillin-resistant *Staphylococcus aureus* (MRSA), Vancomycin-resistant *Staphylococcus; Streptococcus* (e.g., α, β or γ-hemolytic, Group A, B, C, D or G) such as *S. pyogenes, S. agalactiae; E. faecalis, E. durans*, and *E. faecium* (formerly *S. faecalis, S. durans, S. faecium*); nonenterococcal group D *streptococci*, e.g., *S. bovis* and *S. equines; Streptococci viridans*, e.g., *S. mutans, S. sanguis, S. salivarius, S. mitior, A. milleri, S. constellatus, S. intermedius*, and *S. anginosus; S. iniae; S. pneumoniae; Neisseria*, e.g., *N. meningitides, N. gonorrhoeae*, saprophytic *Neisseria* sp; *Erysipelothrix*, e.g., *E. rhusiopathiae;*

*Listeria* spp., e.g., *L. monocytogenes*, rarely *L. ivanovii* and *L. seeligeri*; *Bacillus*, e.g., *B. anthracis*, *B. cereus*, *B. subtilis*, *B. subtilis niger*, *B. thuringiensis*; *Nocardia asteroids*; *Legionella*, e.g., *L. pneumophila*, *Pneumocystis*, e.g., *P. carinii*; *Enterobacteriaceae* such as *Salmonella*, *Shigella*, *Escherichia* (e.g., *E. coli*, *E. coli*O157:H7); *Klebsiella*, *Enterobacter*, *Serratia*, *Proteus*, *Morganella*, *Providencia*, *Yersinia*, and the like, e.g., *Salmonella*, e.g., *S. typhi* *S. paratyphi* A, B (*S. schottmuelleri*), and C (*S. hirschfeldii*), *S. dublin* *S. choleraesuis*, *S. enteritidis*, *S. typhimurium*, *S. heidelberg*, *S. newport*, *S. infantis*, *S. agona*, *S. montevideo*, and *S. saint-paul*; *Shigella* e.g., subgroups: A, B, C, and D, such as *S. flexneri*, *S. sonnei*, *S. boydii*, *S. dysenteriae*; *Proteus* (*P. mirabilis*, *P. vulgaris*, and *P. myxofaciens*), *Morganella* (*M. morganii*); *Providencia* (*P. rettgeri*, *P. alcalifaciens*, and *P. stuartii*); *Yersinia*, e.g., *Y. pestis*, *Y. enterocolitica*; *Haemophilus*, e.g., *H. influenzae*, *H. parainfluenzae* *H. aphrophilus*, *H. ducreyi*; *Brucella*, e.g., *B. abortus*, *B. melitensis*, *B. suis*, *B. canis*; *Francisella*, e.g., *F. tularensis*; *Pseudomonas*, e.g., *P. aeruginosa*, *P. paucimobilis*, *P. putida*, *P. fluorescens*, *P. acidovorans*, *Burkholderia* (*Pseudomonas*) *pseudomallei*, *Burkholderia mallei*, *Burkholderia cepacia* and *Stenotrophomonas maltophilia*; *Campylobacter*, e.g., *C. fetus* fetus, *C. jejuni*, *C. pylori* (*Helicobacter pylori*); *Vibrio*, e.g., *V. cholerae*, *V. parahaemolyticus*, *V. mimicus*, *V. alginolyticus*, *V. hollisae*, *V. vulnificus*, and the nonagglutinable vibrios; *Clostridia*, e.g., *C. perfringens*, *C. tetani*, *C. difficile*, *C. botulinum*; *Actinomyces*, e.g., *A. israelii*; *Bacteroides*, e.g., *B. fragilis*, *B. thetaiotaomicron*, *B. distasonis*, *B. vulgatus*, *B. ovatus*, *B. caccae*, and *B. merdae*; *Prevotella*, e.g., *P. melaninogenica*; genus *Fusobacterium*; *Treponema*, e.g. *T. pallidum* subspecies endemicum, *T. pallidum* subspecies pertenue, *T. carateum*, and *T. pallidum* subspecies pallidum; genus *Borrelia*, e.g., *B. burgdorferi*; genus *Leptospira*; *Streptobacillus*, e.g., *S. moniliformis*; *Spirillum*, e.g., *S. minus*; Mycobacterium, e.g., *M. tuberculosis*, *M. bovis*, *M. africanum*, *M. avium* *M. intracellulare*, *M. kansasii*, *M. xenopi*, *M. marinum*, *M. ulcerans*, the *M. fortuitum* complex (*M. fortuitum* and *M. chelonae*), *M. leprae*, *M. asiaticum*, *M. chelonae* subsp. abscessus, *M. fallax*, *M. fortuitum*, *M. malmoense*, *M. shimoidei*, *M. simiae*, *M. szulgai*, *M. xenopi*; Mycoplasma, e.g., *M. hominis*, *M. orale*, *M. salivarium*, *M. fermentans*, *M. pneumoniae*, *M. bovis*, *M. tuberculosis*, *M. avium*, *M. leprae*; *Mycoplasma*, e.g., *M. genitalium*; *Ureaplasma*, e.g., *U. urealyticum*; *Trichomonas*, e.g., *T. vaginalis*; *Cryptococcus*, e.g., *C. neoformans*; *Histoplasma*, e.g., *H. capsulatum*; *Candida*, e.g., *C. albicans*; *Aspergillus* sp; *Coccidioides*, e.g., *C. immitis*; *Blastomyces*, e.g. *B. dermatitidis*; *Paracoccidioides*, e.g., *P. brasiliensis*; *Penicillium*, e.g., *P. marneffei*; *Sporothrix*, e.g., *S. schenckii*; *Rhizopus*, *Rhizomucor*, *Absidia*, and *Basidiobolus*; diseases caused by *Bipolaris*, *Cladophialophora*, *Cladosporium*, *Drechslera*, *Exophiala*, *Fonsecaea*, *Phialophora*, *Xylohypha*, *Ochroconis*, *Rhinocladiella*, *Scolecobasidium*, and *Wangiella*; *Trichosporon*, e.g., *T. beigelii*; *Blastoschizomyces*, e.g., *B. capitatus*; *Plasmodium*, e.g., *P. falciparum*, *P. vivax*, *P. ovale*, and *P. malariae*; *Babesia* sp; protozoa of the genus *Trypanosoma*, e.g., *T. cruzi*; *Leishmania*, e.g., *L. donovani*, *L. major* *L. tropica*, *L. mexicana*, *L. braziliensis*, *L. viannia braziliensis*; *Toxoplasma*, e.g., *T. gondii*; Amoebas of the genera *Naegleria* or *Acanthamoeba*; *Entamoeba histolytica*; *Giardia lamblia*; genus *Cryptosporidium*, e.g., *C. parvum*; *Isospora belli*; *Cyclospora cayetanensis*; *Ascaris lumbricoides*; *Trichuris trichiura*; *Ancylostoma duodenale* or *Necator americanus*; *Strongyloides stercoralis* *Toxocara*, e.g., *T. canis*, *T. cati*; *Baylisascaris*, e.g., *B. procyonis*; *Trichinella*, e.g., *T. spiralis*; *Dracunculus*, e.g., *D. medinensis*; genus *Filarioidea*; *Wuchereria bancrofti*; *Brugia*, e.g., *B. malayi*, or *B. timori*; *Onchocerca volvulus*; *Loa loa*; *Dirofilaria immitis*; genus *Schistosoma*, e.g., *S. japonicum*, *S. mansoni*, *S. mekongi*, *S. intercalatum*, *S. haematobium*; *Paragonimus*, e.g., *P. Westermani*, *P. Skrjabini*; *Clonorchis sinensis*; *Fasciola hepatica*; *Opisthorchis sp*; *Fasciolopsis buski*; *Diphyllobothrium latum*; *Taenia*, e.g., *T. saginata*, *T. solium*; *Echinococcus*, e.g., *E. granulosus*, *E. multilocularis*; Picornaviruses, rhinoviruses echoviruses, coxsackieviruses, influenza virus; paramyxoviruses, e.g., types 1, 2, 3, and 4; adenoviruses; Herpesviruses, e.g., HSV-1 and HSV-2; varicella-zoster virus; human T-lymphotropicvirus (type I and type II); Arboviruses and Arenaviruses; Togaviridae, Flaviviridae, Bunyaviridae, Reoviridae; Flavivirus; Hantavirus; Viral encephalitis (alphaviruses [e.g., Venezuelan equine encephalitis, eastern equine encephalitis, western equine encephalitis]); Viral hemorrhagic fevers (filoviruses [e.g., Ebola, Marburg] and arenaviruses [e.g., Lassa, Machupo]); Smallpox (variola); retroviruses e.g., human immunodeficiency viruses 1 and 2; human papillomavirus [HPV] types 6, 11, 16, 18, 31, 33, and 35.

In various embodiments, the probe can be selective for a polynucleotide sequence that is characteristic of an organisms selected from the group consisting of *Pseudomonas aeruginosa*, *Proteus mirabilis*, *Klebsiella oxytoca*, *Klebsiella pneumoniae*, *Escherichia coli*, *Acinetobacter Baumannii*, *Serratia marcescens*, *Enterobacter aerogenes*, *Enterococcus faecium*, vancomycin-resistant *enterococcus* (VRE), *Staphylococcus aureus*, methicillin-resistant *Staphylococcus aureus* (MRSA), *Streptococcus viridans*, *Listeria monocytogenes*, *Enterococcus* spp., *Streptococcus* Group B, *Streptococcus* Group C, *Streptococcus* Group G, *Streptococcus* Group F, *Enterococcus faecalis*, *Streptococcus pneumoniae*, *Staphylococcus epidermidis*, *Gardnerella vaginalis*, *Micrococcus* sps., *Haemophilus influenzae*, *Neisseria gonorrhoeae*, *Moraxella catarrhalis*, *Salmonella* sps., *Chlamydia trachomatis*, *Peptostreptococcus productus*, *Peptostreptococcus anaerobius*, *Lactobacillus fermentum*, *Eubacterium lentum*, *Candida glabrata*, *Candida albicans*, *Chlamydia* spp., *Campylobacter* spp., *Salmonella* spp., smallpox (variola major), *Yersinia* Pestis, Herpes Simplex Virus I (HSV I), and Herpes Simplex Virus II (HSV II).

In various embodiments, the probe can be selective for a polynucleotide sequence that is characteristic of Group B *Streptococcus*.

In various embodiments, a method of carrying out PCR on a sample can further include one or more of the following steps: heating the biological sample in a microfluidic channel; pressurizing the biological sample in the microfluidic channel at a pressure differential compared to ambient pressure of between about 20 kilopascals and 200 kilopascals, or in some embodiments between about 70 kilopascals and 110 kilopascals.

In some embodiments, the method for sampling a polynucleotide can include the steps of: placing a microfluidic cartridge containing a PCR-ready sample in a receiving bay of a suitably configured apparatus; carrying out PCR on the sample under thermal cycling conditions suitable for creating PCR amplicons from the neutralized polynucleotide in the sample, the PCR-ready sample comprising a polymerase enzyme, a positive control plasmid, a fluorogenic hybridization probe selective for at least a portion of the plasmid, and a plurality of nucleotides; contacting the neutralized polynucleotide sample or a PCR amplicon thereof with the at least one fluorogenic probe that is selective for a polynucleotide sequence, wherein the probe is selective for a polynucleotide sequence that is characteristic of an organism selected from the group consisting of gram positive bacteria, gram negative bacteria, yeast, fungi, protozoa, and viruses; and detecting the fluorogenic probe, the presence of the organism for which the one fluorogenic probe is selective is determined.

Carrying out PCR on a PCR-ready sample can additionally include: independently contacting each of the neutralized polynucleotide sample and a negative control polynucleotide with the PCR reagent mixture under thermal cycling conditions suitable for independently creating PCR amplicons of the neutralized polynucleotide sample and PCR amplicons of the negative control polynucleotide; and/or contacting the neutralized polynucleotide sample or a PCR amplicon thereof and the negative control polynucleotide or a PCR amplicon thereof with at least one probe that is selective for a polynucleotide sequence.

In various embodiments, a method of using the apparatus and detection system described herein can further include one or more of the following steps: determining the presence of a polynucleotide sequence in the biological sample, the polynucleotide sequence corresponding to the probe, if the probe is detected in the neutralized polynucleotide sample or a PCR amplicon thereof; determining that the sample was contaminated if the probe is detected in the negative control polynucleotide or a PCR amplicon thereof; and/or in some embodiments, wherein the PCR reagent mixture further comprises a positive control plasmid and a plasmid probe selective for at least a portion of the plasmid, the method further including determining that a PCR amplification has occurred if the plasmid probe is detected.

Heater Configurations to Ensure Uniform Heating of a Region

In general, the microfluidic channels in which the presence or absence of one or more analytes is determined by the detection system described herein are disposed in thermal contact with a dedicated heater unit. For example, the microfluidic cartridges described herein are typically configured to position in a complementary receiving bay in an apparatus that contains a heater unit. The heater unit is configured to deliver heat to specific microfluidic channels, such as specific regions of the cartridge, including but not limited to one or more microfluidic components, at specific times. For example, the heat source is configured so that particular heating elements are situated adjacent to specific components of a microfluidic network. In certain embodiments, the apparatus uniformly controls the heating of a region of a microfluidic network. In an exemplary embodiment, multiple heaters can be configured to simultaneously and uniformly heat a region, such as the PCR reaction chamber, of a microfluidic network.

Generally, the heating of microfluidic components, such as a PCR reaction chamber, is controlled by passing currents through suitably configured microfabricated heaters. Under control of suitable circuitry, the lanes of a multi-lane cartridge can then be controlled independently of one another. This can lead to a greater energy efficiency of the apparatus, because not all heaters are heating at the same time, and a given heater is receiving current for only that fraction of the time when it is required to heat. Control systems and methods of controllably heating various heating elements are further described in U.S. patent application Ser. No. 11/940,315, filed Nov. 14, 2007 and entitled "Heater Unit for Microfluidic Diagnostic System".

Figure 15:
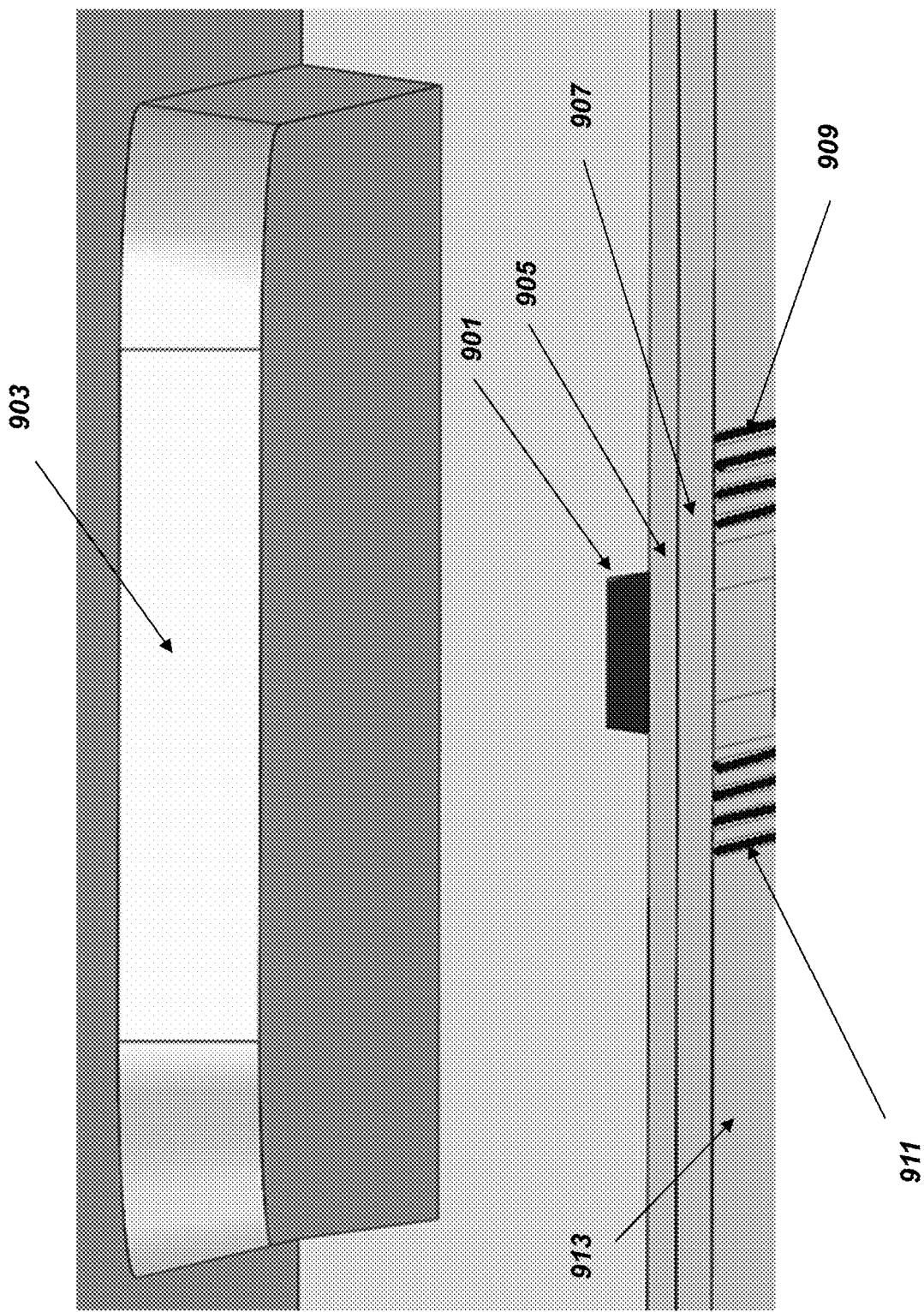
FIG. 15 shows a cross-section of a microfluidic cartridge, when in contact with a heater substrate.

FIG. 15 shows a cross-sectional view of an exemplary microfluidic cartridge to show the location of a PCR channel in relation to the heaters when the cartridge is placed in a suitable apparatus. The view in FIG. 15 is also referred to as a sectional-isometric view of the cartridge lying over a heater wafer. A window 903 above the PCR channel in the cartridge is shown in perspective view. PCR channel 901 (for example, 150µ deep×700µ wide), is shown in an upper layer of the cartridge. A laminate layer 905 of the cartridge (for example, 125µ thick) is directly under the PCR channel 901. A further layer of thermal interface laminate 907 on the cartridge (for example, 125µ thick) lies directly under the laminate layer 905. Heaters 909, 911 are situated in a further substrate layer 913 directly under the thermal interface laminate, shown in cross-section. In one embodiment the heaters are photolithographically defined and etched metal layers of gold (typically about 3,000 Å thick).

Figure 16A:
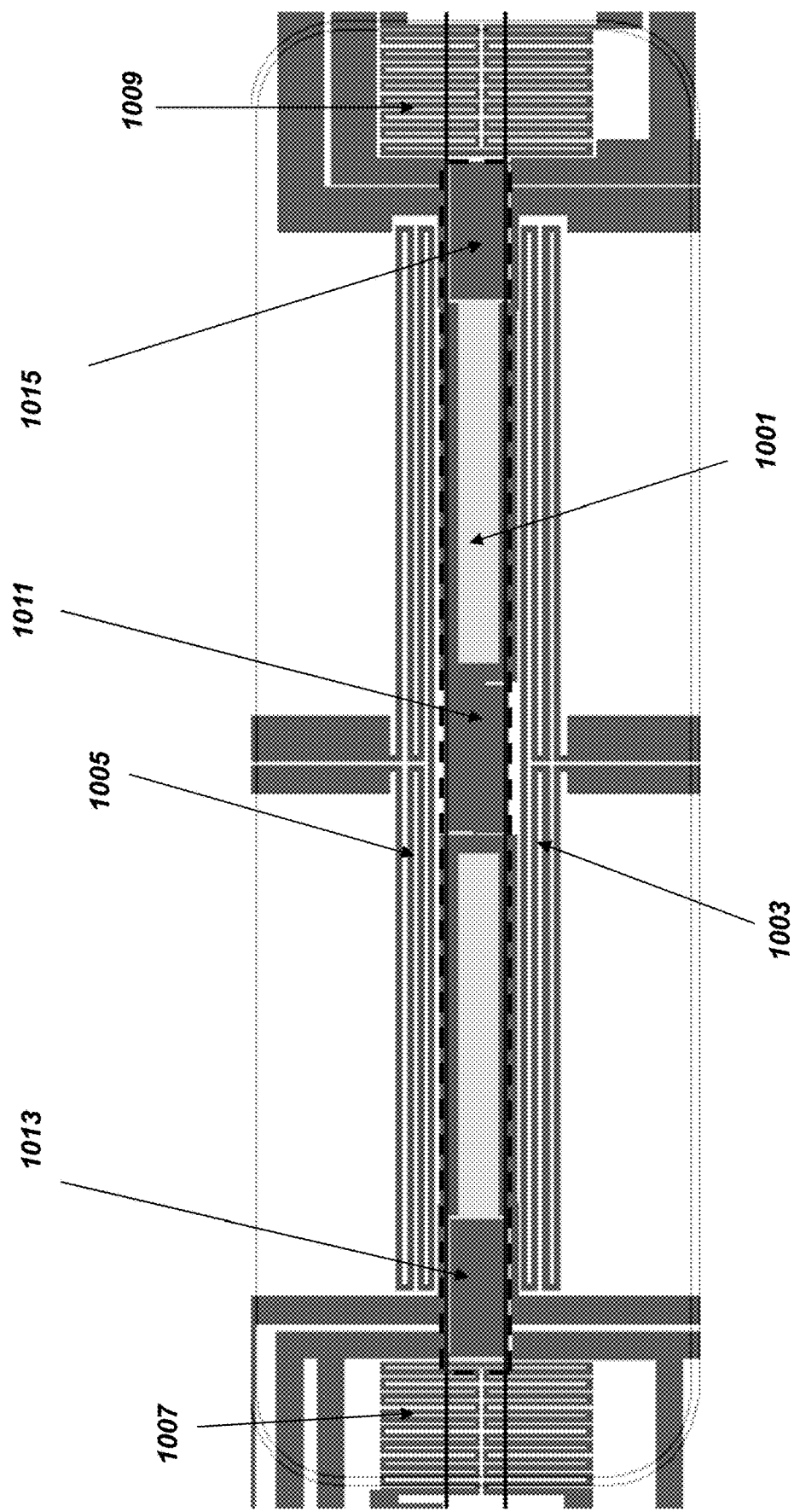
FIGS. 16A and 16B show a plan view of heater circuitry adjacent to a PCR reaction chamber.
Figure 16B:
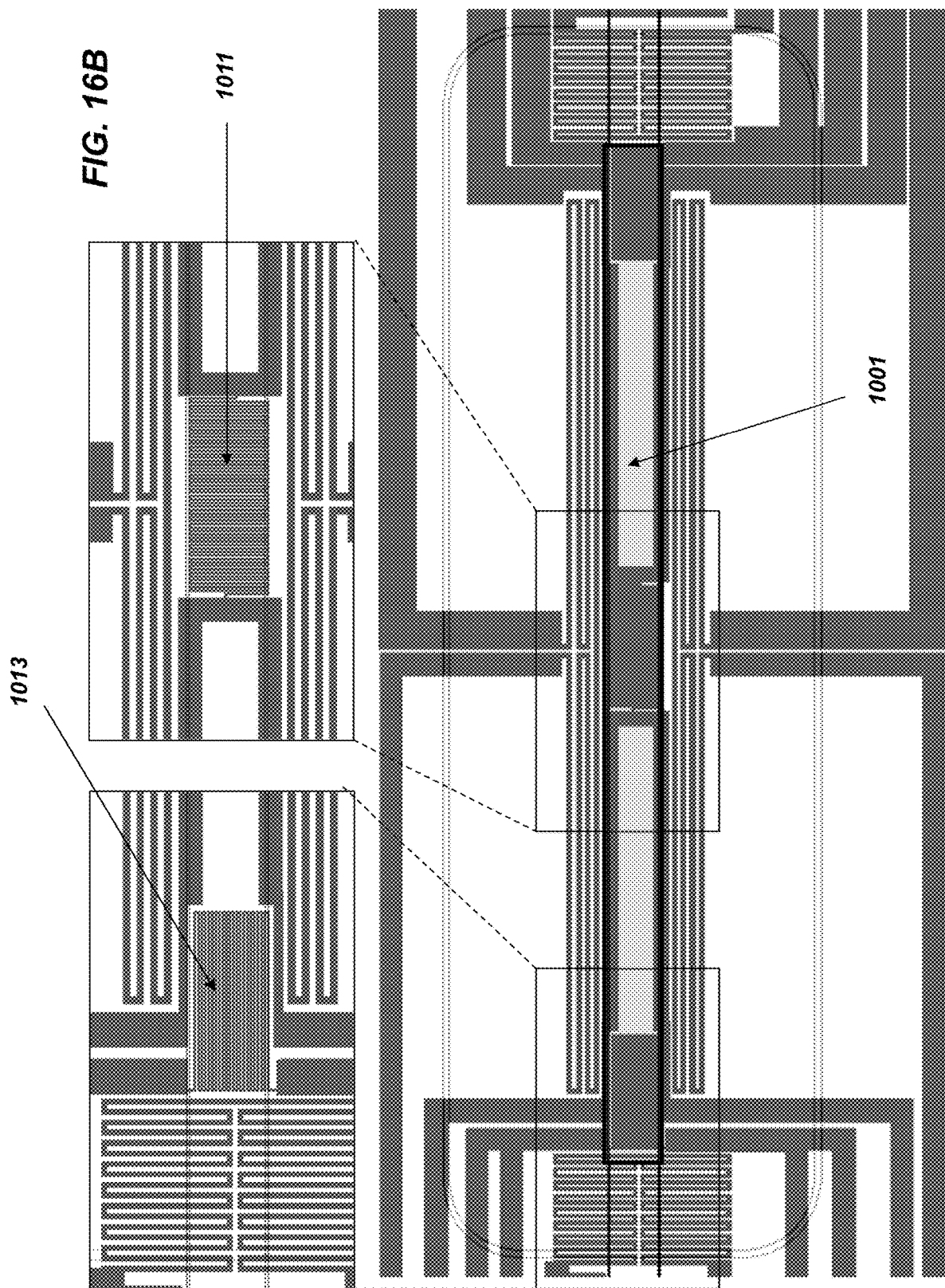

An exemplary such heater array is shown in FIGS. 16A and 16B. Additional embodiments of heater arrays are described in U.S. patent application Ser. No. 11/940,315, entitled "Heater Unit for Microfluidic Diagnostic System" and filed on even date herewith, the specification of which is incorporated herein by reference in its entirety.

Referring to FIGS. 16A and 16B, the PCR reaction chamber 1001, typically having a volume ~1.6 µl, is configured with a long side and a short side, each with an associated heating element. The apparatus therefore includes four heaters disposed along the sides of, and configured to heat, the PCR reaction chamber, as shown in the exemplary embodiment of FIG. 16A: long top heater 1005, long bottom heater 1003, short left heater 1007, and short right heater 1009. The small gap between long top heater 1005 and long bottom heater 1003 results in a negligible temperature gradient (a difference of less than 1° C. across the width of the PCR channel at any point along the length of the PCR reaction chamber) and therefore an effectively uniform temperature throughout the PCR reaction chamber. The heaters on the short edges of the PCR reactor provide heat to counteract the gradient created by the two long heaters from the center of the reactor to the edge of the reactor. It would be understood by one of ordinary skill in the art that still other configurations of one or more heater(s) situated about a PCR reaction chamber are consistent with the methods and apparatus described herein. For example, a 'long' side of the reaction chamber can be configured to be heated by two or more heaters. Specific orientations and configurations of heaters are used to create uniform zones of heating even on substrates having poor thermal conductivity because the poor thermal conductivity of glass, or quartz, or fused silica substrates is utilized to help in the independent operation of various microfluidic components such as valves and independent operation of the various PCR lanes.

Figure 16C:
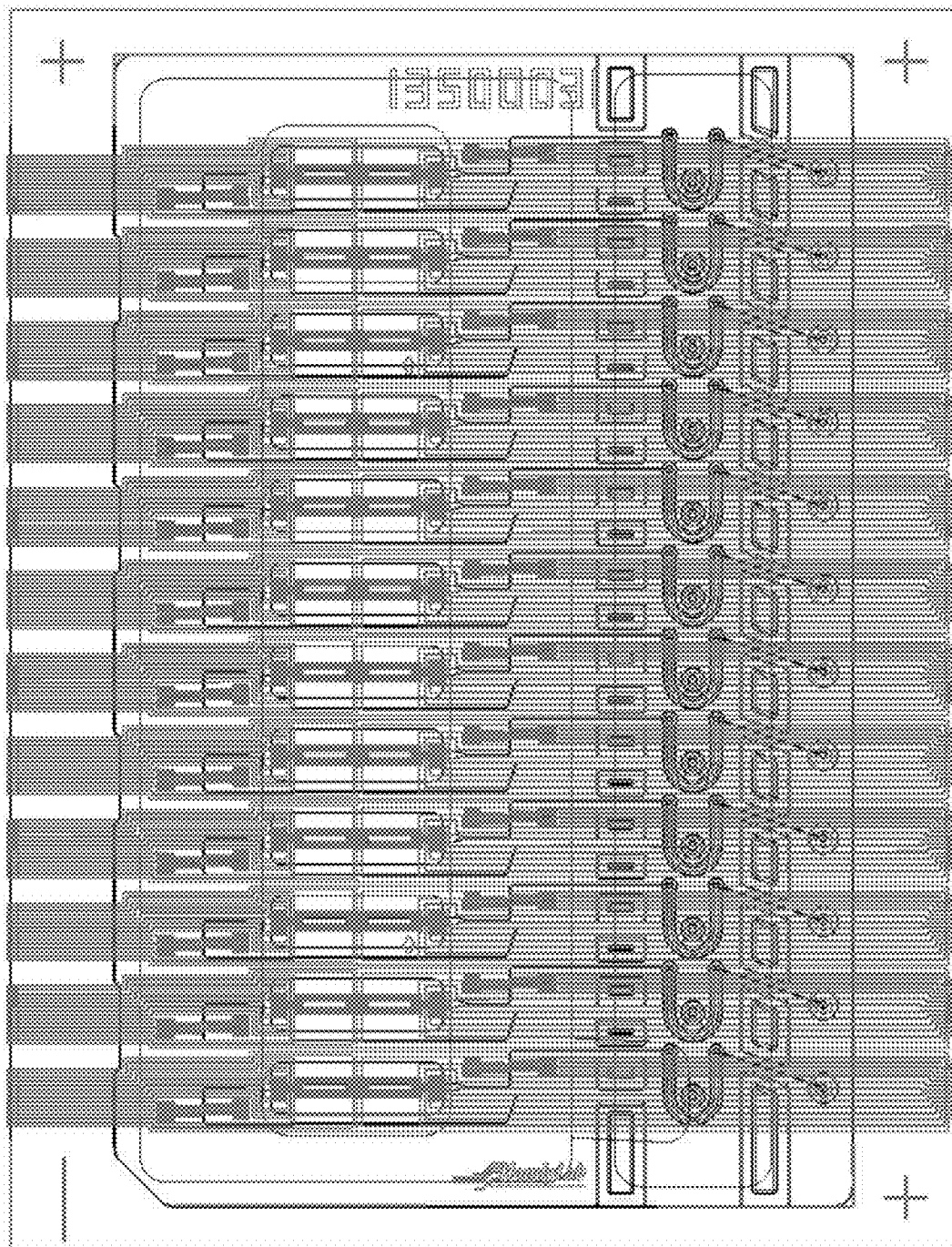
FIG. 16C shows an overlay of an array of heater elements on an exemplary multi-lane microfluidic cartridge, wherein various microfluidic networks are visible.

The configuration for uniform heating, shown in FIG. 16A for a single PCR reaction chamber, can be applied to a multi-lane PCR cartridge in which multiple independent PCR reactions occur. See, e.g., FIG. 16C.

Alignment of microheaters in the heater module with corresponding heat-requiring microcomponents (such as valves, pumps, gates, reaction chambers, etc). The microheaters can be designed to be slightly bigger than the heat requiring microfluidic components so that even though the cartridge may be off-centered from the heater, the individual components can still function effectively.

In other embodiments, as further described in U.S. patent application Ser. No. 11/940,315, filed Nov. 14, 2007 and entitled "Heater Unit for Microfluidic Diagnostic System", the heaters may have an associated temperature sensor, or may themselves function as sensors.

Exemplary Electronics and Software

Figure 17:
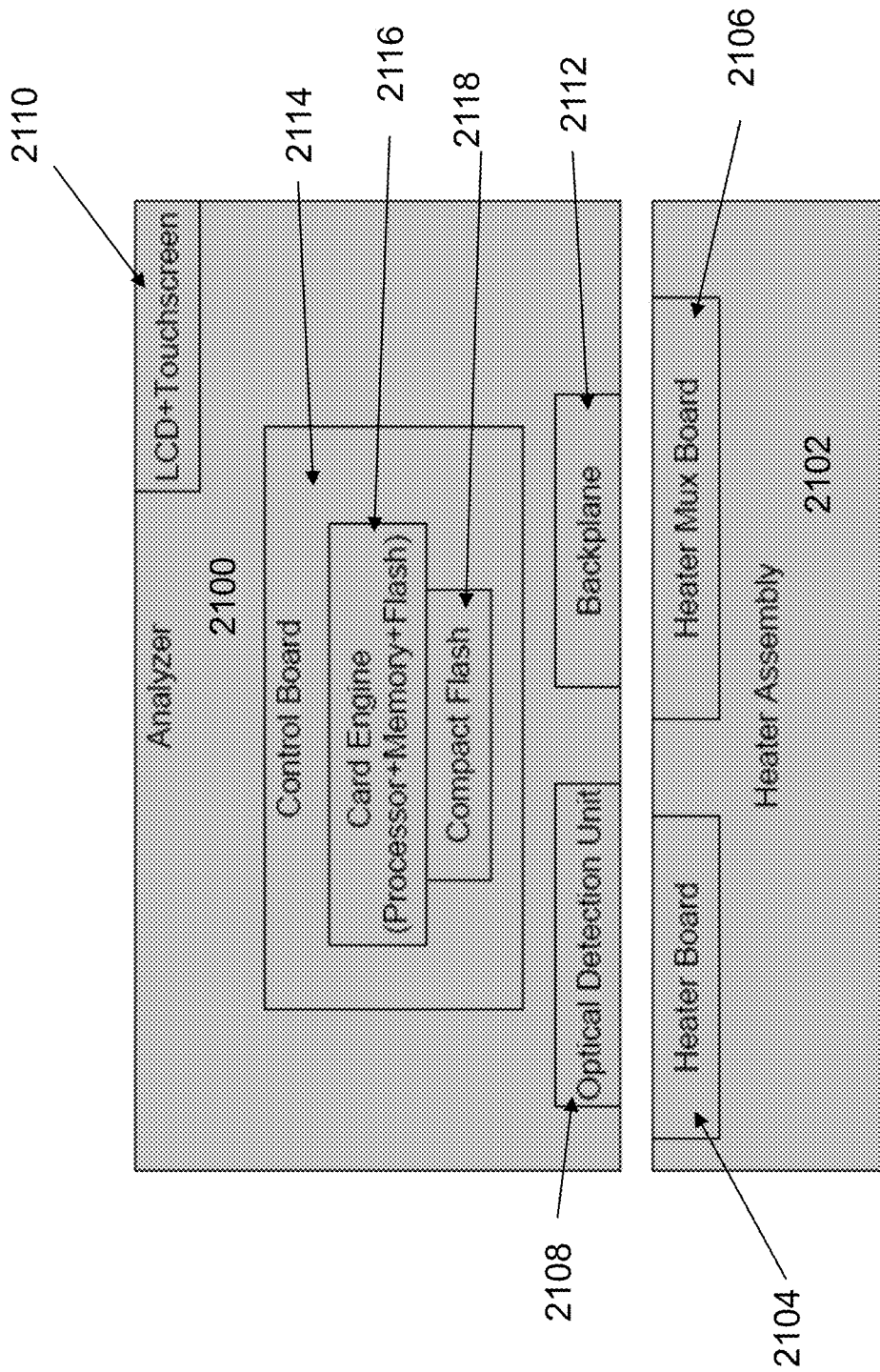
FIG. 17 shows an exemplary layout for electronics and software components, as further described herein.

FIG. 17 describes exemplary electronics architecture modules. It would be understood by one of ordinary skill in the art that other configurations of electronics components are consistent with operation of the apparatus as described herein. In the exemplary embodiment, the electronics architecture is distributed across two components of the apparatus: the Analyzer 2100 and a Heater Assembly 2102. The Analyzer contains an Optical Detection Unit 2108, a Control Board 2114, a Backplane 2112, and a LCD Touchscreen 2110. The Control Board includes a Card Engine 2116 further described herein, and Compact Flash memory 2118, as well as other components. The Heater Assembly includes a Heater Board 2104 and a Heater Mux Board 2106, both further described elsewhere, for example, in U.S. patent application Ser. No. 11/940,315, filed on even date herewith and entitled "Heater Unit for Microfluidic Diagnostic System".

In the exemplary embodiment, the Card Engine electronics module 2116 is a commercial, off the shelf "single board computer" containing a processor, memory, and flash memory for operating system storage.

The LCD+Touchscreen electronics module 2110 is a user interface, for example, driven through a 640 pixel by 480 pixel 8 inch LCD and 5-wire touchscreen.

The Compact Flash electronics module 2118 is a 256 megabyte commercial, off the shelf, compact flash module for application and data storage. Other media are alternatively usable, such as USB-drive, smart media card, memory stick, and smart data-card having the same or other storage capacities.

The Backplane electronics module 2112 is a point of connection for the removable heater assembly 2102. Bare PC boards with two connectors are sufficient to provide the necessary level of connectivity.

The Control Board electronics module 2114 supports peripherals to the Card Engine electronics module 2116. In the exemplary embodiment, the peripherals include such devices as a USB host+slave or hub, a USB CDROM interface, serial ports, and ethernet ports. The Control Board 2114 can include a power monitor with a dedicated processor. The Control Board may also include a real time clock. The Control Board may further include a speaker. The Control Board 2114 also includes a CPLD to provide SPI access to all other modules and programming access to all other modules. The Control Board includes a programmable high voltage power supply. The Control Board includes a Serializer-Deserializer interface to the LCD+Touchscreen electronics module 2110 and to the Optical Detection Unit electronics module 2108. The Control Board also includes module connectors.

In the exemplary embodiment, the optical detection unit electronics module 2108 contains a dedicated processor. The optical detection unit 2108 contains a serializer-deserializer interface. The optical detection unit 2108 contains LED drivers. The optical detection unit also contains high gain-low noise photodiode amplifiers. The optical detection unit preferably has power monitoring capability. The optical detection unit is remotely reprogrammable.

The Heater Board electronics module 2104 is preferably a glass heater board. The Heater Board has PCB with bonding pads for glass heater board and high density connectors.

In the exemplary embodiment, the heater mux ('multiplex') board electronics module 2106 has 24 high-speed ADC, 24 precision current sources, and 96 optically isolated current drivers for heating. The heater mux board has the ability to time-multiplex heating/measurement. The heater mux board has multiplexer banks to multiplex inputs to ADC, and to multiplex current source outputs. The heater mux board has a FPGA with a soft processor core and SDRAM. The heater mux board has a Power Monitor with a dedicated processor. The Heater Mux Board is preferably remotely reprogrammable.

Certain software can be executed in each electronics module. The Control Board Electronics Module executes, for example, Control Board Power Monitor software. The Card Engine electronics module executes an operating system, graphical user interface (GUI) software, an analyzer module, and an application program interface (api). The Optical Detection Unit electronics module executes an optics software module. The Heater Mux Board electronics module executes dedicated Heater Mux software, and Heater Mux Power Monitor software. Each of the separate instances of software can be modular and under a unified control of, for example, driver software.

The exemplary electronics can use Linux, UNIX, Windows, or MacOS, including any version thereof, as the operating system. The operating system is preferably loaded with drivers for USB, Ethernet, LCD, touchscreen, and removable media devices such as compact flash. Miscellaneous programs for configuring the Ethernet interface, managing USB connections, and updating via CD-ROM can also be included.

In the embodiment of FIG. 17, the analyzer module is the driver for specific hardware. The analyzer module provides access to the Heater Mux Module, the Optical Detection Unit, the Control Board Power Monitor, the Real Time Clock, the High Voltage Power Supply, and the LCD backlight. The analyzer module provides firmware programming access to the Control Board power monitor, the Optical Detection Unit, and the Heater Mux Module.

The API provides uniform access to the analyzer module driver. The API is responsible for error trapping, and interrupt handling. The API is typically programmed to be thread safe.

The GUI software can be based on a commercial, off-the-shelf PEG graphics library. The GUI can use the API to coordinate the self-test of optical detection unit and heater assembly. The GUI starts, stops, and monitors test progress. The GUI can also implement an algorithm to arrive at a diagnosis from fluorescence data. Such an algorithm can rely on numerical analysis principles known in the art. The GUI provides access control to the apparatushas and may have an HIS/LIS interface.

The Control Board Power Monitor software monitors power supplies, current and voltage, and signals error in case of a fault.

The Optics Software performs fluorescence detection which is precisely timed to turn on/off of LED with synchronous digitization of the photodetector outputs. The Optics Software can also monitor power supply voltages. The Optics Software can also have self test ability.

The Heater Mux Module software implements a "protocol player" which executes series of defined "steps" where each "step" can turn on sets of heaters to implement a desired microfluidic action. The Heater Mux Module software also has self test ability. The Heater Mux Module software contains a fuzzy logic temperature control algorithm.

The Heater Mux Power Monitor software monitors voltage and current levels. The Heater Mux Power Monitor software can participate in self-test, synchronous, monitoring of the current levels while turning on different heaters.

Overview of an Apparatus for Detecting Fluorescence from an Analyte in a Microfluidic Channel The present technology relates to a cartridge, complementary apparatus, and related methods for amplifying, and carrying out diagnostic analyses on, nucleotides from biological samples. The technology includes a disposable or reusable microfluidic cartridge containing multiple sample lanes capable of processing samples in parallel as further described herein, and a reusable apparatus that is configured to selectively actuate on-cartridge operations, to detect and analyze the products of the PCR amplification in each of the lanes separately, in all simultaneously, or in groups simultaneously, and, optionally, can display the progression of analyses and results thereof on a graphical user interface. Such a reusable apparatus is further described in U.S. patent application Ser. No. 11/985,577, entitled "Microfluidic System for Amplifying And Detecting Polynucleotides In Parallel" and filed on Nov. 14, 2007, and which is incorporated herein by reference in its entirety.

Figure 18:
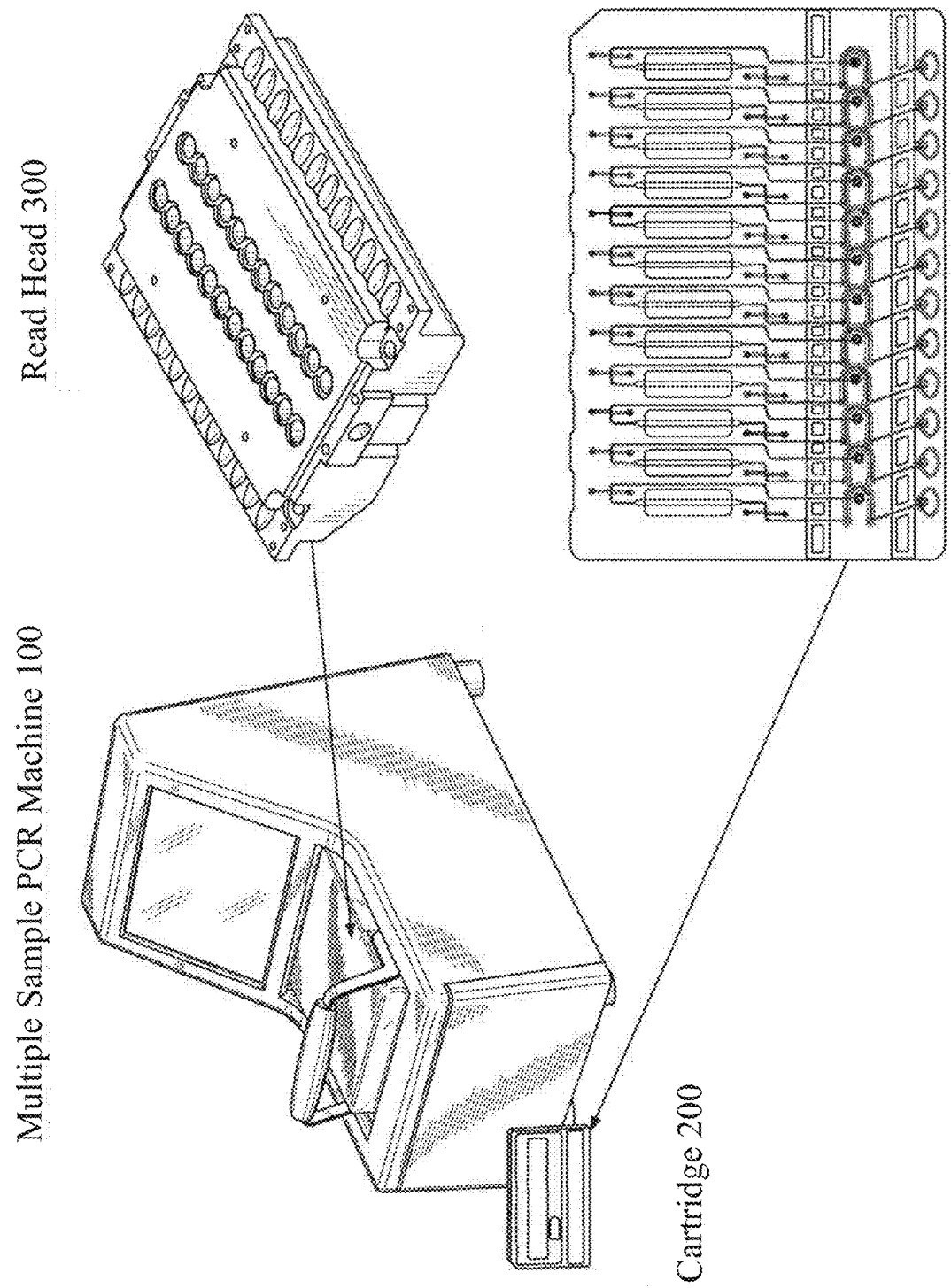
FIG. 18 shows an exemplary apparatus, a microfluidic cartridge, and a read head, as further described herein.

FIG. 18 shows a perspective view of an exemplary apparatus 100 consistent with those described herein, as well as various components thereof, such as exemplary cartridge 200 that contains multiple sample lanes, and exemplary read head 300 that contains detection apparatus for reading signals from cartridge 200. The apparatus 100 of FIG. 18 is able to carry out real-time PCR on a number of samples in cartridge 200 simultaneously or serially. Preferably the number of samples is 12 samples, as illustrated with exemplary cartridge 200, though other numbers of samples such as 4, 8, 10, 16, 20, 24, 25, 30, 32, 36, 40, and 48 are within the scope of the present description. In preferred operation of the apparatus, a PCR-ready solution containing the sample, and, optionally, one or more analyte-specific reagents (ASR's) is prepared, as further described elsewhere (see, e.g., U.S. patent application publication 2006-0166233, incorporated herein by reference), prior to introduction into cartridge 200. An exemplary kit for preparing a PCR-ready sample, the kit comprising buffers, lysis pellets, and affinity pellets, has been described elsewhere (see, e.g., U.S. provisional patent application Ser. No. 60/859,284).

In some embodiments, an apparatus includes: a receiving bay configured to selectively receive a microfluidic cartridge as described herein; at least one heat source thermally coupled to the receiving bay; and a processor coupled to the heat source, wherein the heat source is configured to selectively heat individual regions of individual sample lanes in the cartridge, and the processor is configured to control application of heat to the individual sample lanes, separately, in all simultaneously, or in groups simultaneously; at least one detector configured to detect one or more polynucleotides or a probe thereof in a sample in one or more of the individual sample lanes, separately or simultaneously; and a processor coupled to the detector to control the detector and to receive signals from the detector.

The receiving bay is a portion of the apparatus that is configured to selectively receive the microfluidic cartridge. For example, the receiving bay and the microfluidic cartridge can be complementary in shape so that the microfluidic cartridge is selectively received in, e.g., a single orientation. The microfluidic cartridge can have a registration member that fits into a complementary feature of the receiving bay. The registration member can be, for example, a cut-out on an edge of the cartridge, such as a corner that is cut-off, or one or more notches that are made on one or more of the sides in a distinctive pattern that prevents a cartridge from being loaded into the bay in more than one distinct orientation. By selectively receiving the cartridge, the receiving bay can help a user to place the cartridge so that the apparatus can properly operate on the cartridge. The cartridge can be designed to be slightly smaller than the dimensions of the receiving bay by approximately 200-300 microns for easy placement and removal of the cartridge.

The receiving bay can also be configured so that various components of the apparatus that operate on the microfluidic cartridge (heat sources, detectors, force members, and the like) are positioned to properly operate thereon. For example, a contact heat source can be positioned in the receiving bay such that it can be thermally coupled to one or more distinct locations on a microfluidic cartridge that is selectively received in the bay. Alignment of microheaters in the heater module with corresponding heat-requiring microcomponents (such as valves, pumps, gates, reaction chambers, etc). The microheaters can be designed to be slightly bigger than the heat requiring microfluidic components so that even though the cartridge may be off-centered from the heater, the individual components can still function effectively.

The lower surface of the cartridge can have a layer of mechanically compliant heat transfer laminate that can enable thermal contact between the microfluidic substrate and the microheater substrate of the heater module. A minimal pressure of 1 psi can be employed for reliable operation of the thermal valves, gates and pumps present in the microfluidic cartridge.

In various embodiments of the apparatus, the apparatus can further include a sensor coupled to the processor, the sensor configured to sense whether the microfluidic cartridge is selectively received.

The detector can be, for example, an optical detector as further described elsewhere herein. For example, the detector can include a light source that selectively emits light in an absorption band of a fluorescent dye, and a light detector that selectively detects light in an emission band of the fluorescent dye, wherein the fluorescent dye corresponds to a fluorescent polynucleotide probe or a fragment thereof. Alternatively, for example, the optical detector can include a bandpass-filtered diode that selectively emits light in the absorption band of the fluorescent dye and a bandpass filtered photodiode that selectively detects light in the emission band of the fluorescent dye; or for example, the optical detector can be configured to independently detect a plurality of fluorescent dyes having different fluorescent emission spectra, wherein each fluorescent dye corresponds to a fluorescent polynucleotide probe or a fragment thereof; or for example, the optical detector can be configured to independently detect a plurality of fluorescent dyes at a plurality of different locations on a microfluidic cartridge, wherein each fluorescent dye corresponds to a fluorescent polynucleotide probe or a fragment thereof in a different sample. The detector can also be configured to detect the presence or absence of sample in a PCR reaction chamber in a given sample lane, and to condition initiation of thermocycling upon affirmative detection of presence of the sample.

In various embodiments, the apparatus can further include an analysis port. The analysis port can be configured to allow an external sample analyzer to analyze a sample in the microfluidic cartridge. For example, the analysis port can be a hole or window in the apparatus which can accept an optical detection probe that can analyze a sample or progress of PCR in situ in the microfluidic cartridge. In some embodiments, the analysis port can be configured to direct a sample from the microfluidic cartridge to an external sample analyzer; for example, the analysis port can include a conduit in fluid communication with the microfluidic cartridge that directs a liquid sample containing an amplified polynucleotide to a chromatography apparatus, an optical spectrometer, a mass spectrometer, or the like.

The heat source can be, for example, a heat source such as a resistive heater or network of resistive heaters, and the like.

In preferred embodiments, the at least one heat source can be a contact heat source selected from a resistive heater (or network thereof), a radiator, a fluidic heat exchanger and a Peltier device. The contact heat source can be configured at the receiving bay to be thermally coupled to one or more distinct locations of a microfluidic cartridge received in the receiving bay, whereby the distinct locations are selectively heated. The contact heat source typically includes a plurality of contact heat sources, each configured at the receiving bay to be independently thermally coupled to a different distinct location in a microfluidic cartridge received therein, whereby the distinct locations are independently heated. The contact heat sources can be configured to be in direct physical contact with one or more distinct locations of a microfluidic cartridge received in the bay. In various embodiments, each contact source heater can be configured to heat a distinct location having an average diameter in 2 dimensions from about 1 millimeter (mm) to about 15 mm (typically about 1 mm to about 10 mm), or a distinct location having a surface area of between about 1 $mm^2$ about 225 $mm^2$ (typically between about 1 $mm^2$ and about 100 $mm^2$, or in some embodiments between about 5 $mm^2$ and about 50 $mm^2$). Various configurations of heat sources are further described in U.S. patent application Ser. No. 11/940,315, entitled "Heater Unit for Microfluidic Diagnostic System" and filed on even date herewith.

In various embodiments, the heat source is disposed in a heating module that is configured to be removable from the apparatus.

In various embodiments, the apparatus can include a compliant layer at the contact heat source configured to thermally couple the contact heat source with at least a portion of a microfluidic cartridge received in the receiving bay. The compliant layer can have a thickness of between about 0.05 and about 2 millimeters and a Shore hardness of between about 25 and about 100.

In various embodiments, the apparatus can further include one or more force members configured to apply force to at least a portion of a microfluidic cartridge received in the receiving bay. The one or more force members are configured to apply force to thermally couple the at least one heat source to at least a portion of the microfluidic cartridge. The application of force is important to ensure consistent thermal contact between the heater wafer and the PCR reactor and microvalves in the microfluidic cartridge.

In various embodiments, the apparatus can further include a lid at the receiving bay, the lid being operable to at least partially exclude ambient light from the receiving bay.

The apparatus preferably also includes a processor comprising microprocessor circuitry, in communication with, for example, the input device and a display, that accepts a user's instructions and controls analysis of samples.

In various embodiments, the apparatus can further include at least one input device coupled to the processor, the input device being selected from the group consisting of a keyboard, a touch-sensitive surface, a microphone, and a mouse.

In various embodiments, the apparatus can further include at least one sample identifier coupled to the processor, the sample identifier being selected from an optical scanner such as an optical character reader, a bar code reader, or a radio frequency tag reader. For example, the sample identifier can be a handheld bar code reader.

In various embodiments, the apparatus can further include at least one data storage medium coupled to the processor, the medium selected from: a hard disk drive, an optical disk drive, or one or more removable storage media such as a CD-R, CD-RW, USB-drive, or flash memory card.

In various embodiments, the apparatus can further include at least one output coupled to the processor, the output being selected from a display, a printer, and a speaker, the coupling being either directly through a directly dedicated printer cable, or wirelessly, or via a network connection.

The apparatus further optionally comprises a display that communicates information to a user of the system. Such information includes but is not limited to: the current status of the system; progress of PCR thermocycling; and a warning message in case of malfunction of either system or cartridge. The display is preferably used in conjunction with an external input device as elsewhere described herein, through which a user may communicate instructions to apparatus 100. A suitable input device may further comprise a reader of formatted electronic media, such as, but not limited to, a flash memory card, memory stick, USB-stick, CD, or floppy diskette. An input device may further comprise a security feature such as a fingerprint reader, retinal scanner, magnetic strip reader, or barcode reader, for ensuring that a user of the system is in fact authorized to do so, according to pre-loaded identifying characteristics of authorized users. An input device may additionally—and simultaneously—function as an output device for writing data in connection with sample analysis. For example, if an input device is a reader of formatted electronic media, it may also be a writer of such media. Data that may be written to such media by such a device includes, but is not limited to, environmental information, such as temperature or humidity, pertaining to an analysis, as well as a diagnostic result, and identifying data for the sample in question.

The apparatus may further include a computer network connection that permits extraction of data to a remote location, such as a personal computer, personal digital assistant, or network storage device such as computer server or disk farm. The network connection can be a communications interface selected from the group consisting of: a serial connection, a parallel connection, a wireless network connection, and a wired network connection such as an ethernet or cable connection, wherein the communications interface is in communication with at least the processor. The computer network connection may utilize, e.g., ethernet, firewire, or USB connectivity. The apparatus may further be configured to permit a user to e-mail results of an analysis directly to some other party, such as a healthcare provider, or a diagnostic facility, or a patient.

In various embodiments, there is an associated computer program product includes computer readable instructions thereon for operating the apparatus and for accepting instructions from a user.

Apparatus 100 may optionally comprise one or more stabilizing feet that cause the body of the device to be elevated above a surface on which system 100 is disposed, thereby permitting ventilation underneath system 100, and also providing a user with an improved ability to lift system 100.

In another preferred embodiment (not shown in the FIGs. herein), a cartridge and apparatus are configured so that the read-head does not cover the sample inlets, thereby permitting loading of separate samples while other samples are undergoing PCR thermocycling.

EXAMPLES

Example 1: Analyzer and Control Circuitry

An Analyzer unit can contain typical hardware/firmware that can be employed to drive and monitor the operations on the cartridges as well as software to interpret, communicate and store the results. The unit currently weighs about 20 lbs. and is approximately 10" wide by 16" deep by 13" high. Typical components of the Analyzer can include: (a) Control Electronics (DAQ), (b) Heater/Sensor Module, (c) Fluorescent Detection Module, (d) Mechanical Fixtures, (e) Software and (f) User Interface (LCD/Touch screen) (g) Peripherals (CD-ROM, USB/Serial/Ethernet communication ports, barcode scanner, optional keyboard). An exemplary embodiment is shown in FIG. 18.

Control electronics can be spread over four different circuit board assemblies. These include the Main, MUX, LCD, and Detector boards.

MAIN board: Can serve as the hub of the Analyzer control electronics and manages communication and control of the other various electronic sub-assemblies. The main board can also serve as the electrical and communications interface with the external world. An external power supply (12V DC/10 A; UL certified) can be used to power the system. The unit can communicate via 5 USB ports, a serial port and an Ethernet port. Finally, the main board can incorporate several diagnostic/safety features to ensure safe and robust operation of the Analyzer.

MUX Board: Upon instruction from the main board, the MUX board can perform all the functions typically used for accurate temperature control of the heaters and can coordinate the collection of fluorescence data from the detector board.

LCD Board: Can contain the typical control elements to light up the LCD panel and interpret the signals from the touch sensitive screen. The LCD/touch screen combination can serve as a mode of interaction with the user via a Graphical User Interface.

Detector Board: Can house typical control and processing circuitry that can be employed to collect, digitize, filter, and transmit the data from the fluorescence detection modules.

Example 2: Detector Integrated in Force Member

This non-limiting example describes pictorially, various embodiments of a detection system integrated into a force member, in an apparatus for carrying out diagnostics on microfluidic samples. An exploded view is shown in FIG. 19.

Figure 20A:
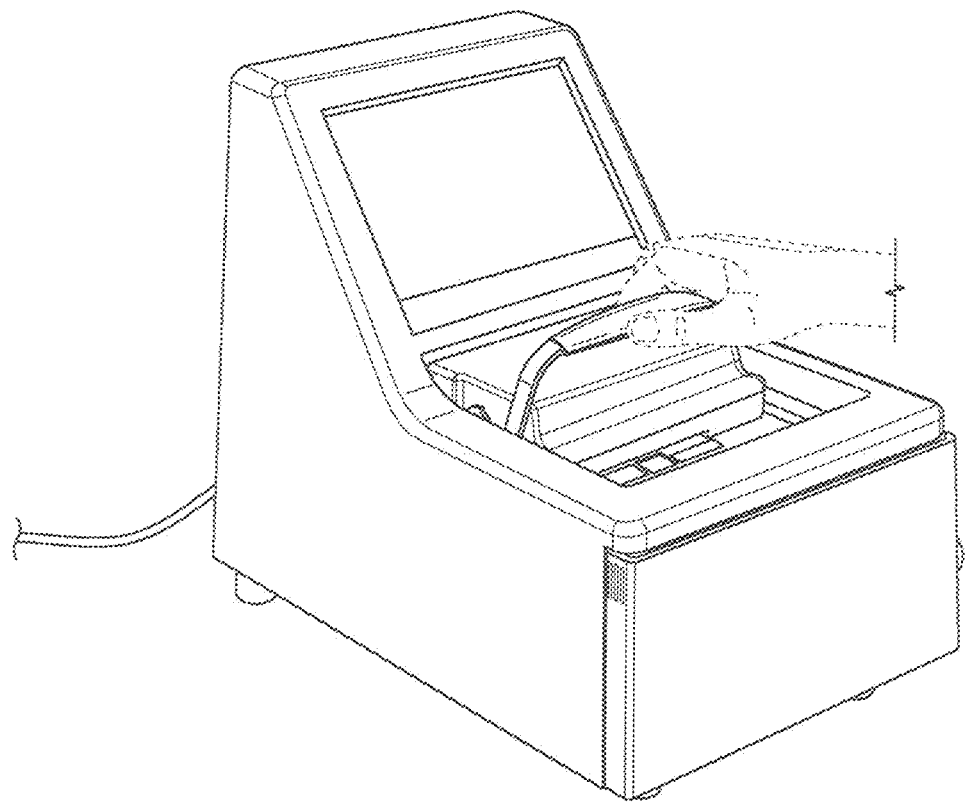
FIGS. 20A and 20B show an exemplary apparatus having a detector mounted in a sliding lid.

FIG. 20A: The lid of the apparatus can be closed, which can block ambient light from the sample bay, and place an optical detector contained in the lid into position with respect to the microfluidic cartridge.

Figure 20B:
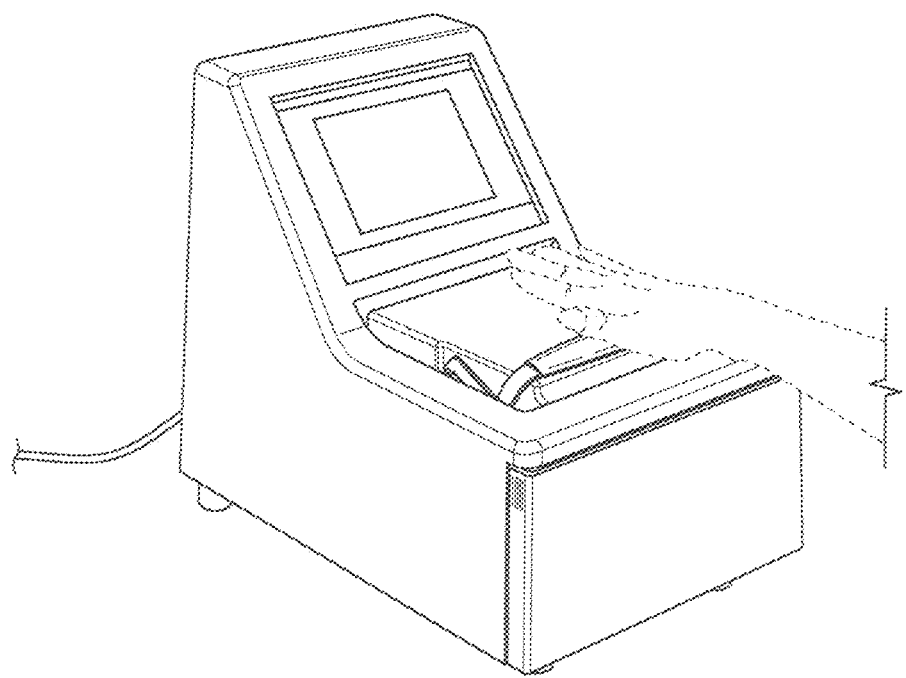

FIG. 20B: The lid of the apparatus can be closed to apply pressure to the cartridge. Application of minimal pressure on the cartridge: after the slider compresses the cartridge, the slider can compress the compliant label of the cartridge. This can cause the bottom of the cartridge to be pressed down against the surface of the heater unit present in the heater module. Springs present in the slider can deliver, for example approximately 50 lb of pressure to generate a minimum pressure, for example 2 psi over the entire cartridge bottom.

Thermal interface: the cartridge bottom can have a layer of mechanically compliant heat transfer laminate that can enable thermal contact between the microfluidic substrate and the microheater substrate of the heater module. A minimal pressure of 1 psi can be employed for reliable operation of the thermal valves, gate and pumps present in the microfluidic cartridge.

Mechanicals and assembly: the Analyzer can have a simple mechanical frame to hold the various modules in alignment. The optics module can be placed in rails for easy opening and placement of cartridges in the Analyzer and error-free alignment of the optics upon closing. The heater/sensor module can be also placed on rails or similar guiding members for easy removal and insertion of the assembly.

Figure 21B:
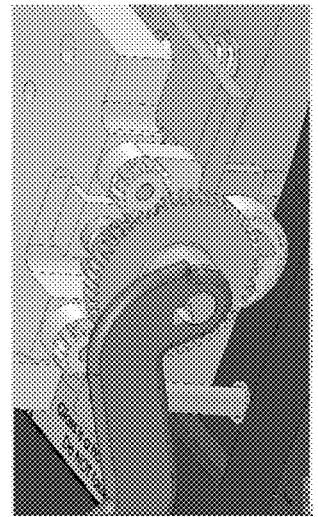
FIGS. 21A-21C show a force member.
Figure 21A:
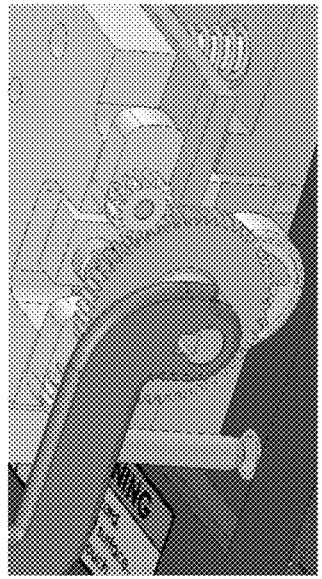
Figure 21C:
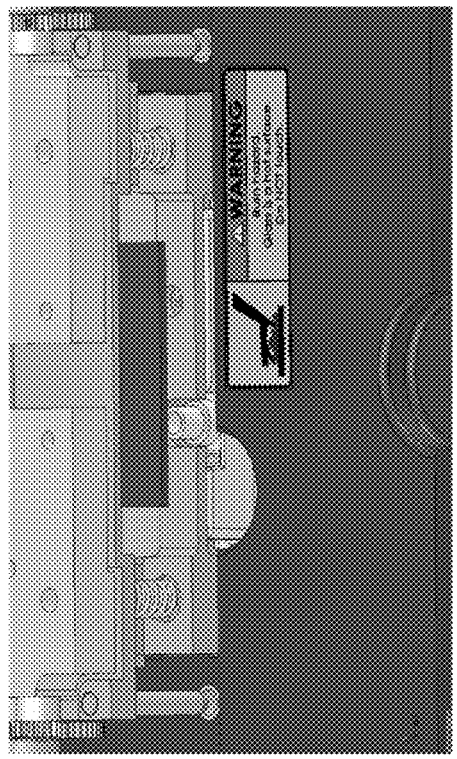

Slider: the slider of the Analyzer can house the optical detection system as well as the mechanical assembly that can enables the optics jig to press down on the cartridge when the handle of the slider is turned down onto the analyzer. The optics jig can be suspended from the case of the slider at 4 points. Upon closing the slider and turning the handle of the analyzer down, 4 cams can turn to push down a plate that presses on 4 springs. On compression, the springs can deliver approximately 50 lb on the optical block. See FIGS. 21A-21C.

The bottom surface of the optics block can be made flat to within 100 microns, typically within 25 microns, and this flat surface can press upon the compliant (shore hardness approximately 50-70) label (approximately 1.5 mm thick under no compression) of the cartridge making the pressure more or less uniform over the cartridge. An optional lock-in mechanism can also be incorporated to prevent the slider from being accidentally knocked-off while in use.

Figure 22A:
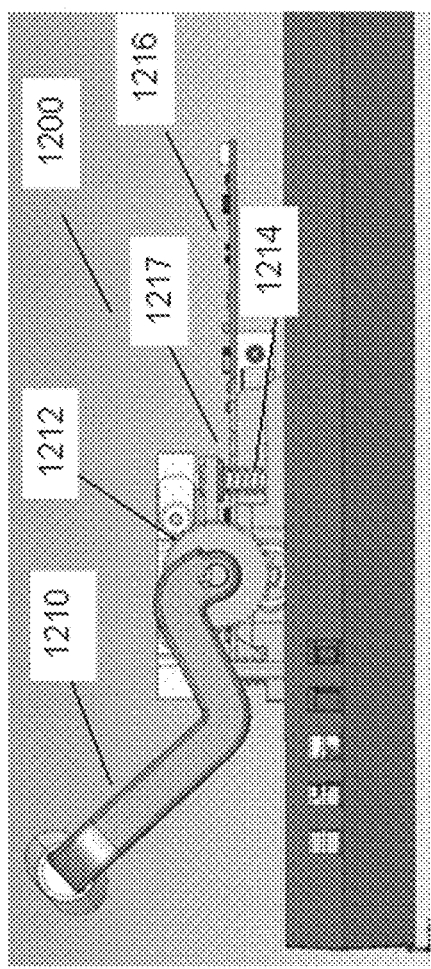
FIGS. 22A-22D show a force member associated with a detector.

FIG. 22A shows a side view of a lever assembly 1200, with lever 1210, gear unit 1212, and force member 1214. Assembly 1200 can be used to close the lid of the apparatus and (through force members 1214) apply force to a microfluidic cartridge 1216 in the sample well 1217. One force member is visible in this cut away view, but any number, for example 4, can be used. The force members can be, for example, a manual spring loaded actuator as shown, an automatic mechanical actuator, a material with sufficient mechanical compliance and stiffness (e.g., a hard elastomeric plug), and the like. The force applied to the microfluidic cartridge 1216 can result in a pressure at the surface of the microfluidic cartridge 1216 of at least about 0.7 psi to about 7 psi (between about 5 and about 50 kilopascals), or in some embodiments about 2 psi (about 14 kilopascals.

Figure 22B:
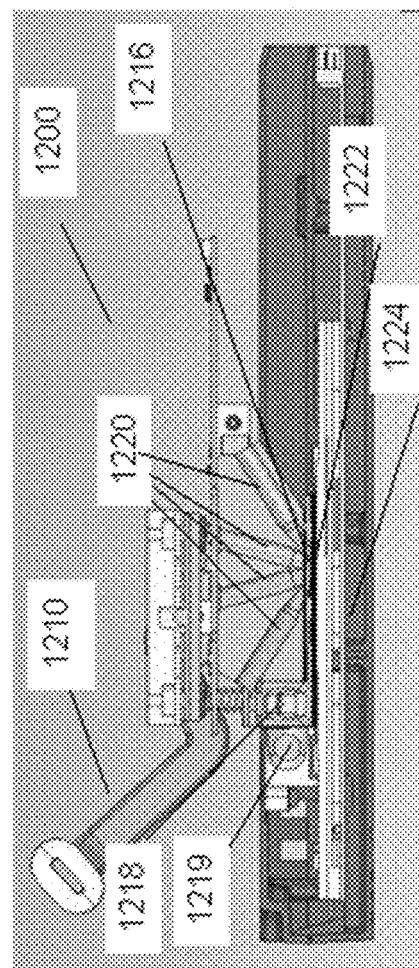

FIG. 22B shows a side view of lever assembly 1200, with microfluidic cartridge 1216 in the sample well 1217. A heat source 1219 (for example, a xenon bulb as shown) can function as a radiant heat source directed at a sample inlet reservoir 1218, where the heat can lyse cells in reservoir 1218. A thermally conductive, mechanically compliant layer 1222 can lie at an interface between microfluidic cartridge 1216 and thermal stage 1224. Typically, microfluidic cartridge 1216 and thermal stage 1224 can be planar at their respective interface surfaces, e.g., planar within about 100 microns, or more typically within about 25 microns. Layer 1222 can improve thermal coupling between microfluidic cartridge 1216 and thermal stage 1224. Optical detector elements 1220 can be directed at the top surface of microfluidic cartridge 1216.

Figure 22C:
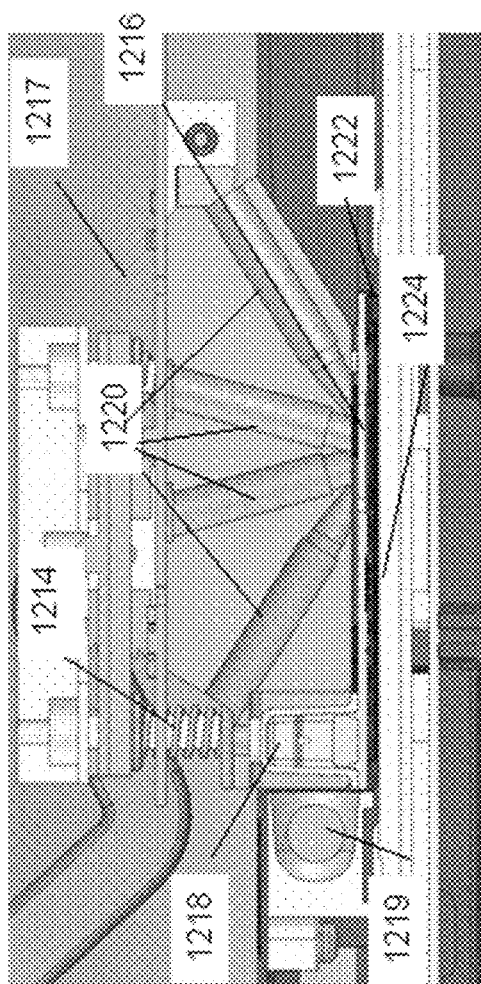
Figure 22D:
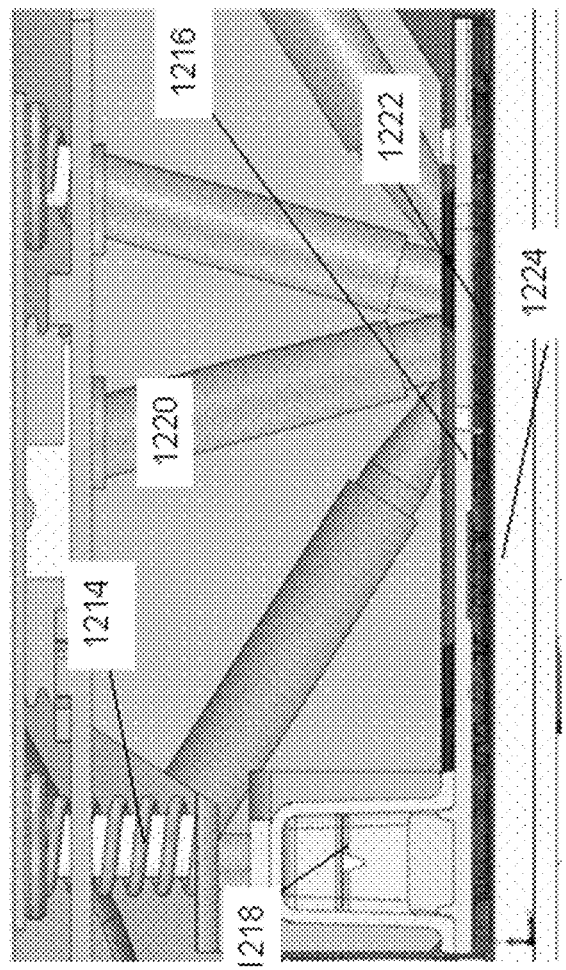

FIGS. 22C and 22D show further cross-sectional views.

Example 3: Exemplary Optics Assembly

In an exemplary embodiment, an assembly comprising a detector on an optical chassis and a force member that can exert pressure is housed in a plastic enclosure (slider) that can be positioned to cover a multi-lane microfluidic cartridge. The slider has a handle that can be easily grasped (between 4" and 5" width) by a user and drawn towards the front of the instrument using less than 11 pounds of force. The slider is guided for smooth and easy pushing and pulling with a handle, which also serves as a pressure-locking device. The slider's horizontal position is sensed in both the all-open (fully away from the user) and in the all-forward position, and reported to controlling software. Once properly located over a microfluidic cartridge, the slider will be locked in a "down" pressured position, and the user will be required to apply no more than seven pounds of upward force normal to the handle to release the pressure. Accidental unlocking of the slider mechanism is thereby prevented. The slider and optical chassis pressure assembly registers with a heater cassette module positioned underneath a microfluidic cartridge to within 0.010". A close fit is important for proper heater/cartridge interface connections.

The slider aligns with the control chip on the heater unit when it is in the full back position. The height is the same as the distance between the read head bottom and the read area on the cartridge. The slider does not come in contact with the control chip but it is positioned such that the center of the control chip is in the focal plane of the optic system (±0.005"). The slider assembly does not degrade in performance over a life of 10,000 cycles, where a cycle is defined as: beginning with the slider in the back position, and sliding forward then locking the handle down on a cartridge, unlocking the handle and returning it to the original back position. All optical path parts should be non-reflective (anodized, painted, molded, etc.) and do not lose this feature for 10,000 cycles. The optics unit is unaffected by a light intensity of <=9,000 foot-candles from a source placed 12" from the instrument at angles where light penetration is most likely to occur. No degradation of performance is measured at the photo-detector after 10,000 cycles.

A single channel is made that houses two LED sources (blue and amber) and two additional channels that will house one photodiode detector each (four total bored holes). The two paired channels (source and detector) are oriented 43° from each other, measured from the optical axis and are in-line with the other paired channels that are at the same 43° orientation. The holes bored in the optical chassis contain filters and lenses with appropriate spacers, the specifications of which are further described herein. The LEDs are held in place to prevent movement as the mechanical alignment is important for good source illumination. The LED's are preferably twisted until the two "hot spots" are aligned with the reading channels on the cartridge. This position must be maintained until the LED's cannot be moved.

The optical chassis is made of aluminum and is black anodized. The bottom pressure surface of the optical chassis is flat to ±0.001" across the entire surface. The optical chassis is center-balanced such that the center of the optical chassis force is close to the center of the reagent cartridge. The pressure assembly (bottom of the optical chassis) provides uniform pressure of a minimum of 1 psi across all heater sections of the reagent cartridge. The optical assembly can be moved away from the reagent cartridge area for cartridge removal and placement. Appropriate grounding of the optical chassis is preferred to prevent spurious signals to emanate to the optic PCB.

The LED light sources (amber and blue) are incident on a microfluidic cartridge through a band pass filter and a focusing lens. These LED light sources have a minimum output of 2800 millicandles (blue) and 5600 millicandles (Green), and the center wavelengths are 470 (blue) and 575 (amber) nanometers, with a half band width of no more than 75 nanometers.

The LED light excites at least one fluorescent molecule (initially attached to an oligonucleotide probe) in a single chamber on a cartridge, causing it to fluoresce. This fluorescence will normally be efficiently blocked by a closely spaced quencher molecule. DNA amplification via TAQ enzyme will separate the fluorescent and quenching molecules from the oligonucleotide probe, disabling the quenching. DNA amplification will only occur if the probe's target molecule (a DNA sequence) is present in the sample chamber. Fluorescence occurs when a certain wavelength strikes the target molecule. The emitted light is not the same as the incident light. Blue incident light is blocked from the detector by the green only emission filter. Green incident light similarly is blocked from the detector by the yellow emission filter. The fluorescent light is captured and travels via a pathway into a focusing lens, through a filter and onto a very sensitive photodiode. The amount of light detected increases as the amount of the DNA amplification increases. The signal will vary with fluorescent dye used, but background noise should be less than 1 mV peak-to-peak. The photo-detector, which can be permanently mounted to the optical chassis in a fixed position, should be stable for 5 years or 10,000 cycles, and should be sensitive to extremely low light levels, and have a dark value of no more than 60 mV. Additionally, the photo-detector must be commercially available for at least 10 years. The lenses are Plano-convex (6 mm detector, and 12 mm source focal length) with the flat side toward the test cartridge on both lenses. The filters should remain stable over normal operating humidity and temperature ranges.

The filters, e.g., supplied by Omega Optical (Brattleboro, Vt. 05301), are a substrate of optical glass with a surface quality of F/F per Mil-C-48497 A. The individual filters have a diameter of 6.0±0.1 mm, a thickness of 6.0±0.1 mm, and the AOI and ½ cone AOI is 0 degrees and ±8 degrees, respectively. The clear aperture is >/=4 mm diameter and the edge treatment is blackened prior to mounting in a black, anodized metal ring.

The FITC exciter filter is supplied by, e.g., Omega Optical (PN 481AF30-RED-EXC). They have a cut-off frequency of 466±4 nm and a cut-on frequency of 496±4 nm. Transmission is >/=65% peak and blocking is: >/=OD8 in theory from 503 to 580 nm, >/=OD5 from 501-650 nm, >/=OD4 avg. over 651-1000 nm, and >/=OD4 UV-439 nm.

The FITC emitter filter is supplied by, e.g., Omega Optical (PN 534AF40-RED-EM). They have a cut-off frequency of 514±2 nm and a cut-on frequency of 554±4 nm. Transmission is >/=70% peak and blocking is: >/=OD8 in theory from 400 to 504 nm, >/=OD5 UV-507 nm, and >/=OD4 avg. 593-765 nm.

The amber exciter filters are supplied by, e.g., Omega Optical (PN 582AF25-RED-EXC). They have a cut-off frequency of 594±5 nm and a cut-on frequency of 569±5 nm. Transmission is >/=70% peak and blocking is: >/=OD8 in theory from 600 to 700 nm, >/=OD5 600-900 nm, and >/=OD4 UV-548 nm.

The amber emitter filters are supplied by, e.g., Omega Optical (PN 627AF30-RED-EM). They have a cut-off frequency of 642±5 nm and a cut-on frequency of 612±5 nm. Transmission is >/=70% peak and blocking is: >/=OD8 in theory from 550 to 600 nm, >/=OD5 UV-605 nm, and >/=OD5 avg. 667-900 nm.

The spacers should be inert and temperature stable throughout the entire operating range and should maintain the filters in strict position and alignment. The epoxy used should have optically black and opaque material and dry solid with no tacky residue. Additionally, it should have temperature and moisture stability, exert no pressure on the held components, and should mount the PCB in such a way that it is fixed and stable with no chances of rotation or vertical height changes. 50% of illumination shall fall on the sample plane within an area 0.1" (2.5 mm) wide by 0.3" (7.5 mm) along axis of the detection channel. Fluorescence of the control chip should not change more than 0.5% of the measured signal per 0.001" of height though a region ±0.010 from the nominal height of the control chip.

Example 4: Exemplary Optics Board

Figure 23:
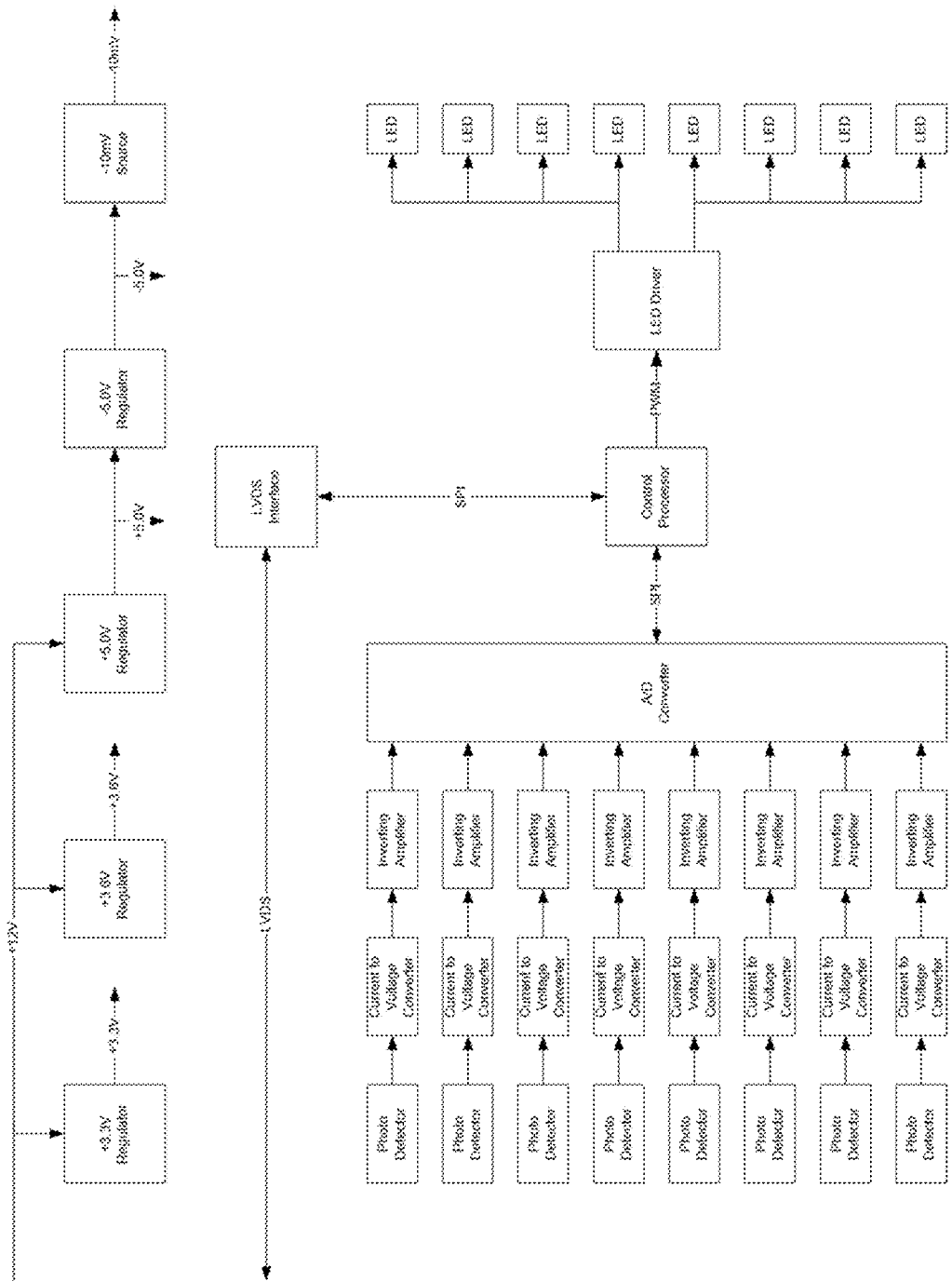
FIG. 23 shows a block diagram of exemplary electronic circuitry in conjunction with a detector as described herein.

An exemplary optics board is shown schematically in FIG. 23, and is used to collect and amplify the fluorescent signature of a successful chemical reaction on a microfluidic cartridge, and control the intensity of LED's using pulse-width modulation (PWM) to illuminate the cartridge sample over up to four channels, each with two color options. Additionally, it receives instructions and sends results data back over an LVDS (low-voltage differential signaling) SPI (serial peripheral interface). In some embodiments there is a separate instance of this circuitry for each PCR channel that is monitored.

The power board systems include: a +12V input; and +3.3V, +3.6V, +5V, and −5V outputs, configured as follows: the +3.3V output contains a linear regulator, is used to power the LVDS interface, should maintain a +/−5% accuracy, and supply an output current of 0.35 A; the +3.6V output contains a linear regulator, is used to power the MSP430, should maintain a +/−5% accuracy, and supply an output current of 0.35 A; the +5V output contains a linear regulator, is used to power the plus rail for op-amps, should maintain a +/−5% accuracy, and supply an output current of 0.35 A; the −5V output receives its power from the +5V supply, has a mV reference, is used to power the minus rail for op-amps and for the photo-detector bias, should maintain a +/−1% voltage accuracy, and supply an output current of 6.25 mA+/−10%. Additionally, the power board has an 80 ohm source resistance, and the main board software can enable/disable the regulator outputs.

The main board interface uses a single channel of the LVDS standard to communicate between boards. This takes place using SPI signaling over the LVDS interface which is connected to the main SPI port of the control processor. The interface also contains a serial port for in-system programming.

The optical detection system of FIG. 23 comprises a control processor, LED drivers, and a photo-detection system. In the exemplary embodiment, the control processor is a TI MSP430F1611 consisting of a dual SPI (one for main board interface, and one for ADC interface) and extended SRAM for data storage. It has the functions of power monitoring, PWM LED control, and SPI linking to the ADC and main board. The LED drivers contain NPN transistor switches, are connected to the PWM outputs of the control processor, can sink 10 mA@12V per LED (80 mA total), and are single channel with 2 LEDs (one of each color) connected to each. The photo-detection system has two channels and consists of a photo-detector, high-sensitivity photo-diode detector, high gain current to voltage converter, unity gain voltage inverting amplifier, and an ADC. Additionally it contains a 16 channel Sigma-delta (only utilizing the first 8 channels) which is connected to the second SPI port of the control processor.

During assembly of the various components on to the PC board, such as may occur on a production line, there are the following considerations. The extremely high impedance of the photo-detection circuit means that a rigorous cleaning procedure must be employed. Such a procedure may include, for example: After surface mount components are installed, the boards are washed on a Wesclean and blow dried upon exiting conveyor. The belt speed can be set at 20-30. The boards are soaked in an alcohol bath for approximately 3 minutes, then their entire top and bottom surfaces are scrubbed using a clean, soft bristle brush. The boards are baked in a 105° F. (40° C.) oven for 30 minutes to dry out all components.

After all the components are installed: the soldered areas of the boards can be hand wash using deionized water and a soft bristle brush. The same soldered areas can be hand washed using alcohol and a soft bristle brush. The boards are allowed to air dry. Once the board is cleaned, the optical circuitry must be conformal coated to keep contaminates out.

Example 5: Fluorescence Detection Module

Figure 24:
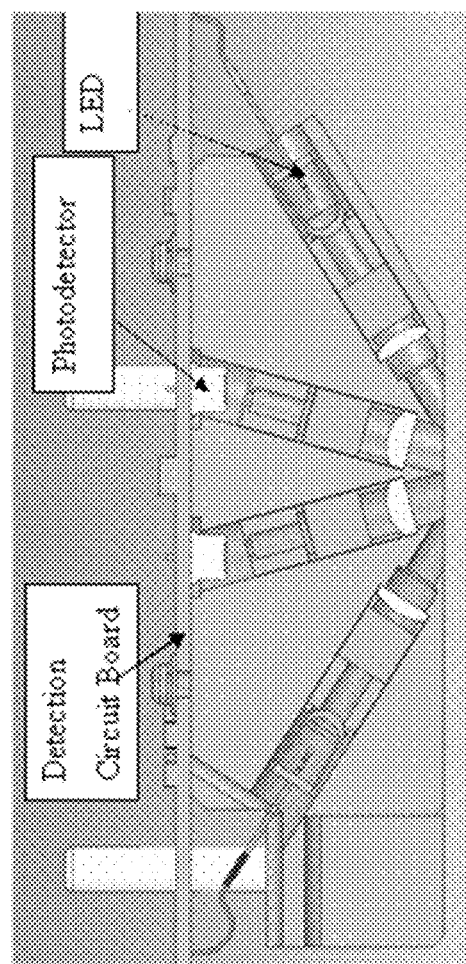
FIG. 24 shows a cross-section of a detector.

A miniaturized, highly sensitive fluorescence detection system (see FIG. 24) can be incorporated for monitoring fluorescence from the biochemical reactions. This optics module can employ light emitting diodes (LED's), photo-diodes and filters/lenses for monitoring, in real-time, the fluorescent signal emanating from the microfluidic cartridge. The current example module contains six identical detection elements and each element can be capable of dual-color detection of a pre-determined set of fluorescent probes.

Software: The software can include two broad parts—user interface and device firmware. The user interface software can allow for aspects of interaction with the user such as—entering patient/sample information, monitoring test progress, error warnings, printing test results, uploading of results to databases and updating software. The device firmware can be the low level software that actually runs the test. The firmware can have a generic portion that can be test independent and a portion specific to the test being performed. The test specific portion ("protocol") can specify the microfluidic operations and their order to accomplish the test.

Figure 25:
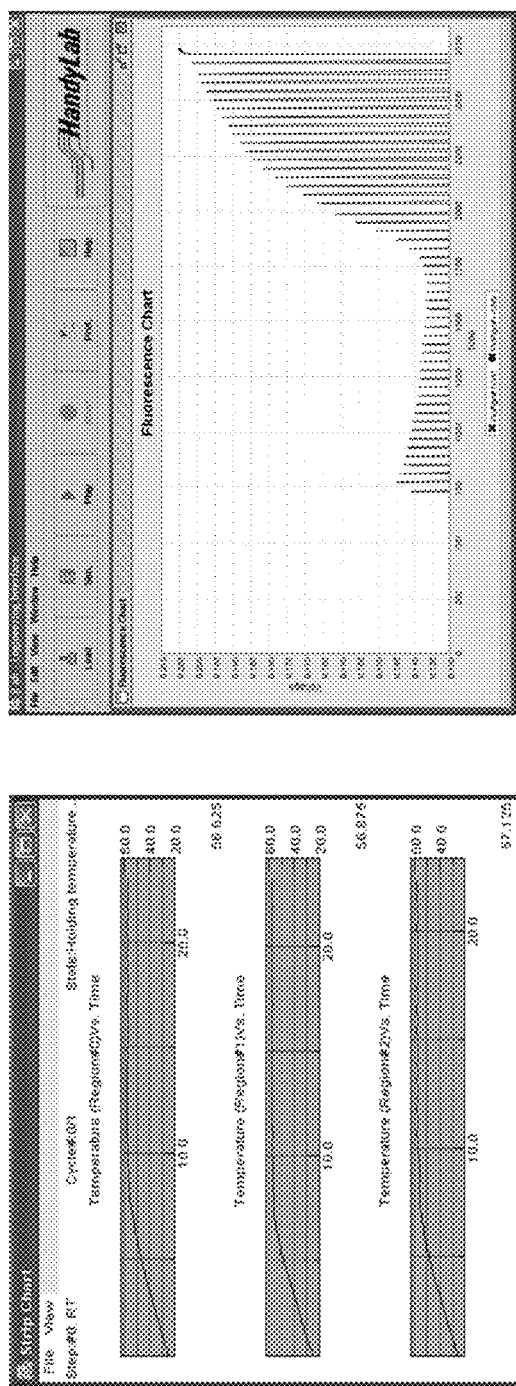
FIG. 25 shows an interface for exemplary software.

FIG. 25 shows screen captures from the programming interface and real time heat sensor and optical detector monitoring. This real time device performance monitoring is for testing purposes; not visible to the user in the final configuration.

Example 6: Scanning Detector Unit

In one embodiment a detector is configured to scan over multiple lanes of a microfluidic substrate such as in a microfluidic cartridge, rather than remain stationary and require a separate detector instance dedicated to each lane. It is also an aspect of this embodiment that multiple detector units are stacked adjacent to one another thereby permitting simultaneous detection from multiple lanes, even as the detector is travelling over the microfluidic substrate. It is a further aspect of this embodiment that each detector unit is a 4-color system, or is a 1-color system, or is a 2-color system.

Figure 26:
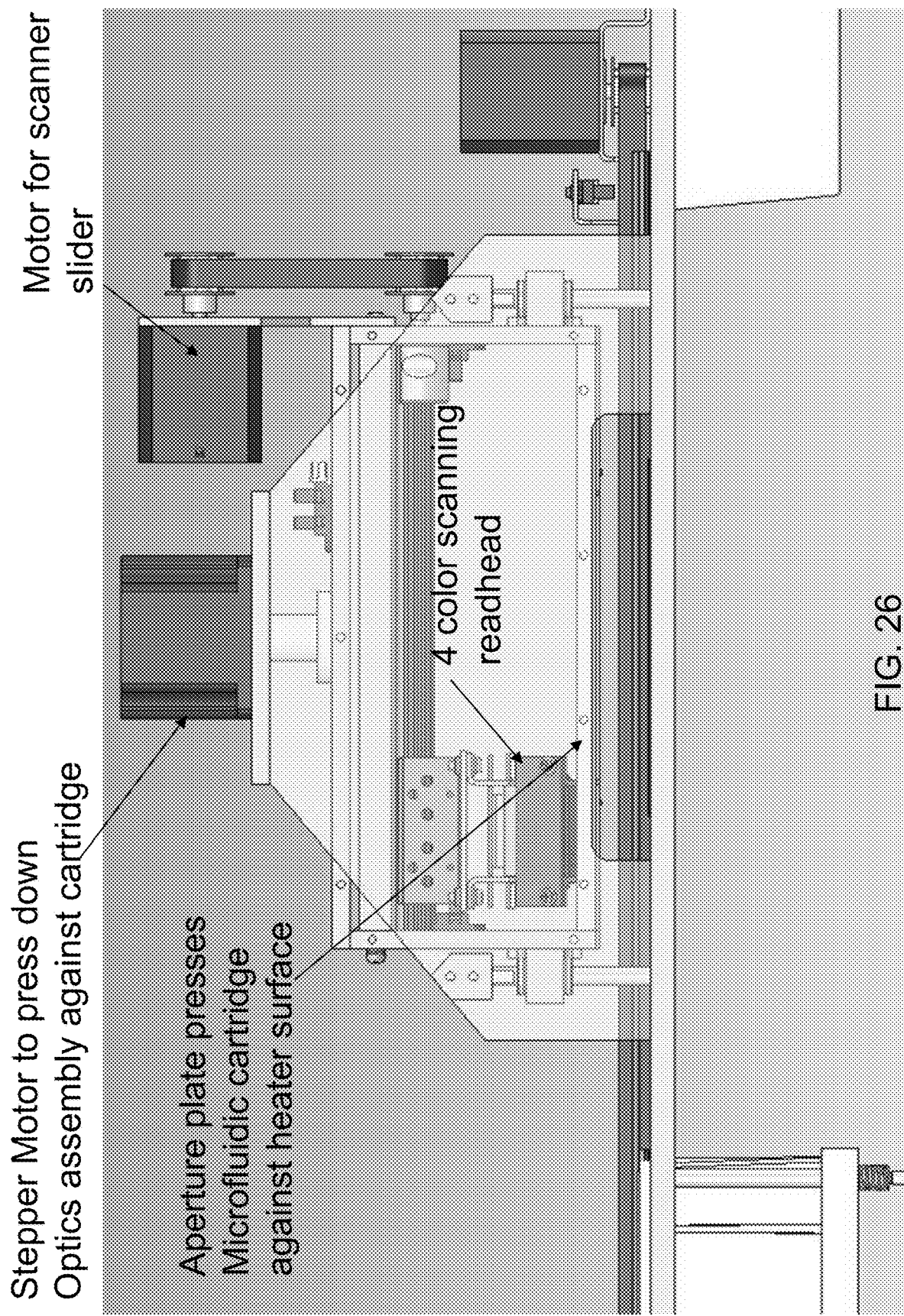
FIG. 26 shows a cross-section of a scanning read-head.
Figure 27:
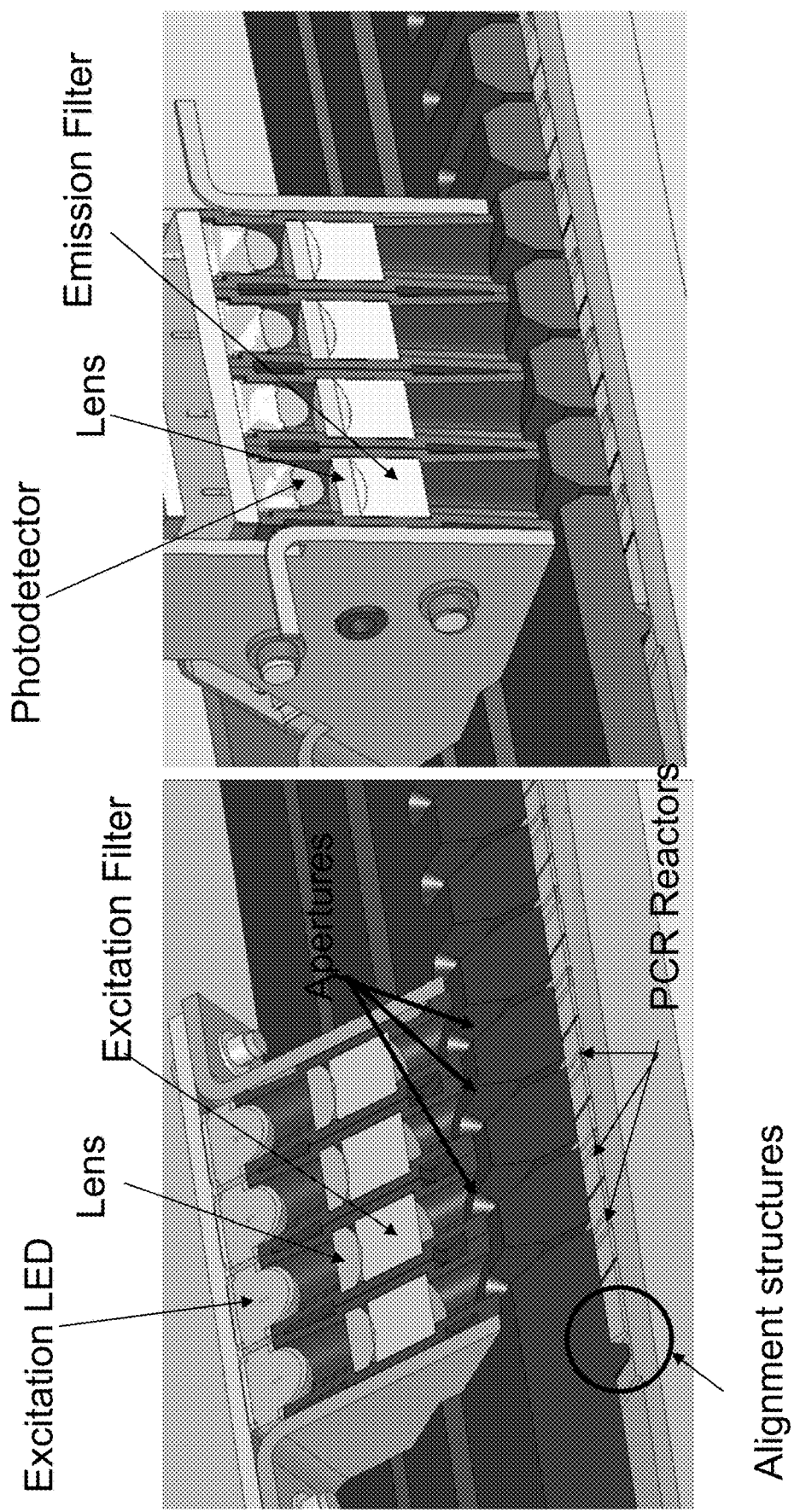
FIG. 27 shows cut-away views of a scanning read head.
Figure 28A:
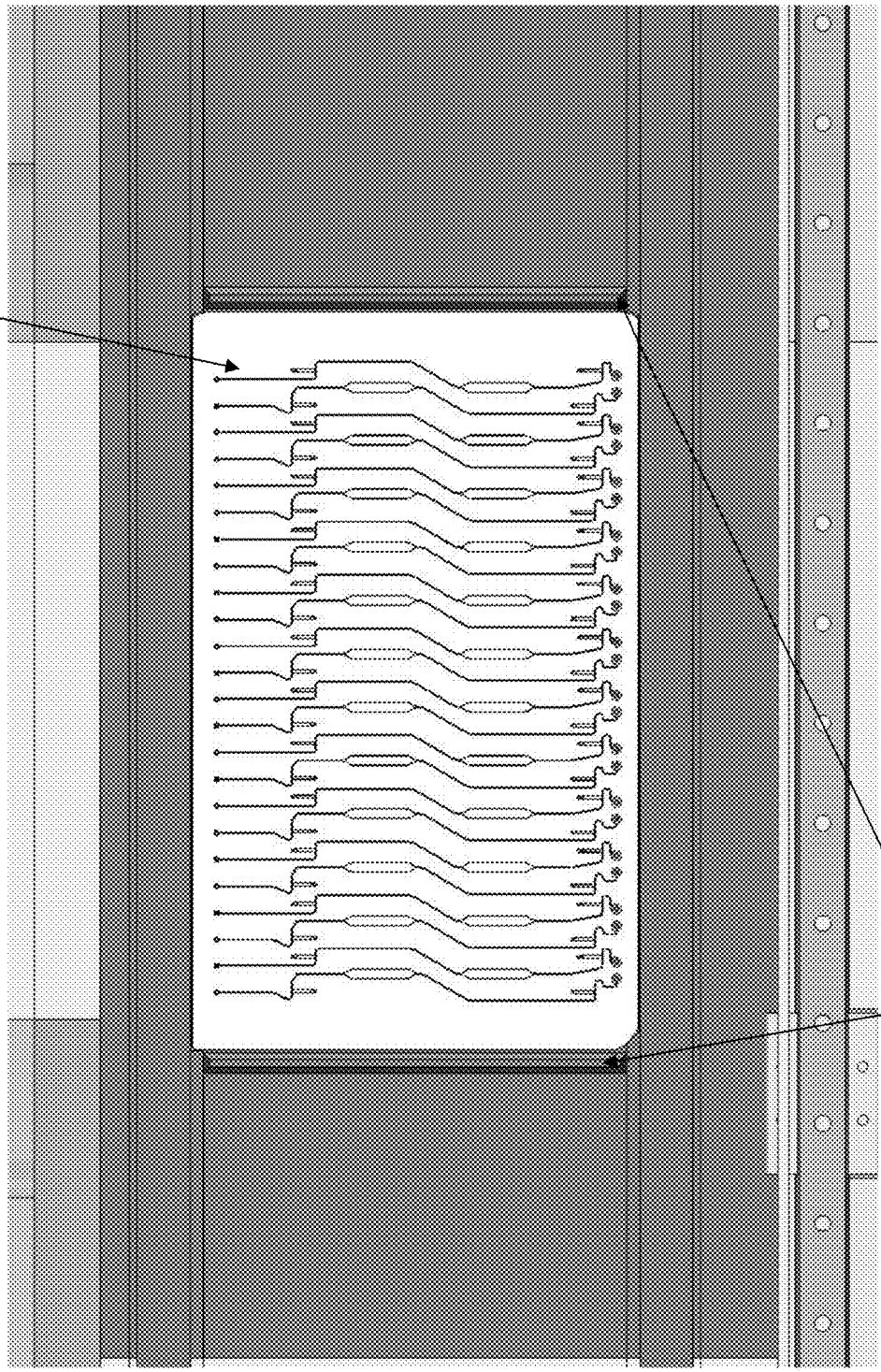
FIGS. 28A and 28B show a microfluidic cartridge aligned to an aperture plate.
Figure 28B:
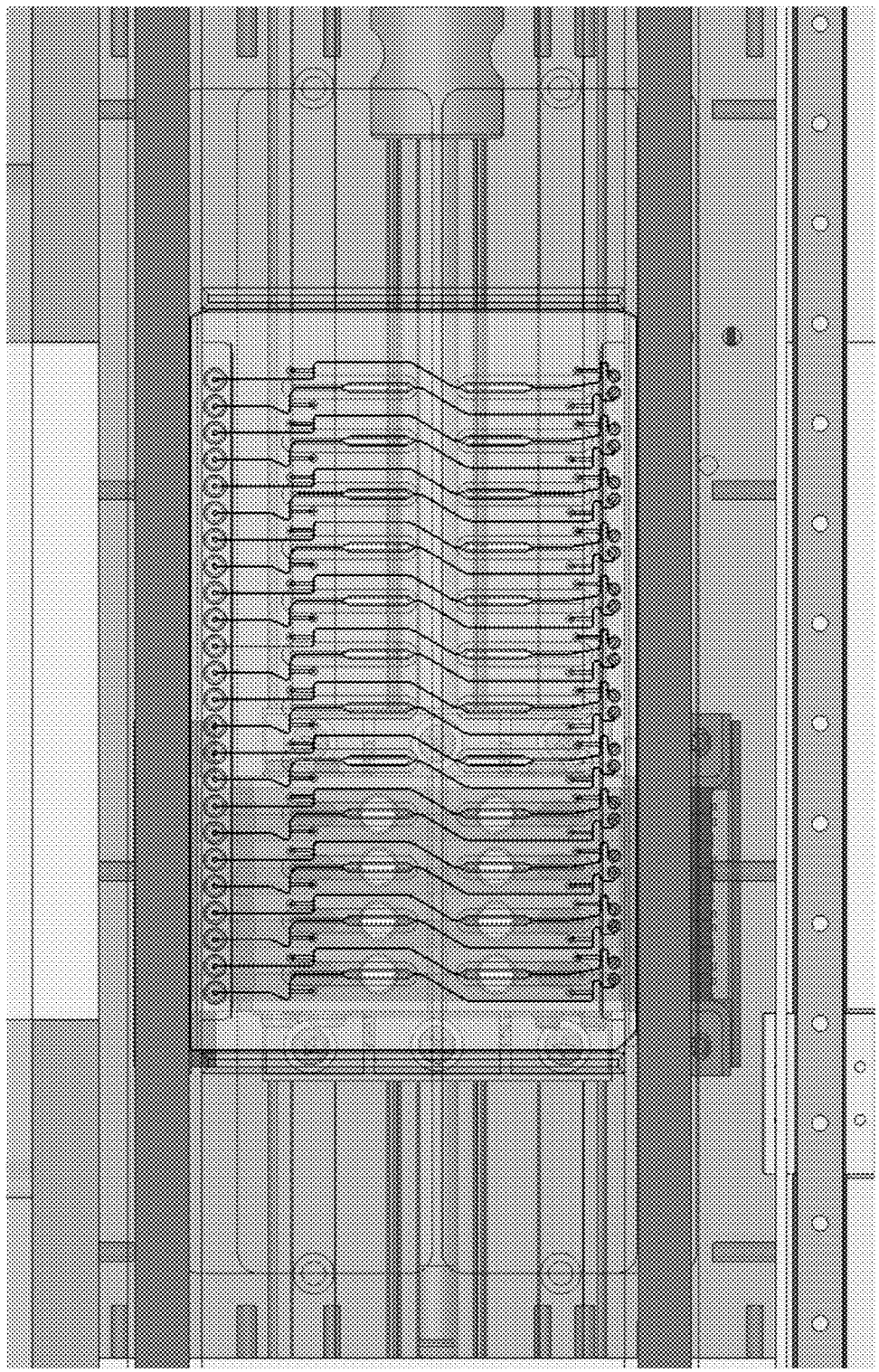

FIG. 26 shows a cross-section of the detector. The reader includes an optical detection unit that can be pressed against a 24-lane microfluidic cartridge to optically interface with the PCR lanes as well as press the cartridge against a microfluidic heater substrate. The bottom of the optics block has 24 apertures (two rows of 12 apertures) that are similar in dimension to the PCR reactors in the cartridge. The aperture plate is made of low fluorescent material, such as anodized black aluminum and during operation, minimizes the total background fluorescence while maximizing the collection of fluorescent only from the PCR reactor (FIG. 27). The bottom of the aperture plate has two beveled edges that help align two edges of the cartridges appropriately such that the apertures line up with the PCR reactors (FIGS. 28A, 28B).

Figure 29:
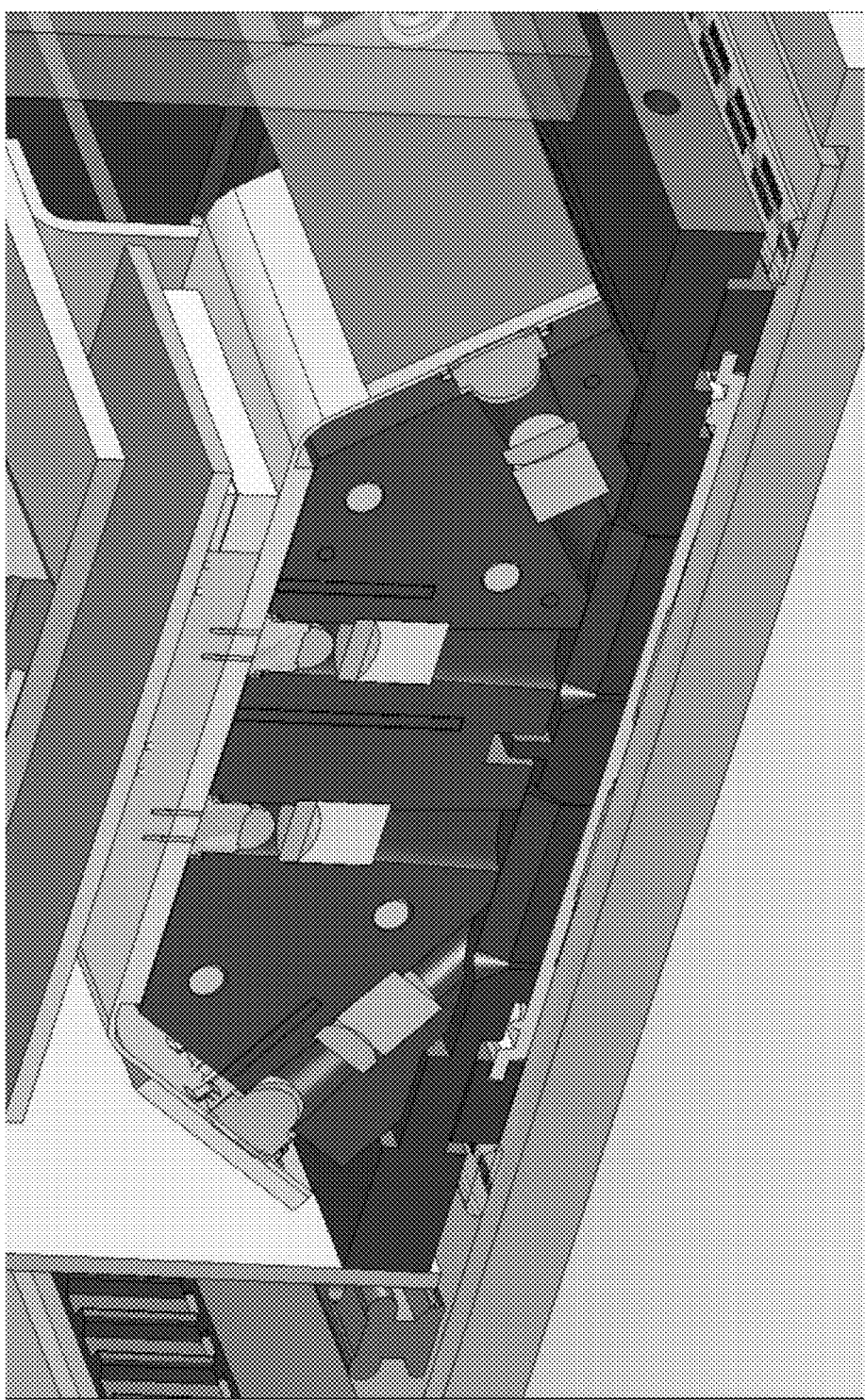
FIG. 29 shows a perspective view of a scanning read head.
Figure 30:
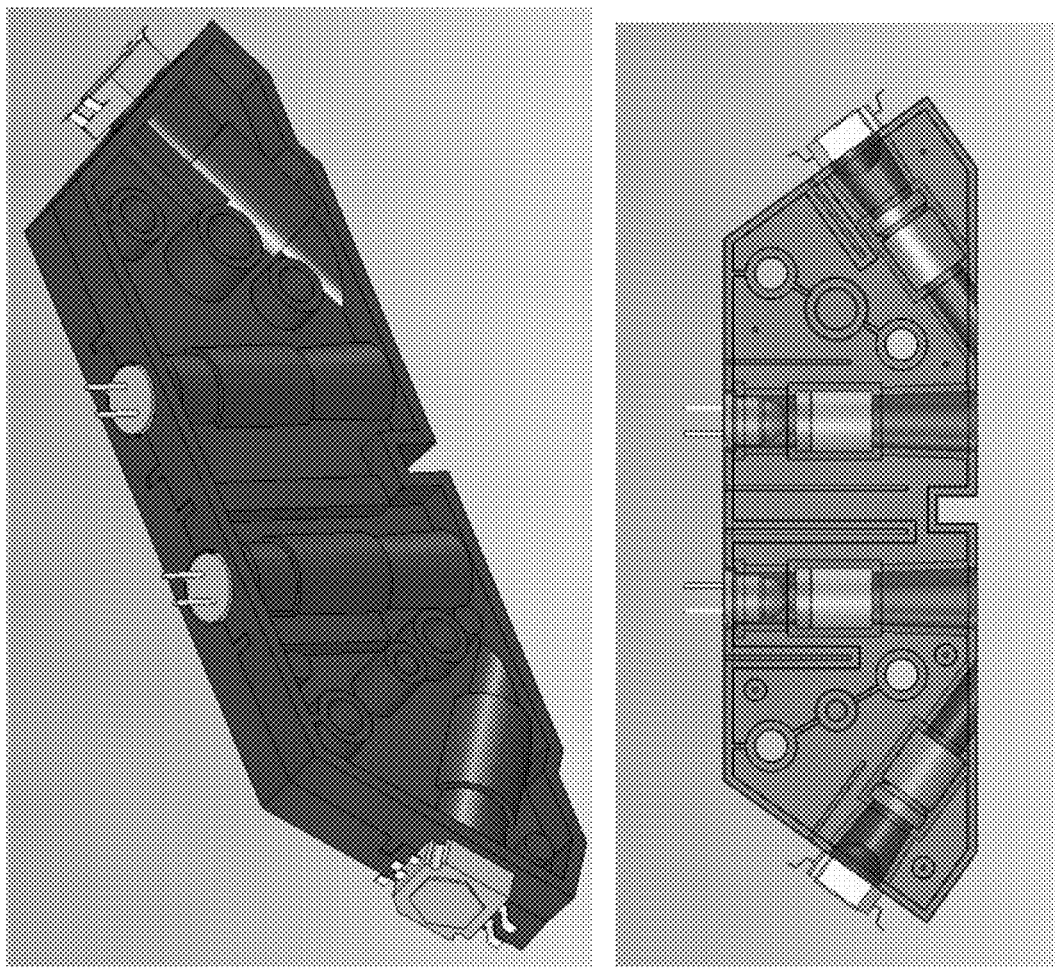
FIG. 30 shows cutaway and cross-section views of a read head.

The optical detection blocks, FIGS. 29 and 30, (total of 8 detection units in this example) are assembled and mounted onto a sliding rail inside the optical box so that the optical units can be scanned over the apertures (FIG. 29). Each unit is able to excite and focus a certain wavelength of light onto the PCR reactor and collect emitted fluorescence of particular wavelength into a photodetector. Each block of the embodiment shown has 2 units and is configured to measure a particular frequency of light from 2 separate locations, such as where a microfluidic substrate is configured with 2 banks (top and bottom) of PCR reactors. By using 4 different colors, one in each of the four parallel detection units, on the top 4 channels and repeating the 4 colors in the bottom channels, the entire scanner can scan up to 4 colors from each of the PCR lanes.

The optics block can be machined out of aluminum and anodized or injection molded using low fluorescence black plastic (FIG. 30). Injection molding can dramatically reduce the cost per unit and also make the assembly of optics easier. The designed units can be stacked back-to-back.

The foregoing description is intended to illustrate various aspects of the present technology. It is not intended that the examples presented herein limit the scope of the present technology. The technology now being fully described, it will be apparent to one of ordinary skill in the art that many changes and modifications can be made thereto without departing from the spirit or scope of the appended claims.

What is claimed:

1. A system comprising:
a receiving bay configured to receive a multi-lane microfluidic cartridge;
a plurality of heaters aligned along a heater axis and configured to apply heat to the multi-lane microfluidic cartridge when the multi-lane microfluidic cartridge is received in the receiving bay, the plurality of heaters comprising at least a first heater and a second heater;
the multi-lane microfluidic cartridge disposed over the plurality of heaters when the multi-lane microfluidic cartridge is removably received in the receiving bay, the multi-lane microfluidic cartridge comprising a first portion comprising a plurality of detection regions within which amplification of polynucleotides is carried out, the plurality of detection regions comprising at least a first detection region and a second detection region, the plurality of detection regions aligned along a first cartridge axis, wherein the heater axis and the first cartridge axis are substantially parallel when the multi-lane microfluidic cartridge is removably received in the receiving bay,
the multi-lane microfluidic cartridge comprising a second portion comprising a plurality of inlets comprising at least a first inlet and a second inlet, the plurality of inlets aligned along a second cartridge axis substantially parallel to the first cartridge axis, the first inlet configured to be loaded with a first sample, the second inlet configured to be loaded with a second sample that is different than the first sample
wherein the first heater is configured to apply heat to the first detection region in order to amplify one or more polynucleotides when the multi-lane microfluidic cartridge is received in the receiving bay and the first sample is received in the multi-lane microfluidic cartridge, and wherein the second heater is configured to apply heat to the second detection region in order to amplify one or more polynucleotides when the multi-lane microfluidic cartridge is received in the receiving bay and the second sample is received in the multi-lane microfluidic cartridge,
a liquid dispenser;
a read head disposed over the multi-lane microfluidic cartridge when the multi-lane microfluidic cartridge is removably received in the receiving bay, the read head configured to detect the presence of the one or more amplified polynucleotides in the plurality of detection regions of the multi-lane microfluidic cartridge when the multi-lane microfluidic cartridge is removably received in the receiving bay,
the read head configured to transmit light onto the first detection region and receive light emitted from the first detection region to detect the presence of one or more amplified polynucleotides in the first detection region of the multi-lane microfluidic cartridge,
the read head further configured to transmit light onto the second detection region and receive light emitted from the second detection region to detect the presence of one or more amplified polynucleotides in the second detection region of the multi-lane microfluidic cartridge,
wherein the read head disposed over the multi-lane microfluidic cartridge does not cover the second cartridge axis when the multi-lane microfluidic cartridge is removably received in the receiving bay.

2. The system of claim 1, wherein the plurality of heaters are configured to cyclically heat in a series of heating phases, each heating phase comprising each of the plurality of heaters being cycled between at least two temperatures, and wherein the plurality of heaters are configured to perform independent amplification reactions in the first detection region and the second detection region.

3. The system of claim 1, wherein the first heater is configured to selectively heat the first detection region and the second heater is configured to selectively heat the second detection region.

4. The system of claim 1, wherein the read head is aligned along the first cartridge axis during detection to allow the liquid dispenser to be aligned along the second cartridge axis.

5. The system of claim 1, wherein the read head is configured to transmit LED light of a specified color that excites a probe in the first detection region, and wherein the read head comprises a photodiode configured to collect emitted light of the specified color.

6. The system of claim 1, wherein the read head is configured to simultaneously detect a fluorescence signal of a first wavelength emitted from the first detection region and a fluorescence signal of a second, different wavelength emitted from the second detection region.

7. The system of claim 1, further comprising a processor comprising instructions configured to heat the first detection region but not heat the second detection region when the multi-lane microfluidic cartridge is removably received in the receiving bay.

8. The system of claim 7, wherein the processor further comprises instructions configured to direct the liquid dispenser to load samples into the multi-lane microfluidic cartridge at different times when the multi-lane microfluidic cartridge is removably received in the receiving bay, the samples passed to a respective detection region independently of one another.

9. The system of claim 1, wherein the read head is configured to perform multiple concurrent measurements of a plurality of fluorescent dyes having different fluorescent emission spectra in the first detection region and the second detection region amplification reaction zone.

10. The system of claim 1, wherein the first heater is configured to heat a distinct location having an average diameter in two dimensions between 1 mm and 15 mm.

11. The system of claim 1, wherein the first heater is configured to heat a surface area of between 5 $mm^2$ and 50 $mm^2$.

12. The system of claim 1, wherein the first heater is configured to heat a surface area of between 1 $mm^2$ and 100 $mm^2$.

13. A system comprising:
a receiving bay configured to receive a multi-lane microfluidic cartridge;
a plurality of heaters aligned along a heater axis and configured to apply heat to the multi-lane microfluidic cartridge when the multi-lane microfluidic cartridge is received in the receiving bay, the plurality of heaters comprising at least a first heater and a second heater;
the multi-lane microfluidic cartridge positioned over the plurality of heaters when the multi-lane microfluidic cartridge is removably received in the receiving bay, the multi-lane microfluidic cartridge comprising a first portion comprising a plurality of detection regions within which amplification of polynucleotides is carried out, the plurality of detection regions comprising at least a first detection region and a second detection region aligned along a first cartridge axis, wherein the heater axis and the first cartridge axis substantially parallel when the multi-lane microfluidic cartridge is removably received in the receiving bay,
the multi-lane microfluidic cartridge comprising a second portion comprising a plurality of inlets comprising at least a first inlet and a second inlet aligned along a second cartridge axis substantially parallel to the first cartridge axis;
wherein the first heater is configured to apply heat to the first detection region in order to amplify one or more polynucleotides when the multi-lane microfluidic cartridge is received in the receiving bay and a first sample is received in the multi-lane microfluidic cartridge, and wherein the second heater is configured to apply heat to the second detection region in order to amplify one or more polynucleotides when the multi-lane microfluidic cartridge is received in the receiving bay and a second sample is received in the multi-lane microfluidic cartridge, the second sample different than the first sample,
a liquid dispenser configured to load the first sample into the first inlet and load the second sample into the second inlet when the multi-lane microfluidic cartridge is removably received in the receiving bay; and
a read head configured to transmit light onto the multi-lane microfluidic cartridge when the multi-lane microfluidic cartridge is removably received in the receiving bay, the read head configured to transmit light onto the first detection region or onto the second detection region or onto both the first and the second detection regions while the read head is positioned over the first portion of the multi-lane microfluidic cartridge,
wherein, when the multi-lane microfluidic cartridge is removably received in the receiving bay, the read head is further configured to receive light emitted from the first detection region or light emitted from the second detection region or light emitted from both the first and the second detection regions to detect the presence of the one or more amplified polynucleotides in the first detection region of the multi-lane microfluidic cartridge or in the second detection region of the multi-lane microfluidic cartridge or in both the first and the second detection regions of the multi-lane microfluidic cartridge while the read head is positioned over the first portion of the multi-lane microfluidic cartridge, and
wherein the read head positioned over the first portion of the multi-lane microfluidic cartridge does not cover the second cartridge axis when the multi-lane microfluidic cartridge is removably received in the receiving bay.

14. The system of claim 13, wherein the plurality of heaters are configured to cyclically heat in a series of heating phases when the multi-lane microfluidic cartridge is removably received in the receiving bay.

15. The system of claim 14, wherein each heating phase comprises each of the plurality of heaters being cycled between at least two temperatures.

16. The system of claim 14, further comprising a processor comprising instructions configured to direct the liquid dispenser to load a third sample into a third inlet of the multi-lane microfluidic cartridge while the read head is transmitting light onto the multi-lane microfluidic cartridge.

17. The system of claim 16, wherein the processor further comprises instructions configured to direct the liquid dispenser to load a fourth sample into a fourth inlet of the multi-lane microfluidic cartridge while the read head is receiving light emitted from the multi-lane microfluidic cartridge.

18. The system of claim 15, further comprising a processor, wherein the processor further comprises instructions to move the read head along the first cartridge axis.

19. The system of claim 15, further comprising a processor, wherein the processor is configured to close valves to prevent movement of the first sample from the first detection region during amplification when the multi-lane microfluidic cartridge is removably received in the receiving bay.

20. The system of claim 15, wherein the read head is configured to simultaneously transmit a first beam of light of a first wavelength onto the first detection region and transmit a second beam of light of a second, different wavelength onto the second detection region, and wherein the read head is further configured to simultaneously receive light emitted from the first detection region and light emitted from the second detection region.

* * * * *

UNITED STATES PATENT AND TRADEMARK OFFICE
CERTIFICATE OF CORRECTION

PATENT NO. : 10,821,446 B1
APPLICATION NO. : 16/910850
DATED : November 3, 2020
INVENTOR(S) : Handique et al.

Page 1 of 1

It is certified that error appears in the above-identified patent and that said Letters Patent is hereby corrected as shown below:

In the Claims

In Column 33, Line 12, Claim 9, after "region" delete "amplification reaction zone".

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*